United States Patent
Lu et al.

(10) Patent No.: US 10,654,868 B2
(45) Date of Patent: May 19, 2020

(54) DIHYDROPYRAZOLE AZEPINE COMPOUND SERVING AS AKT INHIBITOR

(71) Applicant: HARBIN ZHENBAO PHARMACEUTICAL CO., LTD., Heilongjiang (CN)

(72) Inventors: Lun Lu, Shanghai (CN); Zhibo Zhang, Shanghai (CN); Gang Li, Shanghai (CN); Lihong Hu, Shanghai (CN); Charles Z. Ding, Shanghai (CN); Shuhui Chen, Shanghai (CN)

(73) Assignee: HARBIN ZHENBAO PHARMACEUTICAL CO., LTD., Heilongjiang (CN)

( * ) Notice: Subject to any disclaimer, the term of this patent is extended or adjusted under 35 U.S.C. 154(b) by 0 days.

(21) Appl. No.: 16/309,648

(22) PCT Filed: Jun. 13, 2017

(86) PCT No.: PCT/CN2017/088030
§ 371 (c)(1),
(2) Date: Jan. 17, 2019

(87) PCT Pub. No.: WO2017/215588
PCT Pub. Date: Dec. 21, 2017

(65) Prior Publication Data
US 2019/0233434 A1    Aug. 1, 2019

(30) Foreign Application Priority Data

Jun. 16, 2016 (CN) .......................... 2016 1 0428049
Aug. 15, 2016 (CN) .......................... 2016 1 0674021

(51) Int. Cl.
| | | |
|---|---|---|
| C07D 495/14 | (2006.01) |
| C07D 498/14 | (2006.01) |
| C07D 491/147 | (2006.01) |
| A61P 19/02 | (2006.01) |
| A61P 3/10 | (2006.01) |
| A61P 35/00 | (2006.01) |
| C07D 487/14 | (2006.01) |
| A61K 31/553 | (2006.01) |
| A61K 31/551 | (2006.01) |
| A61P 29/00 | (2006.01) |
| A61K 31/55 | (2006.01) |

(52) U.S. Cl.
CPC ............ *C07D 495/14* (2013.01); *A61K 31/55* (2013.01); *A61K 31/551* (2013.01); *A61K 31/553* (2013.01); *A61P 3/10* (2018.01); *A61P 19/02* (2018.01); *A61P 29/00* (2018.01); *A61P 35/00* (2018.01); *C07D 487/14* (2013.01); *C07D 491/147* (2013.01); *C07D 498/14* (2013.01)

(58) Field of Classification Search
None
See application file for complete search history.

(56) References Cited

U.S. PATENT DOCUMENTS 8,207,180 B2 * 6/2012 Vanotti ............... C07D 487/04
514/267

FOREIGN PATENT DOCUMENTS

| CN | 1639151 A | 7/2005 |
|---|---|---|
| CN | 103298461 A | 9/2013 |
| EP | 2002836 A1 | 12/2008 |
| WO | 03076429 A2 | 9/2003 |
| WO | 2008065054 A1 | 6/2008 |
| WO | 2008098104 A1 | 8/2008 |
| WO | 2009089305 A1 | 7/2009 |
| WO | 2009158371 A1 | 12/2009 |
| WO | 2012065935 A1 | 5/2012 |

OTHER PUBLICATIONS

International Search Report and Written Opinion of PCT/CN2017/088030 dated Sep. 7, 2017.
Extended European Search Report issued in European patent application No. 17812699.1 dated Apr. 1, 2019.

* cited by examiner

*Primary Examiner* — Kamal A Saeed
(74) *Attorney, Agent, or Firm* — Harness, Dickey & Pierce, P.L.C.

(57) ABSTRACT

Provided is a dihydropyrazole azepine compound serving as an Akt inhibitor; specifically disclosed is a compound as represented by formula (I) or a pharmaceutically acceptable salt thereof.

12 Claims, No Drawings

DIHYDROPYRAZOLE AZEPINE COMPOUND SERVING AS AKT INHIBITOR

CROSS REFERENCE TO RELATED APPLICATIONS

This application is a U.S. National Phase Application under 35 U.S.C. 371 of International Application No. PCT/CN2017/088030 filed on Jun. 13, 2017. This application claims priority to Chinese Application Nos. 201610428049.6, filed on Jun. 16, 2016, and 201610674021.0, filed on Aug. 15, 2016. The entire disclosures of all of the above application are incorporated herein by reference.

FIELD OF INVENTION

The present invention relates to a dihydropyrazole azepine compound serving as an Akt inhibitor and specifically disclosed is a compound as represented by formula (I) or a pharmaceutically acceptable salt thereof.

PRIOR ARTS

Akt, also known as protein kinase B (PKB), is a silk/threonine protein kinase with a molecular weight of approximately 60 kDa, which is ubiquitous in regulatory networks of eukaryotes and located at an important intersection of multiple signaling pathways, can regulate cytokines, growth factors and oncogene Ras-activated cell survival signals. Akt signaling pathway is closely related to the occurrence and development of various diseases such as malignant tumor, diabetes and rheumatoid arthritis etc., and catches more and more attention. In recent years, continuous in-depth researches not only enable people to have a deeper understanding of the biological role of Akt, but also have made many major breakthroughs in the study of the regulation mechanism of Akt signaling pathway, and its specific role in some human diseases and its molecular regulation mechanism are gradually being elucidated.

Akt consists of a N-terminal regulatory region, an intermediate enzyme active region, a C-terminal regulatory region, and a hinge region linking the PH region to the kinase active region. The N-terminal regulatory region has a platelet-leukocyte c kinase homology region, namely PH region, whose exact mechanism during signal transduction is unclear; the intermediate enzyme active region has catalytic activity for filament/threonine residue phosphorylation, wherein phosphorylation at the Thr308 site in the variable peptide loop (T-loop) is required for activating Akt; a proline-rich hydrophobic domain (HM) is located at the C-terminus, which contains a second phosphorylation site Ser473 essential for activating Akt. In recent years, the corresponding crystal structures of each domain have been analyzed one after another, and there has been a deeper understanding of key phosphorylation sites, ATP binding sites and protein substrate binding sites, which provides foundation for the development of Akt/PKB-specific small molecule inhibitors.

At least three Akt subtypes are currently found in mammals, Akt1 (PKBα), Akt2 (PKBβ) and Akt3 (PKBγ), encoded by three different genes located on chromosomes 14q32, 19q13 and 1q43 respectively, with 85% sequence homology, belonging to the AGC protein kinase family. Mouse embryonic fibroblast studies have found that different Akt subtype-deficient strains eventually lead to different phenotypes: Akt1 deficiency manifests as placental malnutrition, growth delay and weight loss, Akt2 deficiency is characterized by abnormal insulin and blood glucose, and Akt3 deficiency shows a reduction in brain volume. In human diseases, the expression and effects of the three subtypes of Akt are also significantly different.

Akt can be activated by various substances in the cell such as hormones, growth factors, cytokines, intercellular matrix, etc. Akt plays a central role in the PI3K/Akt pathway and is a direct target gene of PI3K. Many cytokines, growth factors, and physical stimuli can phosphorylate Akt by activating PI3K. Akt phosphorylation is often used as an indicator of PI3K activity.

The study of the physiological function of Akt is inseparable from the discovery of its substrate. To date, more than 100 substrates for Akt have been discovered. The three subtypes of Akt and the diverse substrates are the structural basis for their multiple functions. Activated Akt affects the activation state of a series of downstream effector molecules through various signaling pathways, and exerts biological effects such as inhibiting apoptosis and promoting proliferation in cells.

The Akt pathway intersects with many signal pathways to form a complex signal network. In certain cases, the Akt pathway activates NF-κB pro-survival signaling or inhibits JNK/p38 apoptotic signaling, but the interaction between p38 and Akt is inconclusive. Under different cell types, different cell differentiation stages, and different experimental conditions, the interaction between the PI3K/Akt pathway and the Ras/MAPK pathway is evident in the different phases of the two pathways, but whether the regulation of Ras/MAPK pathway subject to Akt pathway is positive or negative, and which regulation predominates in a certain cell has not been fully revealed. Akt signaling pathway is closely related to the occurrence and development of diseases such as tumor and rheumatoid arthritis. The interaction and influence of each pathway may together play an important role in the occurrence of diseases.

Afuresertib (GSK2110183) is an AKT inhibitor (WO/2008/098104) published by GlaxoSmithKline in 2008. It has strong inhibition on Akt subtypes and Akt1-E17K (Ki Akt1/2/3=0.08 nM/2 nM/2.6 nM; Akt1-E17K=0.2 nM). The compound is currently in the second phase of clinical trials with an MTD of 125 mg. This compound still has some adverse effects, mainly expressed as nausea (35.6%), diarrhea (32.9%), and indigestion (24.7%). Therefore, the market still needs new Akt inhibitors with strong inhibition ability and low toxicity.

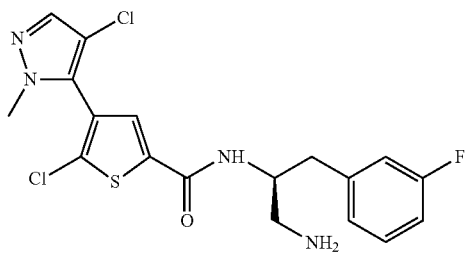

Afuresertib (GSK2110183)

References: WO/2008/098104, WO2009/158371A1.

CONTENT OF THE PRESENT INVENTION

The present invention provides a compound represented by formula (I) or a pharmaceutically acceptable salt thereof,

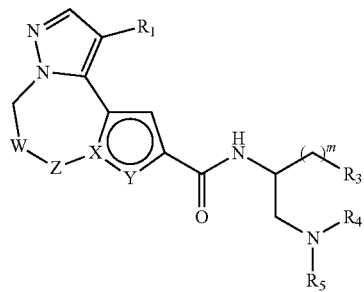
(I)

wherein,
R₁ is H, halogen, CN, CH₃, CH₂CH₃, CF₃, cyclopropyl, phenyl or pyridyl;
X is C or N;
Y is S, O, N or N(CH₃);
Z is C(R₂₁)(R₂₂), C(=O), O or S;
W is C(R₆₁)(R₆₂) or C(=O);

is a five-membered heteroaryl;
each of R₂₁, R₂₂, R₆₁ and R₆₂ is independently selected from the group consisting of H, halogen, hydroxyl, amino and methoxy;
m is 0, 1 or 2;
R₃ is phenyl or pyridyl which is optionally substituted by 1, 2 or 3 R;
each of R₄ and R₅ is H or CH₃;
R is F, Cl, CN or CF₃.

In some embodiments of the present invention, R₁ is F, Cl, Br, I, CN, CH₃, CH₂CH₃, CF₃,

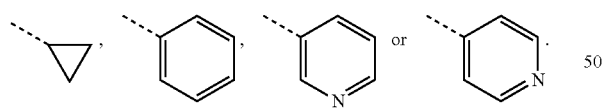

In some embodiments of the present invention, the moiety

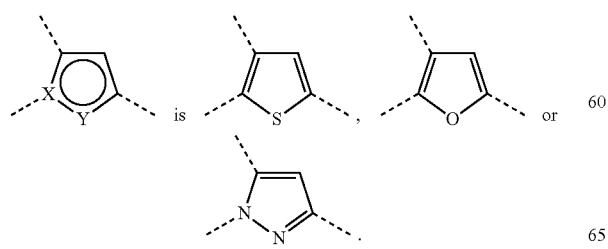

In some embodiments of the present invention, the moiety

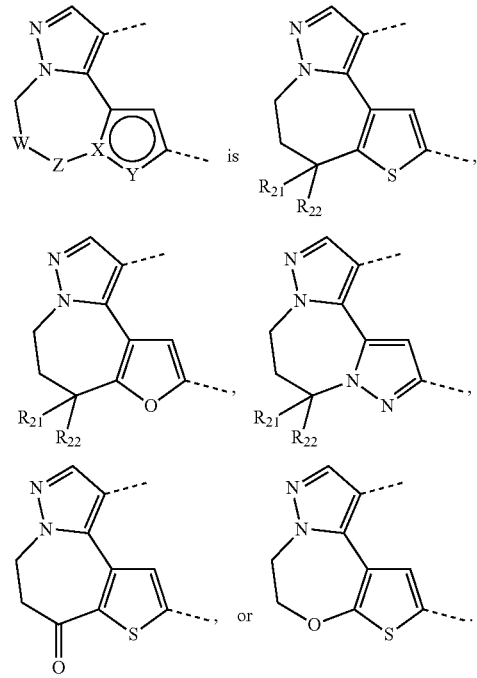

In some embodiments of the present invention, the moiety

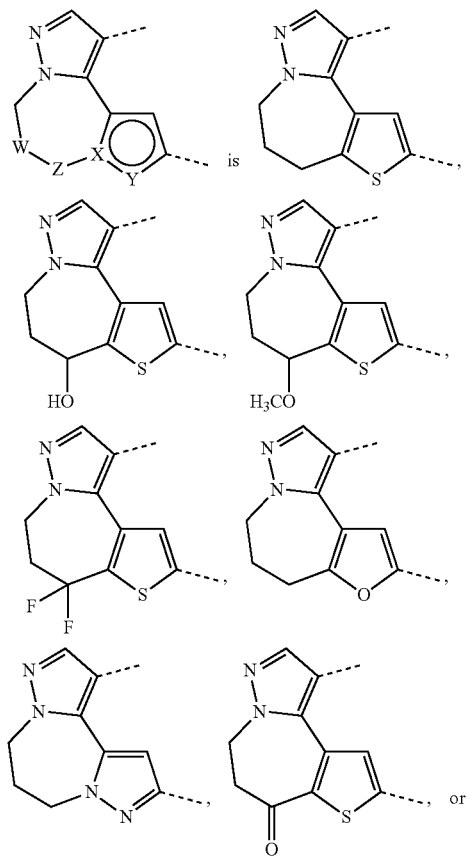

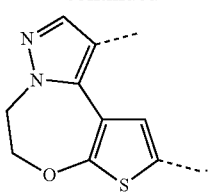

In some embodiments of the present invention, R₃ is

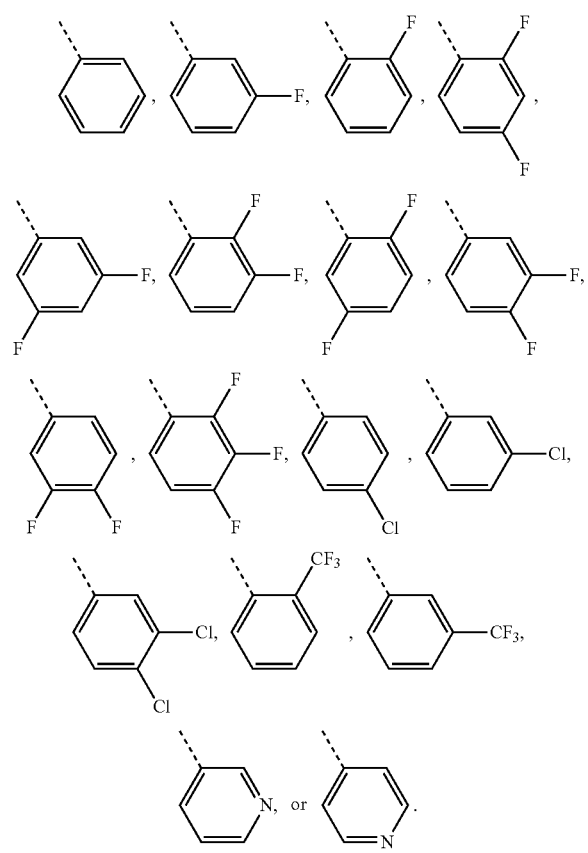

In some embodiments of the present invention, R₁ is F, Cl, Br, I, CN, CH₃, CH₂CH₃, CF₃,

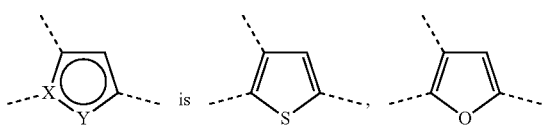

and other variables are defined as above.

In some embodiments of the present invention, the moiety

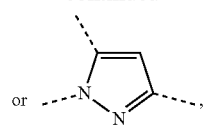

and other variables are defined as above.

In some embodiments of the present invention, the moiety

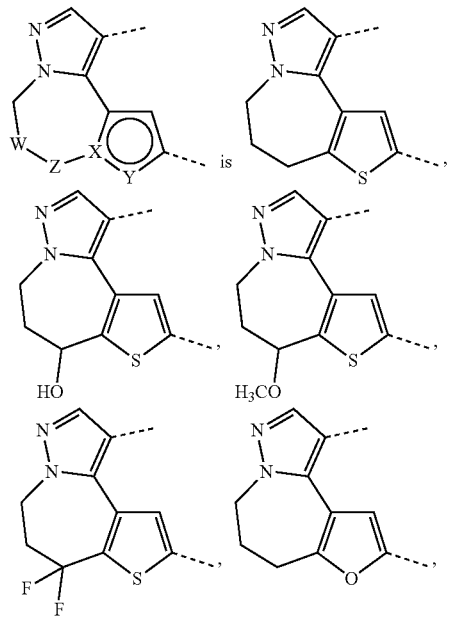

and other variables are defined as above.

In some embodiments of the present invention, the moiety

-continued

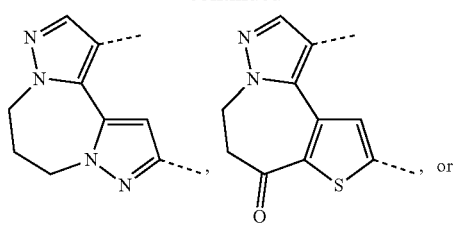

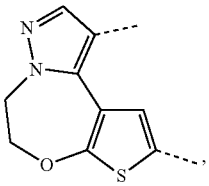

and other variables are defined as above.

In some embodiments of the present invention, $R_3$ is

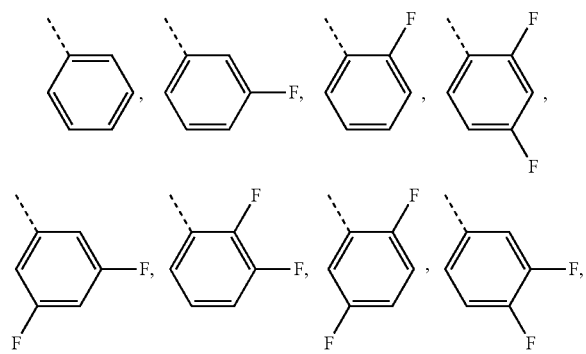

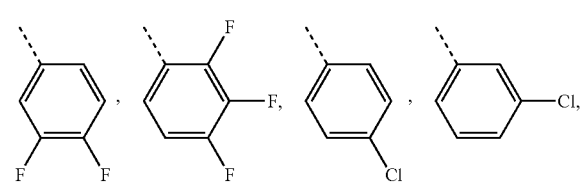

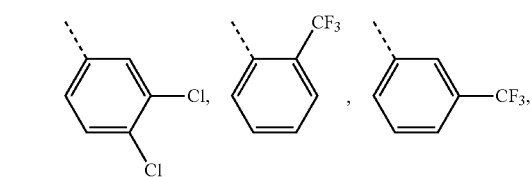

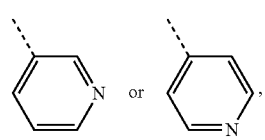

and other variables are defined as above.

In some embodiments of the present invention, the compound or the pharmaceutically acceptable salt thereof is selected from the group consisting of

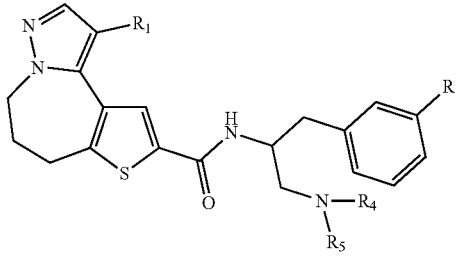
(I-1)

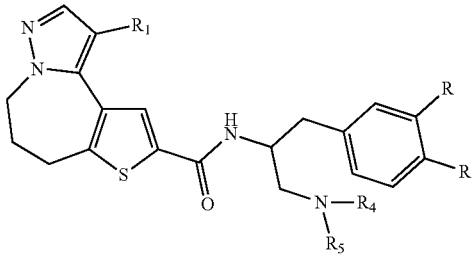
(I-2)

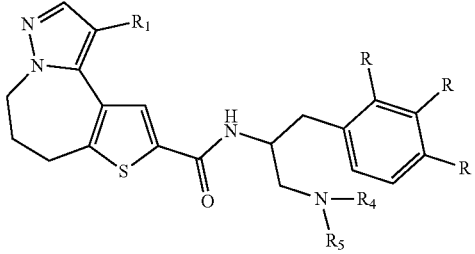
(I-3)

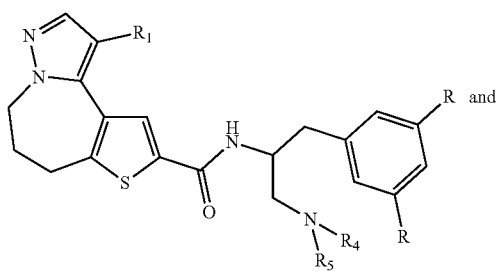
(I-4)

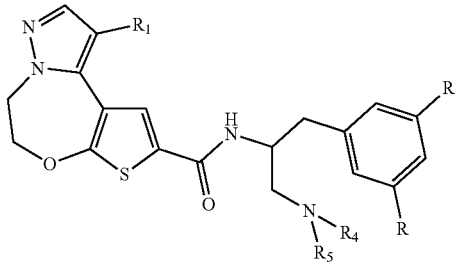
(I-5)

wherein, R, $R_1$, $R_4$, $R_5$ are defined as above.

The present invention also provides the compound or the pharmaceutically acceptable salt thereof, which is selected from the group consisting of

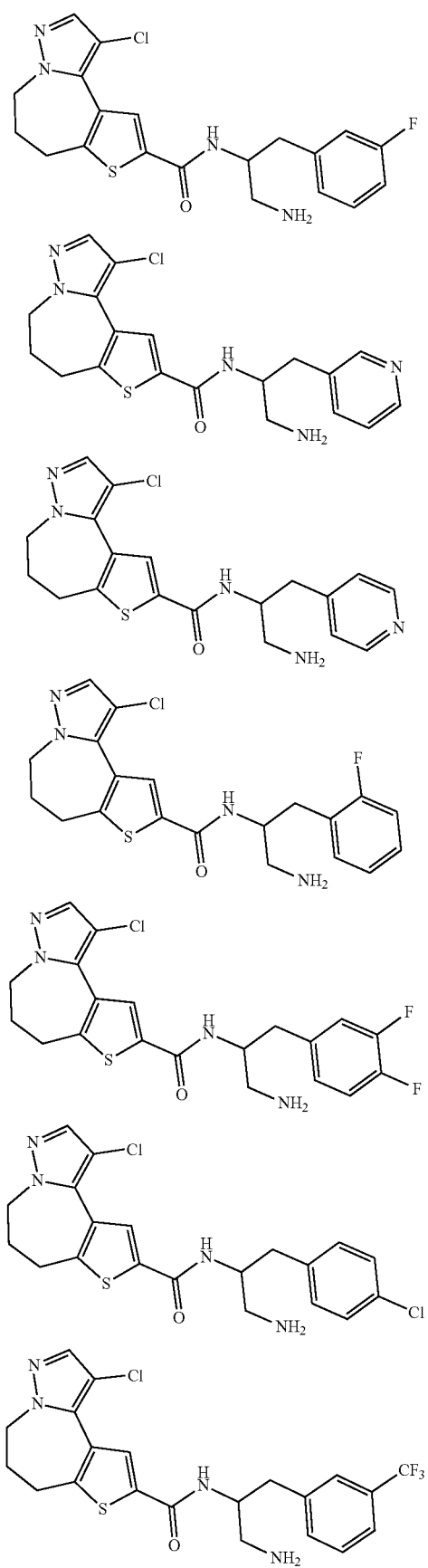
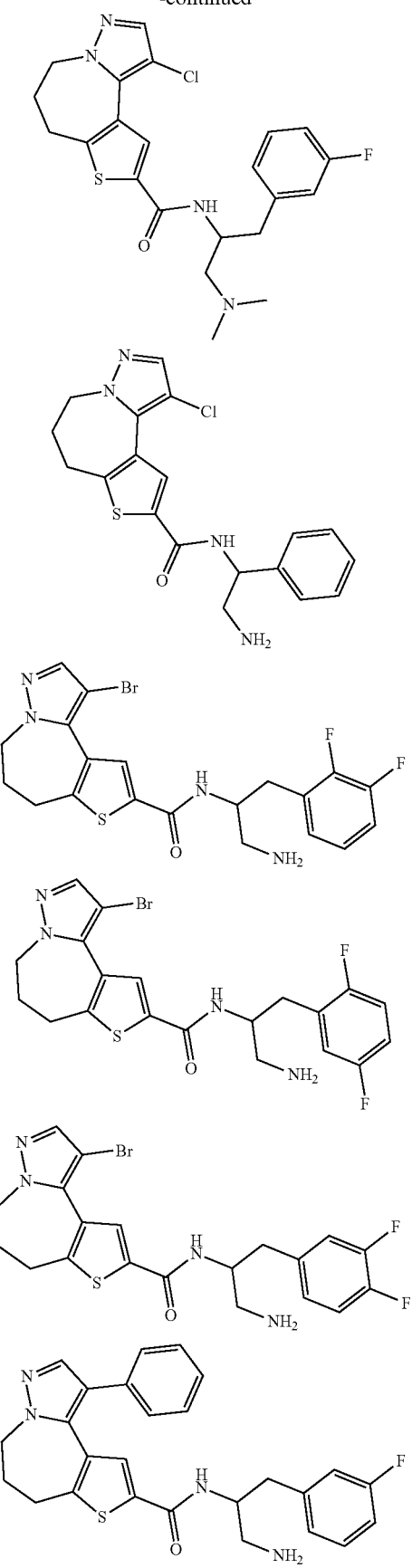

-continued
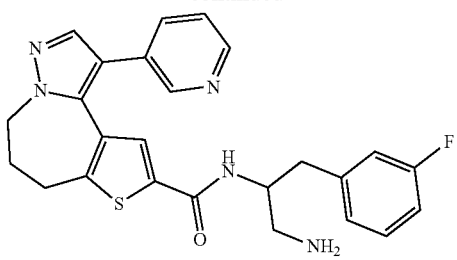
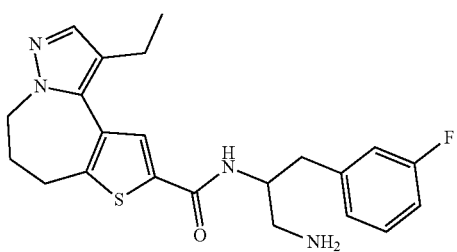
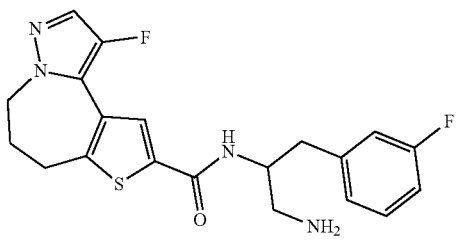
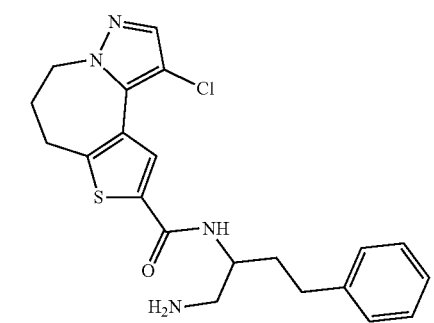
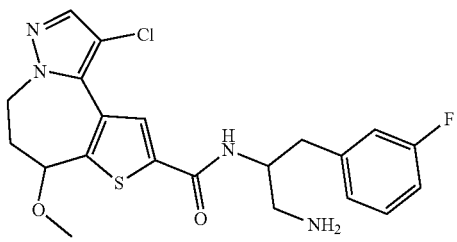
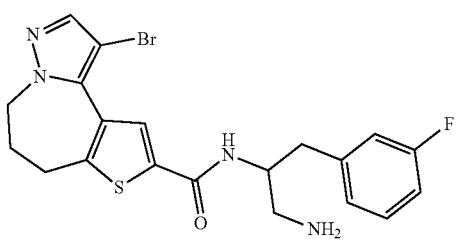
-continued
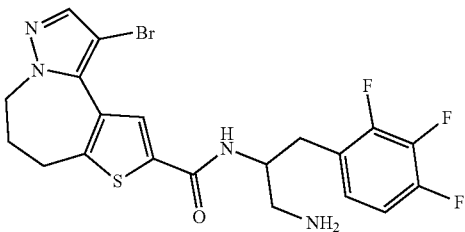
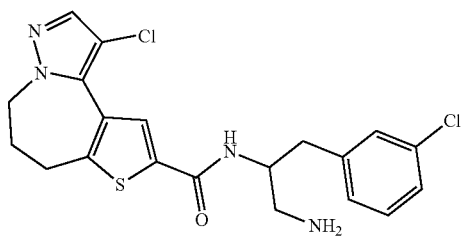
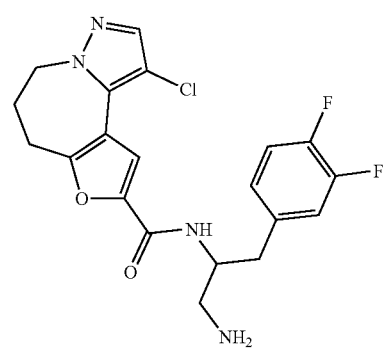
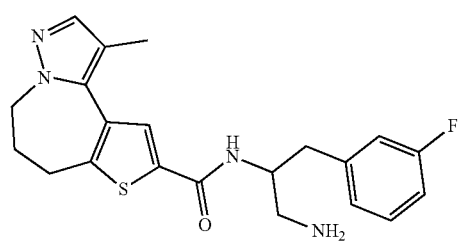
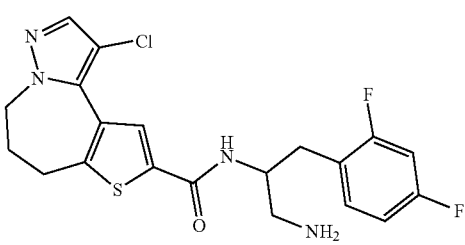
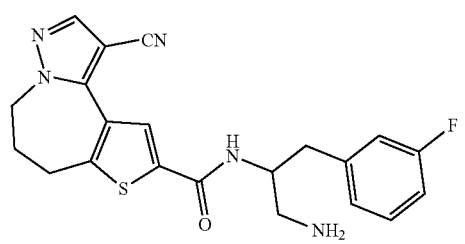

-continued
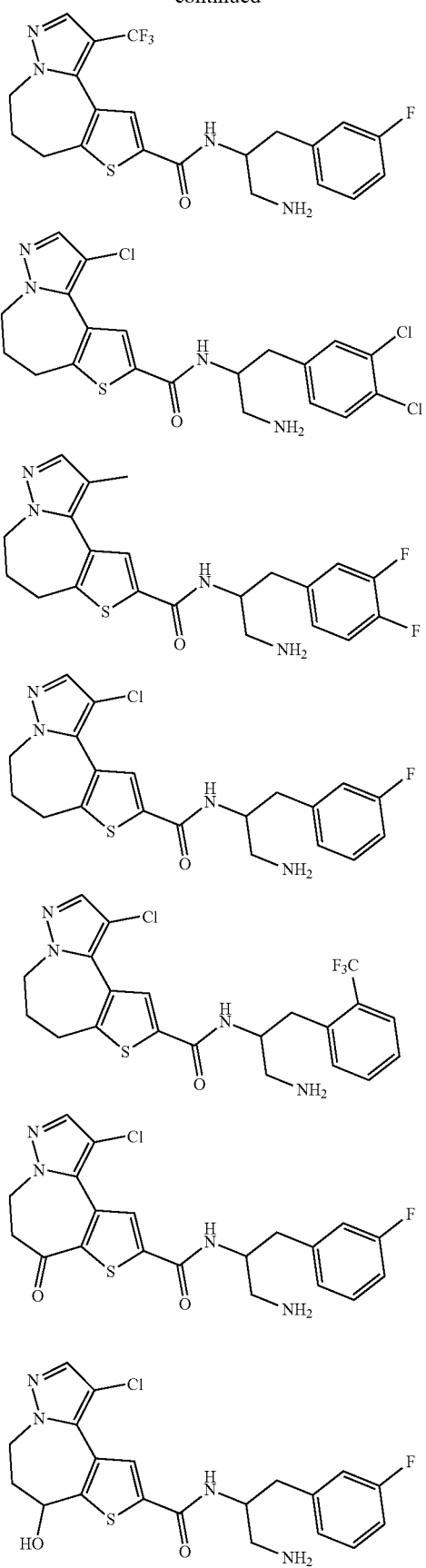
-continued
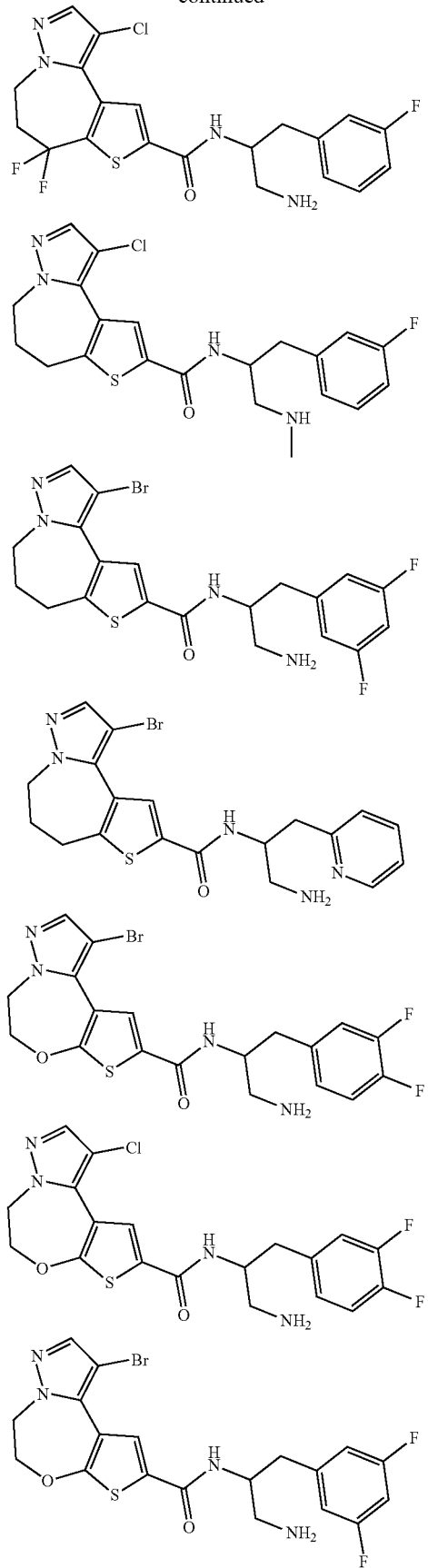

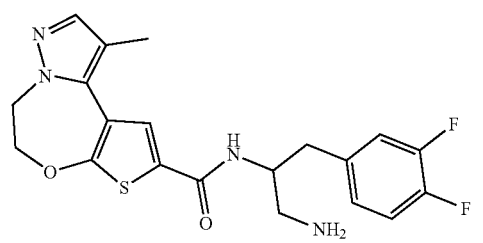
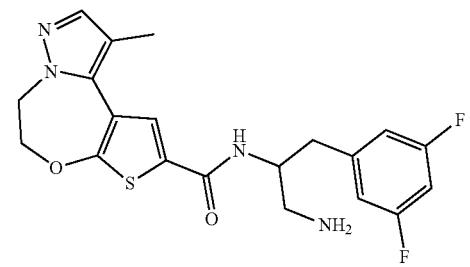
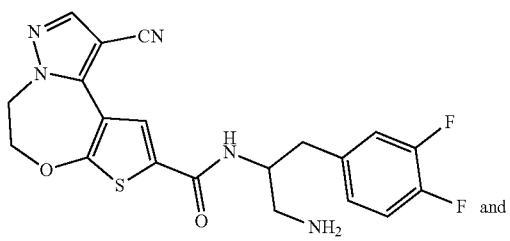
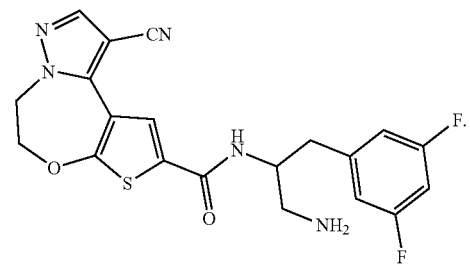
In some embodiments of the present invention, the compound or the pharmaceutically acceptable salt thereof is selected from the group consisting of
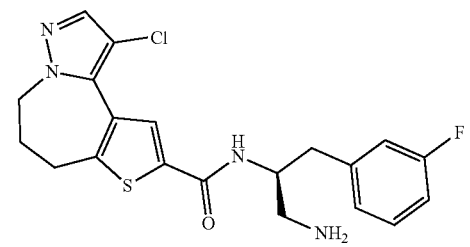
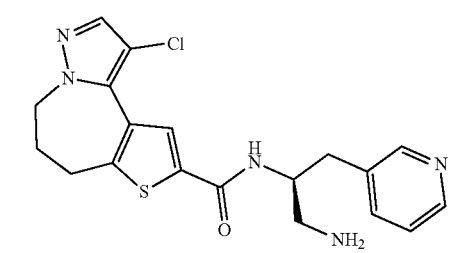
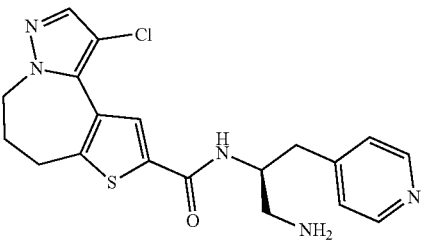
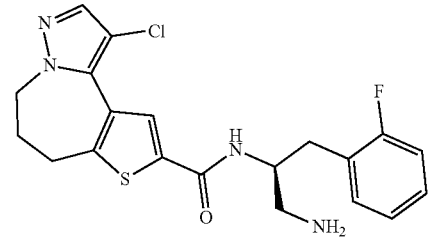
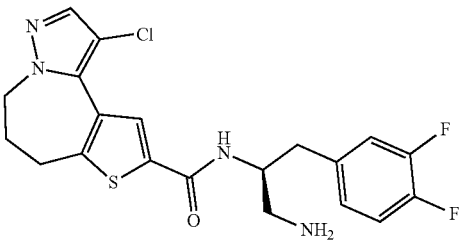
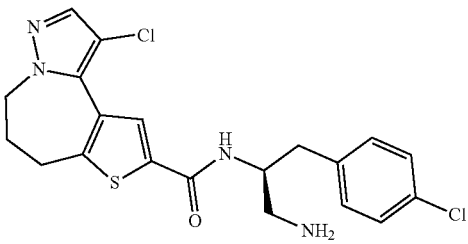
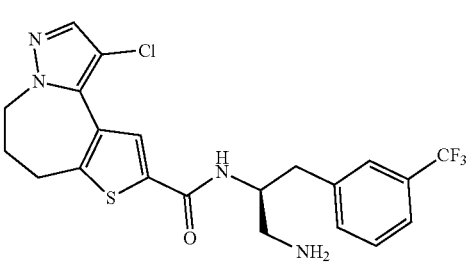
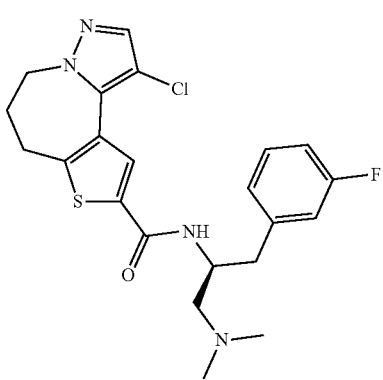

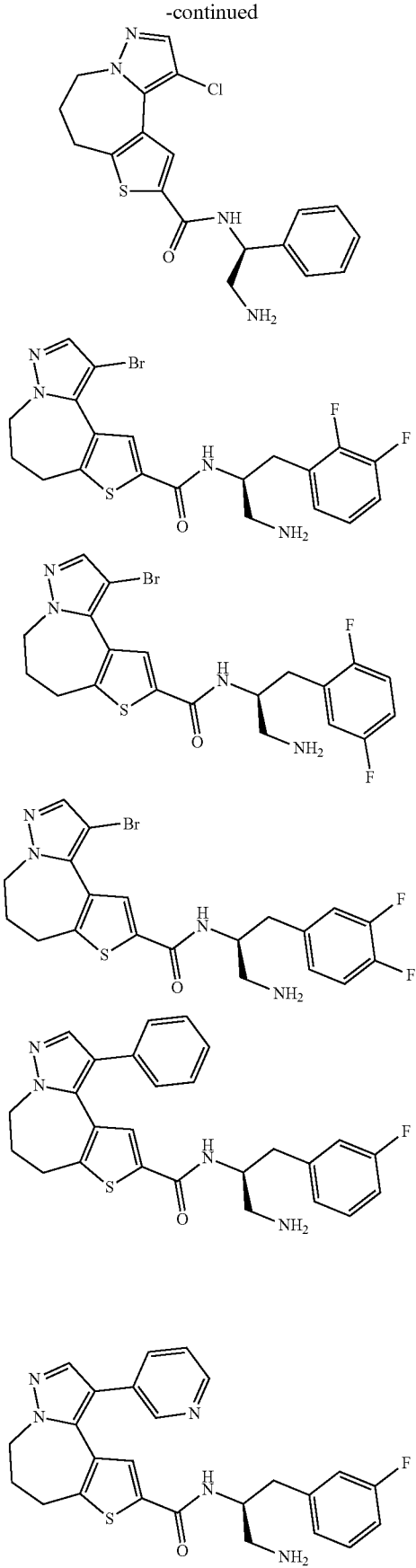
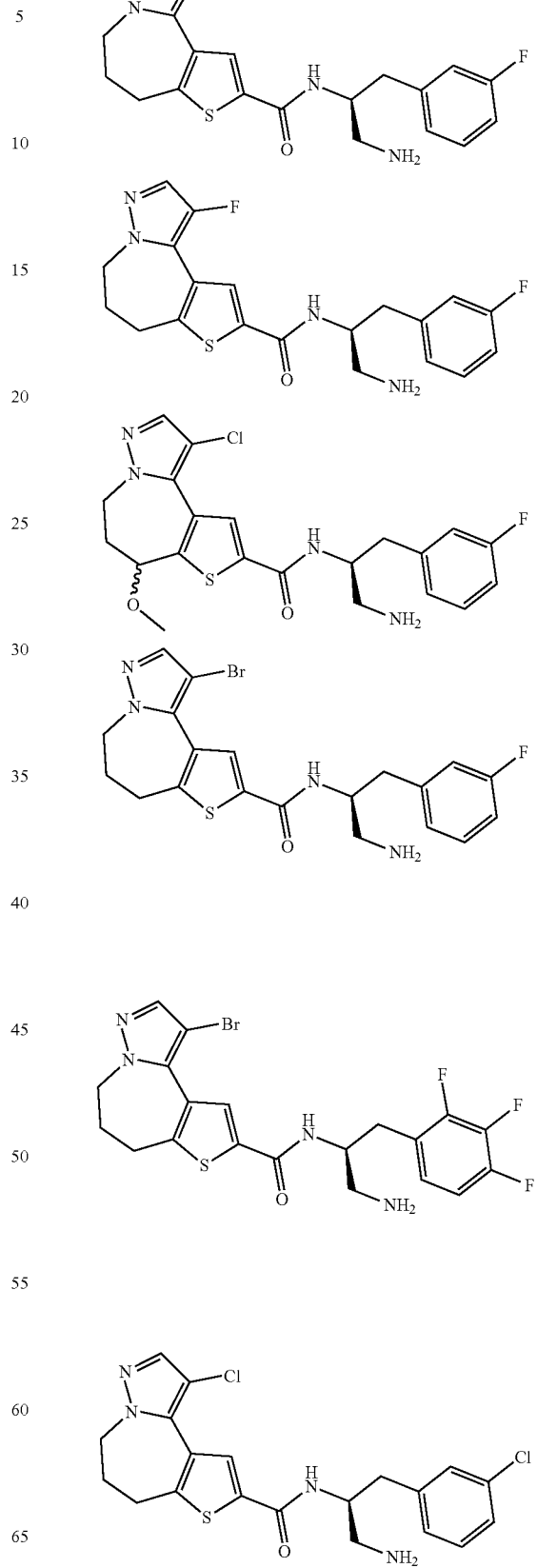

-continued
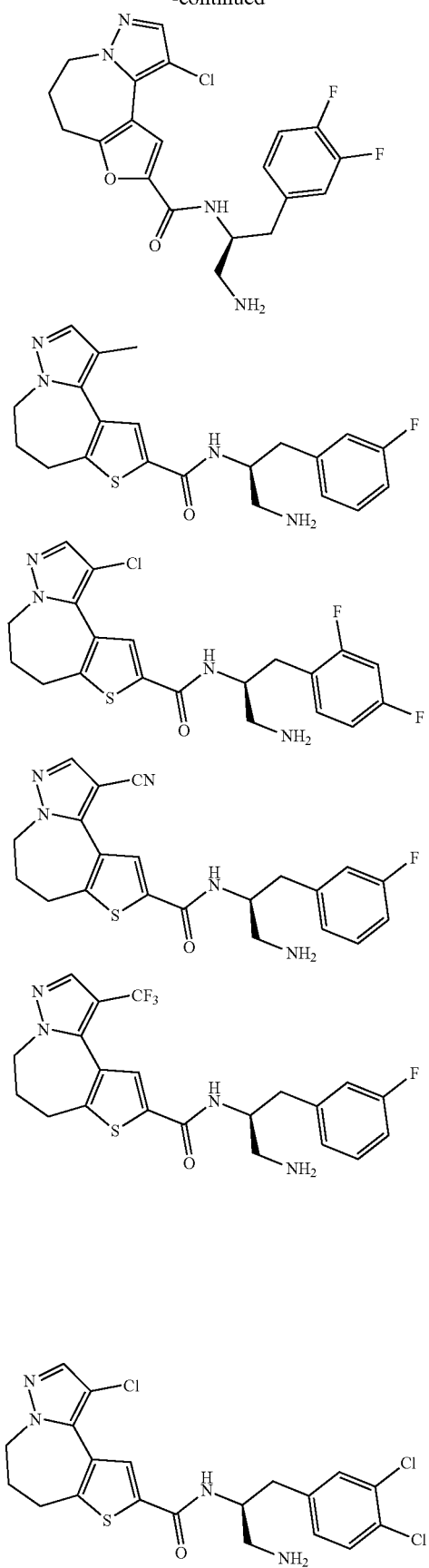
-continued
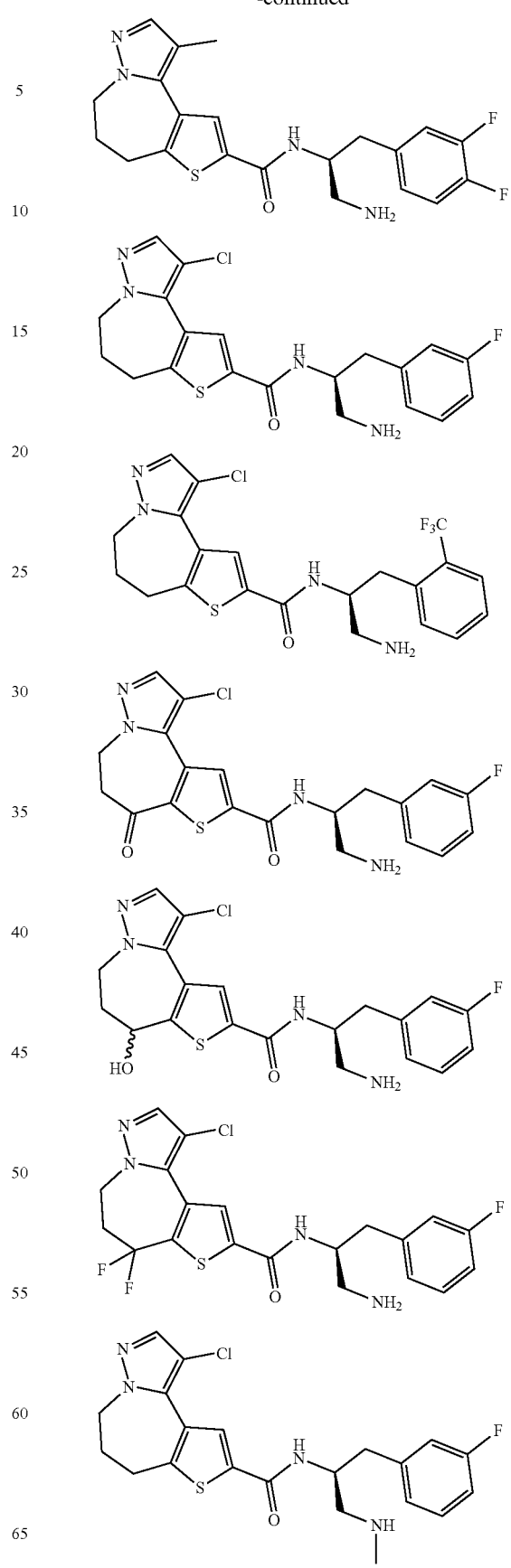

-continued

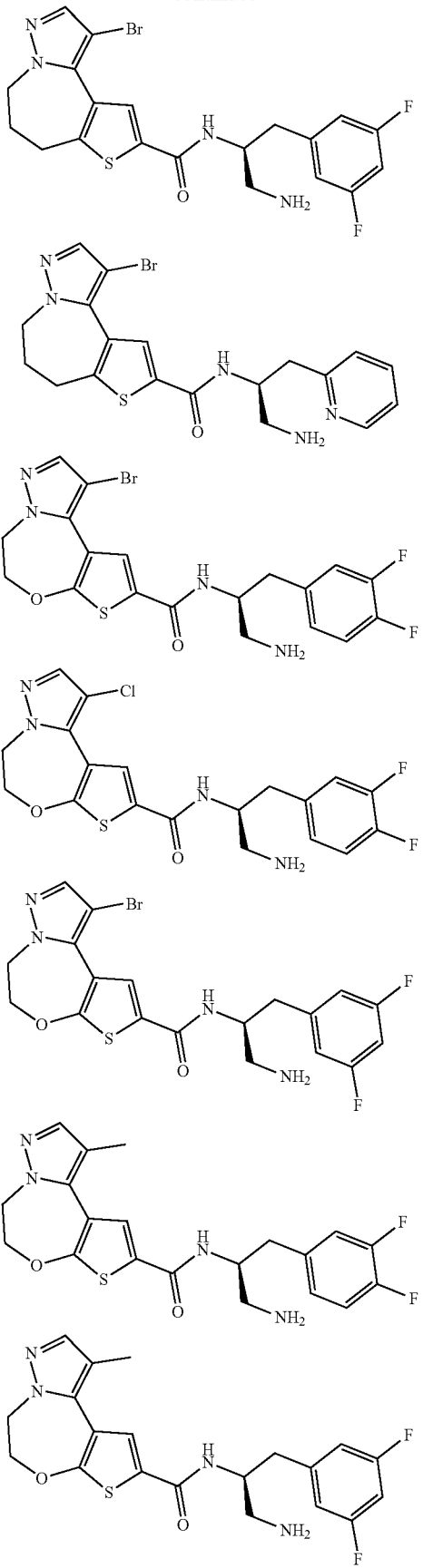

-continued

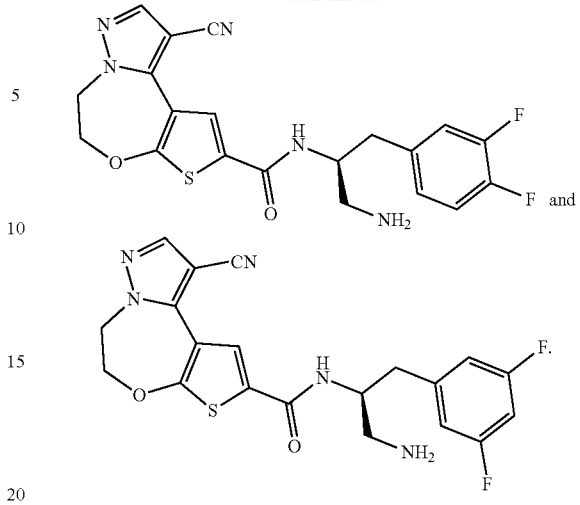

The present invention also provides a pharmaceutical composition, comprising a therapeutically effective amount of the compound or the pharmaceutically acceptable salt thereof, and a pharmaceutically acceptable carrier.

The present invention also provides a use of the compound or the pharmaceutically acceptable salt thereof or the pharmaceutical composition in the preparation of drugs for the treatment of tumor, diabetes, rheumatoid arthritis.

Other embodiments of the present invention are derived from the arbitrary combination of the above variables.

TECHNICAL EFFECT

The dihydropyrazole azezapine compound of the present invention as an Akt inhibitor has a promising prospect in the drugs treating tumor, diabetes and rheumatoid arthritis. Especially in the treatment of cancer, it has a precise therapeutic effect on tumors with Akt1 E17K mutation. Compared with the prior art, the compound of the present invention is excellent in activity, and is particularly effective against Akt1, Akt2, Akt3 kinase, and LNCaP cells. As an AKT inhibitor, dihydropyrazole azezapine compound is expected to become a new class of drug with better therapeutic effects and lower toxic side effects than similar products.

DEFINITION AND DESCRIPTION

Unless otherwise specified, the following terms and phrases used herein are intended to have the following meanings. A particular term or phrase should not be considered indefinite or unclear when not specifically defined, but should be understood in the ordinary sense. When a trade name appears in this document, it is intended to refer to its corresponding product or the active ingredient thereof. The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salts" refers to salts of the compounds of the present invention that are prepared from the compounds having particular substituents of the present invention and relatively non-toxic acids or bases. When the compounds of the present invention contain relatively acidic functional groups, base addition salts can be obtained by contacting the neutrality form of such compounds with a sufficient amount of a base in pure solution or in a suitable inert solvent. Pharmaceutically acceptable base addition salts include salts of sodium, potassium, calcium, ammonium, organic ammonia or magnesium or similar salts. When compounds of the present invention contain relatively basic functional groups, acid addition salts can be obtained by contacting the neutrality form of such compounds with a sufficient amount of the acid in pure solution or in a suitable inert solvent. Examples of pharmaceutically acceptable acid addition salts include inorganic acid salts including, for example, hydrochloric acid, hydrobromic acid, nitric acid, carbonic acid, bicarbonate, phosphoric acid, monohydrogen phosphate, dihydrogen phosphate, sulfuric acid, bisulfate, hydroiodic acid, phosphorous acid and the like; and organic acid salts including, for example, acetic acid, propionic acid, isobutyric acid, maleic acid, malonic acid, benzoic acid, succinic acid, suberic acid, fumaric acid, lactic acid, mandelic acid, phthalic acid, benzene sulfonic acid, p-toluene sulfonic acid, citric acid, tartaric acid, methanylulfonic acid and the like; also includes salts of amino acids (e.g., arginine, etc.) as well as salts of organic acids such as glucuronic acid (see Berge et al., "Pharmaceutical Salts", Journal of Pharmaceutical Science 66: 1-19 (1977)). Certain specific compounds of the present invention contain basic and acidic functional groups so that they can be converted to any base or acid addition salt.

Preferably, the salt is contacted with a base or acid in a conventional manner and the parent compound is isolated, thereby regenerating the neutrality form of the compound. The parent form of a compound differs from its various salt forms in certain physical properties, such as solubility in polar solvents.

As used herein, "pharmaceutically acceptable salts" belong to derivatives of the compounds of the present invention, wherein the parent compound is modified by salt formation with an acid or a base. Examples of pharmaceutically acceptable salts include, but are not limited to, inorganic or organic acid salts of base radicals such as amines, salts formed by acid radicals such as alkali metal or carboxylic acid, and the like. Pharmaceutically acceptable salts include the conventional non-toxic salts or quaternary ammonium salts of the parent compound, such as the salts formed by non-toxic inorganic or organic acids. The conventional non-toxic salts include, but are not limited to, salts derived from inorganic and organic acids which are selected from the group consisting of 2-acetoxybenzoic acid, 2-hydroxyethylsulfonic acid, acetic acid, ascorbic acid, benzosulfonic acid, benzoic acid, bicarbonate, carbonic acid, citric acid, edetic acid, ethanedisulfonic acid, ethanesulfonic acid, fumaric acid, glucoheptonose, gluconic acid, glutamic acid, glycolic acid, hydrobromic acid, hydrochloric acid, hydroiodide, hydroxy, hydroxynaphthyl, isethionic acid, lactic acid, lactose, dodecyl sulfonic acid, maleic acid, malic acid, mandelic acid, methane sulfonic acid, nitric acid, oxalic acid, pamoic acid, pantothenic acid, phenylacetic acid, phosphoric acid, polygalactanaldehyde, propionic acid, salicylic acid, stearic acid, acetic acid, succinic acid, sulfamic acid, sulfanilic acid, sulfuric acid, tannins, tartaric acid and p-toluenesulfonic acid.

The pharmaceutically acceptable salts of the present invention can be synthesized from the parent compound containing acid radicals or base radicals by conventional chemical methods. In general, such salts are prepared by the reaction of these compounds in free acid or base form with a stoichiometric amount of the appropriate base or acid in water or an organic solvent or a mixture of the two. In general, non-aqueous media such as ether, ethyl acetate, ethanol, isopropanol or acetonitrile are preferred.

In addition to salt forms, the compounds provided herein also exist in prodrug forms. The prodrugs of the compounds described herein are readily chemically altered under physiological conditions to be converted into the compounds of the invention. In addition, prodrugs can be converted to the compounds of the present invention by chemical or biochemical methods in the in vivo environment.

Certain compounds of the present invention may exist in unsolvated or solvated forms, including hydrated forms. In general, solvated forms are equivalent to unsolvated forms and both are included within the scope of the present invention.

Certain compounds of the present invention may have asymmetric carbon atoms (optical centers) or double bonds. Racemates, diastereomers, geometric isomers and individual isomers are all included within the scope of the present invention.

Unless otherwise specified, unless otherwise specified, the absolute configuration of a stereocenter is represented by a wedge bond ( ) and a dashed bond ( ) and a wedge bond ( ) or a dashed bond ( ) is represented by a wavy bond ( ), and the relative configuration of a stereocenter is represented by a straight solid bond ( ) and straight dotted bond ( ). When the compounds described herein contain olefinic double bonds or other geometric asymmetry centers, they include E, Z geometric isomers, unless otherwise specified. Likewise, all tautomeric forms are included within the scope of the present invention.

The compounds in this invention can exist specific geometrical or stereo isomer forms. This invention conceives all kinds of this compounds, which includes cis- and trans-isomers, (−)- and (+)-enantiomers, (R)- and (S)-enantiomers, diastereomers, (D)-isomers, (L)-isomers, their racemic mixtures and other mixtures, such as the mixture rich in symmetric isomers and diastereomers, and all these mixtures are included in this invention. Substituents such as alkyl may exist other asymmetric carbon, and all these isomers and their mixture are included in this invention.

The optically active (R)- and (S)-enantiomers, and (D)- and (L)-isomers can be prepared through chiral synthesis, or chiral reagents or other conventional techniques. If a kind of enantiomers is needed in this invention, they can be prepared through asymmetric synthesis or derivatization of chiral auxiliary, where obtained mixtures of diastereomers are separated and then auxiliary groups are ruptured to give pure needed enantiomers. Or, when compounds contain alkaline groups (such as amino) or acidic groups (such as carboxyl), they form salts of diastereomers with appropriate optically active acids or alkalis which are splitted through conventional methods known in this field to gine pure enantiomers. Besides, the separate of enantiomers and diastereomers is through chromatography, and the aforesaid chromatography uses chiral stationary phases, and combines with chemical derivatization optionally (such as amine forming carbamate).

Compounds in this invention can contain unnatural ratio atomic isotopes in one or multi-atoms forming compounds. For example, compounds can be labeled with radioactive isotopes, such as tritium ($^3H$), iodine-125 ($^{125}I$) or C-14

($^{14}$C). The conversion of all the isotopes constituting compounds in this invention, whether radioactivity or not, are included in this invention.

The term "pharmaceutically acceptable carrier" means any preparation or supported media that can deliver effective amount of active substance in this invention, don't interfere biological active of active substance and is nontoxic to hosts or patients, and representative carriers include water, oil, vegetable and mineral, cream base, lotion base, ointment base and so on. These bases include suspending agent, tackifier and penetration enhancer and so on. Their preparations are known to technicians in cosmetic and topical medication fields. Other information about carriers, can refer to the literature Remington: The Science and Practice of Pharmacy, 21st ED., Loppincott, Williams&Wilkins (2005), and contents of this literature merge into this article by quoting.

The term "excipient" usually means carrier, diluent and/or media which are needed for preparation of effective pharmaceutical compositions.

In allusion to medicine or pharmacological activator, the term "effective amount" or "therapeutically effective amount" means enough amount of medicine or agent which can achieve the desired affect without toxin. For the oral preparation in this invention, "effective amount" of a kind of active substance in compositions means the amount needed to achieve the desired affect when combining with another active substance in compositions. The effective amount varies with each individual, and depends on ages of receptors and general situations, also specific active substances. In individual cases, appropriate effective amount can be determined according to routine tests by technicians in this field.

The term "active constituent", "therapeutic agents", "active substance" or "active agent" mean a kind of chemical entities which treat targeted disorders, diseases or symptoms.

"Optional" or "optionally" means that an event or situation described subsequently may, but not necessarily, occur, and the description includes the occurrence of the event or situation mentioned above and the absence of the event or situation described therein.

The term "substituted" means that any one or more hydrogen atoms on a particular atom are replaced with substituents, including deuterium and hydrogen variants, as long as the valence of a particular atom is normal and the substituted compound is stable. When the substituent is a keto (i.e., =O), it means that two hydrogen atoms are substituted. Ketone substitution does not occur on aromatic groups. The term "optionally substituted" means that it may or may not be substituted. Unless otherwise specified, the type and number of substituents may be arbitrary on the basis of being chemically achievable.

When any variable (e.g. R) occurs more than one time in any constituents or formula for a compound, its definition at each occurrence is independent of its definition at every other occurrence. Thus, for example, if a group is shown to be substituted by 0-2 R, then said group may optionally be substituted by up to two R groups and R at each occurrence is selected independently from the definition of R. Also, combinations of substituents and/or variables are permissible only if such combinations result in stable compounds.

When the number of a bonding group is zero, for example, —(CRR)$_0$—, then this bonding group is a single bond.

When one of the variants is selected from a single bond, it means that the two groups which it connects are directly linked. For example, when L represents a single bond in A-L—Z, the structure is actually A-Z When a substituent is vacant, it means that the substituent does not exist. For example, when X is vacant in A-X, it means that the structure is actually A. When a substituent can be attached to more than one atom in a ring, then such substituent may be bonded to any atom on the ring. For example, the moiety

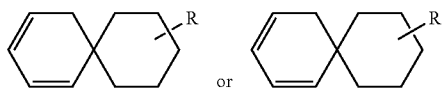

means that R can be substituted at any site of cyclohexyl or cyclohexadiene. When a substituent is listed without indicating the atom via which such substituent is bonded to the rest of compound of a given formula, then such substituent may be bonded via any atom in such substituent. For example, a pyridyl group as a substituent may be attached to the substituted group through any one of the carbon atoms on the pyridine ring. When a linker is listed without indicating its direction of attachment, then such direction of attachment may be arbitrary. For example, the linker L in

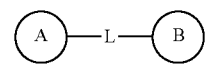

is -M-W—, and the -M-W— may connect the ring A and the ring B in the same direction as the reading order from left to right to form

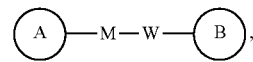

or connect the ring A and the ring B in the opposite direction as the reading order from left to right to form

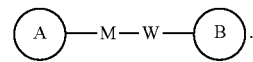

Combinations of linking groups, substituents and/or variables are permitted only if such combinations result in stable compounds.

Unless otherwise specified, the term "hetero" denotes a heteroatom or a heteroatom group (i.e., an atom group containing heteroatoms), including atoms other than carbon (C) and hydrogen (H), and atom groups containing these heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and optionally substituted —C(=O)N(H)—, —N(H)—, —C(=NH)—, —S(=O)$_2$N(H)—, or —S(=O)N(H)—.

Unless otherwise specified, "ring" refers to a substituted or unsubstituted cycloalkyl, heterocycloalkyl, cycloalkenyl, heterocycloalkenyl, cycloalkynyl, heterocycloalkynyl, aryl, or heteroaryl. The so-called ring includes a single ring, a bicyclic ring, a spiro ring, a ring system having two rings sharing one bond, or a bridged ring. The number of atoms on the ring is usually defined as the number of members of the ring. For example, a "5-7 membered ring" refers to that 5-7 atoms are arranged in a circle. Unless otherwise specified, the ring optionally contains 1-3Heteroatoms. Thus, a "5-7 membered ring" includes, for example, phenyl, pyridinyl, and piperidinyl; in another aspect, the term "5-7 membered heterocycloalkyl ring" includes pyridyl and piperidinyl, but does not include phenyl. The term "ring" also includes ring systems containing at least one ring, wherein, each "ring" independently meets the above definition.

Unless otherwise specified, the term "heterocycle" or "heterocyclyl" means stable monocyclic, bicyclic, or tricyclic rings containing heteroatoms or heteroatom groups, which may be saturated, partially unsaturated, or unsaturated (aromatic), and contain carbon atoms and 1, 2, 3, or 4Heterocyclic atoms independently selected from N, O and S, wherein any of the above heterocycles may be fused to a benzene ring to form a bicyclic ring. The nitrogen and sulfur heteroatoms can be optionally oxidized (i.e. NO and S(O)p, p is 1 or 2). The nitrogen atom may be substituted or unsubstituted (i.e. N or NR, where R is H or other substituents as already defined herein). The heterocycles may be attached to the pendant groups of any heteroatom or carbon atom to form a stable structure. If the resulting compound is stable, the heterocycles described herein may be substituted at the carbon or nitrogen position. The nitrogen atom in the heterocycle is optionally quaternized. A preferred embodiment is that when the total number of S and O atoms in the heterocycle exceeds 1, these heteroatoms are not adjacent to each other. Another preferred embodiment is that the total number of S and O atoms in the heterocycle does not exceed 1. As used herein, the term "aromatic heterocyclic group" or "heteroaryl" means a stable 5, 6 or 7 membered monocyclic or bicyclic or 7, 8, 9 or 10 membered bicyclic heterocyclyl aromatic ring, which contains carbon atoms and 1, 2, 3, or 4Heterocyclic atoms independently selected from N, O, and S. The nitrogen atom may be substituted or unsubstituted (i.e., N or NR, where R is H or other substituents as already defined herein). The nitrogen and sulfur heteroatoms can be optionally oxidized (i.e., NO and S(O)p, p is 1 or 2). It is worth noting that the total number of S and O atoms on the aromatic heterocycle does not exceed 1. Bridged rings are also included in the definition of heterocycles. A bridged ring is formed when two non-adjacent carbon or nitrogen atoms are connected by one or more atoms (i.e., C, O, N or S). A preferred bridged ring includes, but is not limited to, one carbon atom, two carbon atoms, one nitrogen atom, two nitrogen atoms, and one carbon-nitrogen group. It is worth noting that a bridge always converts a single ring into a three ring. In the bridged ring, substituents on the ring can also appear on the bridge.

Examples of heterocyclic compounds include, but are not limited to, acridinyl, azocinyl, benzimidazolyl, benzofuranyl, benzosulfydrylfuranyl, benzosulfydrylphenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carb azolyl, carbolinyl, chromanyl, chromene, cinnolinyldecahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indolyl, indolylalkenyl, indolinyl, indolizinyl, indonyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazinyl, phenothiazinyl, benzoxanthinyl, phenoxazinyl, phenazinyl, piperazinyl, piperidinyl, piperidinone, 4-piperidinone, piperonyl, pteridyl, purinyl, pyranyl pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthienyl, thiazolyl, isothiazolylthiophenyl, thienooxazolyl, thienothiazolyl, thienoimidazolyl, thienyl, triazinyl, 1H-1,2,3-triazolyl, 2H-1,2,3-triazolyl, 1H-1,2,4-triazolyl, 4H-1,2,4-triazolyl, and xanthene. Also included are fused-ring and spiro compounds.

Unless otherwise specified, the term "hydrocarbyl" or its subordinate concept (such as alkyl, alkenyl, alkynyl, phenyl, and the like) by itself or as part of another substituent means linear, branched, or cyclic hydrocarbon radicals, or combinations thereof, which may be fully saturated (such as alkyl), unitary or polyunsaturated (such as alkenyl, alkynyl, phenyl), may be mono-substituted or poly-substituted, and may be monovalent (such as methyl), divalent (such as methylene), or polyvalent (such as methine), may include divalent or polyvalent radicals, and have a specified number of carbon atoms (e.g., $C_1$-$C_{12}$ represents 1 to 12 carbons, $C_1$-$C_{12}$ are selected from the group of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ selected from the group of $C_3$, $C_4$, $C_5$, $C_6$, $C_7$, $C_8$, $C_9$, $C_{10}$, $C_{11}$ and $C_{12}$). "Hydrocarbyl" includes, but is not limited to, aliphatic and aromatic hydrocarbyl, wherein the aliphatic hydrocarbyl includes chain and cyclic structures, including but not limited to alkyl, alkenyl, alkynyl, and the aromatic hydrocarbyl includes but not limited to 6-12 membered aromatic hydrocarbyl such as benzene, naphthalene, and the like. In some embodiments, the term "hydrocarbyl" refers to linear or branched chain radicals or combinations thereof, which may be fully saturated, unitary or polyunsaturated, and may include divalent and polyvalent radicals. Examples of saturated hydrocarbon radicals include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and homologues or isomers of n-pentyl, n-hexyl, n-heptyl, n-octyl and other atom groups. Unsaturated alkyl has one or more double or triple bonds, examples of which include, but are not limited to, vinyl, 2-propenyl, butenyl, crotyl, 2-prenyl, 2-(butadienyl), 2,4-pentadienyl, 3-(1,4-pentadienyl), ethynyl, 1- and 3-propynyl, 3-butynyl, and more advanced homologues or isomers.

Unless otherwise specified, the term "heterohydrocarbyl" or its subordinate concept (such as heteroalkyl, heteroalkenyl, heteroalkynyl, heteroaryl, etc.) by itself or in combination with another term means stable, linear, branched or cyclic hydrocarbon radicals or combinations thereof, consisting of a certain number of carbon atoms and at least one heteroatom. In some embodiments, the term "heteroalkyl" by itself or in combination with another term means stable, linear, branched hydrocarbon radicals or combinations thereof, consisting of a certain number of carbon atoms and at least one heteroatom. In a typical embodiment, the heteroatom is selected from the group consisting of B, O, N, and S, wherein the nitrogen and sulfur atoms are optionally oxidized and the nitrogen heteroatoms are optionally quaternized. The heteroatom or heteroatom group may be located at any internal position of the heterohydrocarbyl (including the position where the hydrocarbyl is attached to the rest of the molecule). Examples include but are not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S-

(O)$_2$—CH$_3$, —CH=CH—O—CH$_3$, —CH$_2$—CH=N—OCH$_3$ and —CH=CH—N(CH$_3$)—CH$_3$. Up to two heteroatoms may be continuous, such as —CH$_2$—NH—OCH$_3$.

Unless otherwise specified, the terms "cyclohydrocarbyl", "heterocyclohydrocarbyl" or subordinate concepts (such as aryl, heteroaryl, cycloalkyl, heterocycloalkyl, cycloalkenyl, heterocycloalkenyl, cycloalkynyl, heterocycloalkynyl, etc.) by itself or in combination with other terms mean cyclized "hydrocarbyl", "heterohydrocarbyl" respectively. In addition, for heterohydrocarbyl or heterocyclohydrocarbyl (such as heteroalkyl, heterocycloalkyl), heteroatoms may occupy the position at which the heterocycle is attached to the rest of the molecule. Examples of cyclohydrocarbyl include, but are not limited to, cyclopentyl, cyclohexyl, 1-cyclohexenyl, 3-cyclohexenyl, cycloheptyl and the like. Non-limiting examples of heterocyclic groups include 1-(1,2,5,6-tetrahydropyridinyl), 1-piperidinyl, 2-piperidinyl, 3-piperidinyl, 4-morpholinyl, 3-morpholinyl, tetrahydrofuran-2-yl, tetrahydrofuranindol-3-yl, tetrahydrothiophen-2-yl, tetrahydrothiophen-3-yl, 1-piperazinyl, and 2-piperazinyl.

Unless otherwise specified, the terms "alkyl" means linear or branched saturated hydrocarbyl, which may be mono-substituted (such as —CH$_2$F) or poly-substituted (such as —CF$_3$), and may be monovalent (such as methyl), divalent (such as methylene), or polyvalent (such as methine). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl), etc.

Unless otherwise specified, the terms "alkenyl" means an alkyl having one or more carbon-carbon double bonds at any position of the chain, which may be mono-substituted or poly-substituted, and may be monovalent, divalent, or polyvalent. Examples of alkenyl include vinyl, propenyl, butenyl, pentenyl, hexenyl, butadienyl, piperylene, hexadienyl, etc.

Unless otherwise specified, the term "alkynyl" means an alkyl having one or more carbon-carbon triple bonds at any position of the chain, which may be mono-substituted or poly-substituted, and may be monovalent, divalent, or polyvalent. Examples of alkynyl include ethynyl, propynyl, butynyl, pentynyl, etc.

Unless otherwise specified, the cycloalkyl includes any stable cyclic or polycyclic hydrocarbon group, and any carbon atom is saturated, which may be mono-substituted or poly-substituted, and may be monovalent, divalent, or polyvalent. Examples of cycloalkyl include, but are not limited to, cyclopropyl, norbornyl, [2.2.2]bicyclooctane, [4.4.0]bicyclononane, etc.

Unless otherwise specified, the cycloalkenyl includes any stable cyclic or polycyclic hydrocarbon group containing one or more unsaturated carbon-carbon double bonds at any position of the ring, which may be mono-substituted or poly-substituted, and may be monovalent, divalent, or polyvalent. Examples of cycloalkenyl include, but are not limited to, cyclopentenyl, cyclohexenyl, etc.

Unless otherwise specified, the cycloalkynyl includes any stable cyclic or polycyclic hydrocarbon group containing one or more unsaturated carbon-carbon triple bonds at any position of the ring, which may be mono-substituted, di-substituted, or poly-substituted, and may be monovalent, divalent, or polyvalent.

Unless otherwise specified, the term "halo" or "halogen" by itself or as part of another substituent denotes a fluorine, chlorine, bromine, or iodine atom. In addition, the term "haloalkyl" is meant to include monohaloalkyl and polyhaloalkyl. For example, the term "halo(C$_1$-C$_4$)alkyl" is meant to include but not limited to trifluoromethyl, 2,2,2-trifluoroethyl, 4-chlorobutyl, 3-bromopropyl, and the like. Unless otherwise specified, examples of haloalkyl include, but are not limited to, trifluoromethyl, trichloromethyl, pentafluoroethyl, and pentachloroethyl.

"Alkoxy" represents the above alkyl having a specified number of carbon atoms attached through an oxygen bridge, and unless otherwise specified, C$_{1-6}$ alkoxy includes alkoxy of C$_1$, C$_2$, C$_3$, C$_4$, C$_5$ and C$_6$. Examples of alkoxy include, but are not limited to, methoxy, ethoxy, n-propoxy, isopropoxy, n-butoxy, s-butoxy, t-butoxy, n-pentyloxy and S-pentyloxy.

Unless otherwise specified, the term "aryl" refers to a polyunsaturated aromatic hydrocarbon substituent, which may be mono-substituted or poly-substituted, and may be monovalent, divalent, or polyvalent, and may be monocyclic or polycyclic rings (such as 1 to 3 rings; at least one of which is aromatic), being fused together or covalently linked. The term "heteroaryl" refers to an aryl group (or ring) containing one to four heteroatoms. In one illustrative example, the heteroatom is selected from the group consisting of B, N, O, and S, wherein the nitrogen and sulfur atoms are optionally oxidized and the nitrogen atom is optionally quaternized. A heteroaryl can be attached to the rest of the molecule through a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furyl, thienyl, pyridine, pyrimidinyl, benzothiazolyl, indolyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-Phenyl-4-oxazolyl, 5-oxazolyl, 3-oxoxazolyl, 4-isoxazolyl, 5-isoxazolyl, 2-thiazolyl, 4-thiazolyl, 5-thiazole, 2-furyl, 3-furyl, 2-thienyl, 3-thienyl, 2-pyridyl, 3-pyridyl, 4-pyridyl, 2-pyrimidinyl, 4-pyrimidinyl, 5-benzene And thiazolyl, fluorenyl, 2-benzimidazolyl, 5-fluorenyl, 1-isoquinolinyl, 5-isoquinolinyl, 2-quinoxalinyl, 5-quinoxalinyl, 3-quinoline and 6-quinolinyl. The substituents for any of the above aryl and heteroaryl ring systems are selected from the acceptable substituents described below.

Unless otherwise specified, aryl groups, when used in combination with other terms (e.g., aryloxy, arylthio, arylalkyl) include aryl and heteroaryl rings defined as above. Thus, the term "aralkyl" is intended to include those groups (e.g., benzyl, phenethyl, pyridylmethyl, etc.) where the aryl group is attached to the alkyl group, and including those alkyl groups where the carbon atom (e.g., methylene) has been substituted by an atom such as oxygen, for example, phenoxymethyl, 2-pyridyloxymethyl 3-(1-naphthyloxy)propyl and the like.

The term "leaving group" refers to a functional group or atom that can be substituted by another functional group or atom through a substitution reaction (e.g., an affinity substitution reaction). For example, representative leaving groups include triflate; chlorine, bromine, iodine; sulfonate groups such as mesylate, tosylate, p-bromobenzenesulfonate, p-toluenesulfonates and the like; acyloxy such as acetoxy, trifluoroacetoxy and the like.

The term "protecting group" includes but is not limited to "amino protecting group", "hydroxy protecting group" or "sulfhydryl protecting group". The term "amino protecting group" refers to a protecting group suitable for blocking a side reaction at the amino nitrogen position. Representative amino protecting groups include, but are not limited to, formyl; acyl, such as alkanoyl (e.g., acetyl, trichloroacetyl, or trifluoroacetyl); alkoxycarbonyl, such as tert-butoxycarbonyl (Boc); arylmethoxycarbonyl such as benzyloxycarbonyl (Cbz) and 9-fluorenylmethyloxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group that is suitable for blocking the side reaction of hydroxyl groups. Representative hydroxy protecting groups include, but are not limited to, alkyl such as methyl, ethyl, and tert-butyl; acyl such as alkanoyl (such as acetyl); arylmethyl such as benzyl (Bn), p-methoxybenzyl (PMB), 9-fluorenylmethyl (Fm) and diphenylmethyl (benzhydryl, DPM); silyl such as trimethylsilyl (TMS) and tert-butyl dimethylsilyl (TBS) and the like.

The solvents used in the present invention are commercially available.

The solvents used in the present invention are commercially available. The present invention uses the following abbreviations: aq for water; HATU for O-(7-azabenzotriazol-1-yl)-N,N,N',N'-tetramethyluronium hexafluorophosphate; EDC for N-(3-dimethylaminopropyl)-N'-ethylcarbodiimide hydrochloride; m-CPBA for 3-chloroperoxybenzoic acid; eq for equivalent, equal; CDI for carbonyldiimidazole; DCM for dichloromethane; PE for petroleum ether; DIAD for diisopropyl azodicarboxylate; DMF for N,N-dimethylformamide; DMSO for dimethyl sulfoxide; EtOAc for ethyl acetate ester; EtOH for ethanol; MeOH for methanol; CBz for benzyloxycarbonyl, an amine protecting group; BOC for tert-butoxycarbonyl, an amine protecting group; Fmoc for methoxycarbonyl, an amine protecting group; HOAc for acetic acid; NaCNBH$_3$ for sodium cyanoborohydride; r.t. for room temperature; O/N for overnight; THF for tetrahydrofuran; Boc$_2$O for di-tert-butyl dicarbonate; TFA for trifluoroacetic acid; DIPEA for diisopropylethylamine; SOCl$_2$ for thionyl chloride; CS$_2$ for carbon disulfide; TsOH for p-toluenesulfonic acid; NFSI for N-fluoro-N-(phenylsulfonyl) phenylsulfonyl amide; NC S for 1-chloropyrrolidine-2,5-dione; n-Bu$_4$NF for tetrabutylammonium fluoride; iPrOH for 2-propanol; mp for melting point; LDA for lithium diisopropylamide.

Compounds are named by hand or ChemDraw® software, and commercially available compounds are named after supplier catalog names.

DETAILED DESCRIPTION OF THE PREFERRED EMBODIMENT

The following examples further illustrate the present invention, but the present invention is not limited thereto. While the present invention has been described in detail and with reference to specific embodiments thereof, it will be apparent to those skilled in the art that various changes and modifications can be made therein without departing from the spirit and scope thereof.

Embodiment 1

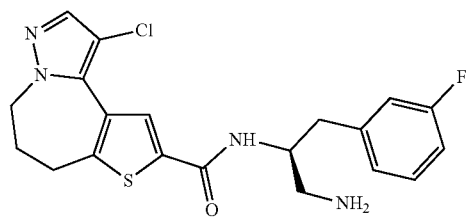

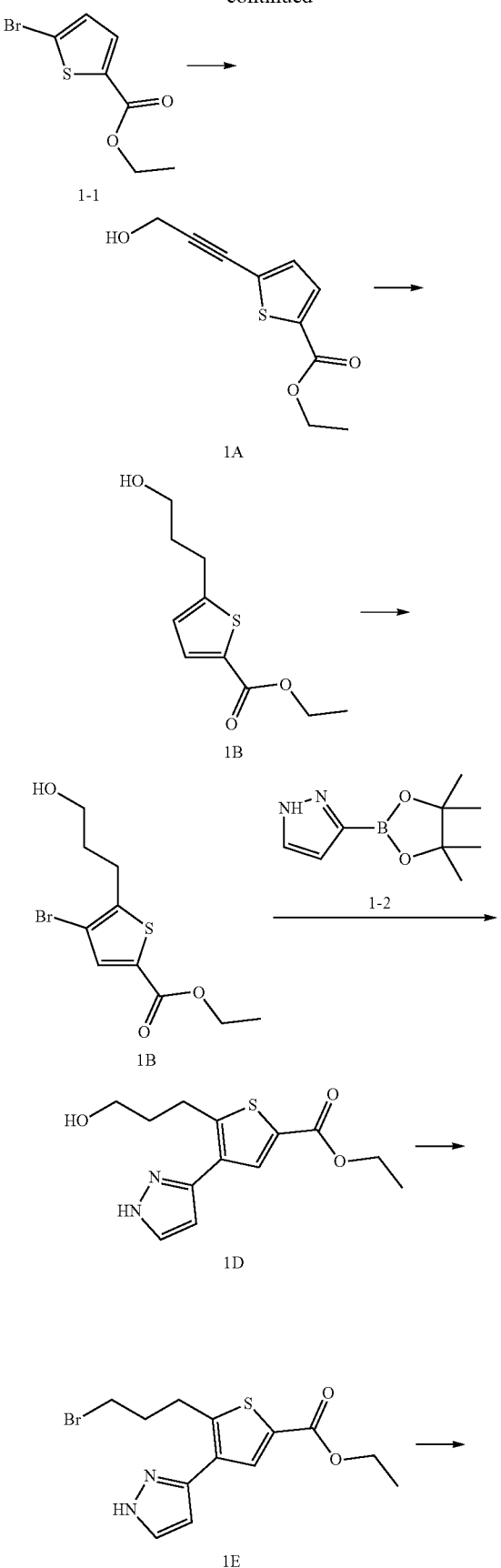

-continued

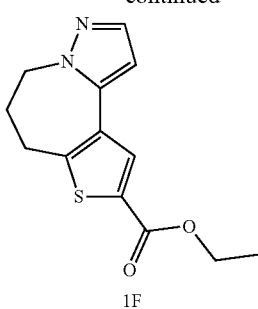

1F

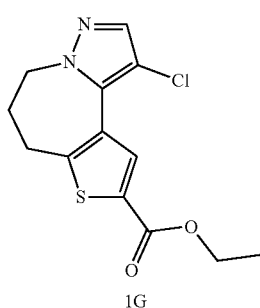

1G

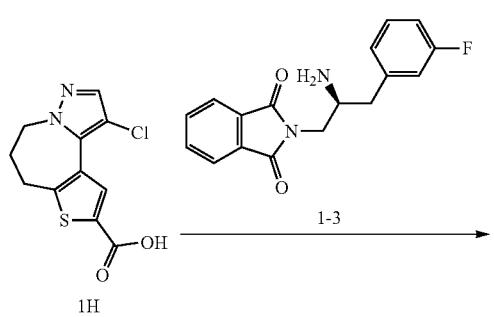

1H

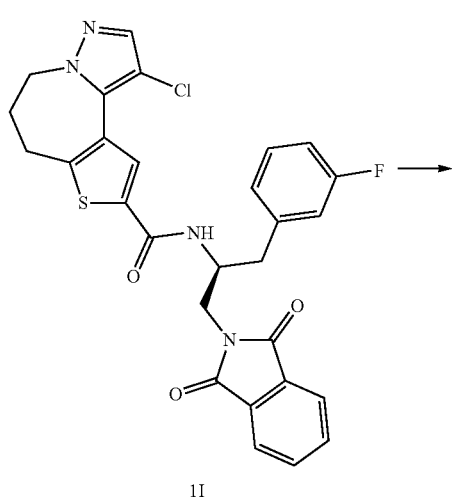

1I

-continued

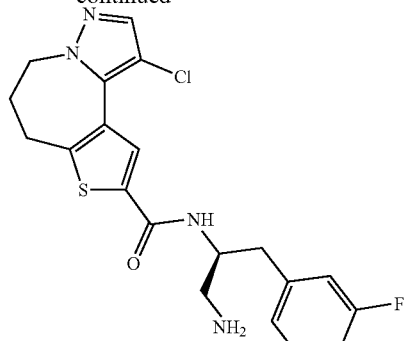

Embodiment 1

Intermediate 1A: ethyl 5-(3-hydroxyprop-1-yn-1-yl)thiophene-2-carboxylate

Ethyl 5-bromothiophene-2-carboxylate (30.00 g, 127.61 mmol), Pd(PPh$_3$)$_2$Cl$_2$ (4.48 g, 6.38 mmol) and cuprous iodide (1.22 g, 6.38 mmol) were suspended in triethylamine (109.50 g, 1.08 mol, 150.00 mL) at 20° C. under nitrogen, then propargyl alcohol (15.74 g, 280.74 mmol, 16.57 mL) was added dropwise to the above mixture. The reaction solution was reacted at 120° C. for 3 h, and the reaction was detected to be completed by thin layer chromatography. The reaction solution was cooled to room temperature, diluted with dichloromethane (350 mL), filtered, and the filtrate was washed with 2 mol/L hydrochloric acid (80 mL*2), dried over anhydrous magnesium sulfate, filtered and concentrated to dryness with rotary evaporator. The residue was purified by column chromatography to afford intermediate 1A (yellow oil liquid, 23.20 g, 85.72% yield). LCMS (ESI) m/z: 211 (M+1). $^1$H NMR (400 MHz, CHLOROFORM-d) δ ppm 1.39 (t, J=7.15 Hz, 3H), 1.78-1.88 (m, 1H), 4.30-4.42 (m, 2H), 4.50-4.59 (m, 2H), 7.13-7.20 (m, 1H), 7.61-7.70 (m, 1H).

Intermediate 1B: ethyl 5-(3-hydroxypropyl)thiophene-2-carboxylate

Dry palladium on carbon (3 g, 10%) was added to a solution of embodiment 1A (25.82 g, 121.76 mmol) in methanol (250 mL) under nitrogen. The suspension was charged three times with hydrogen and then hydrogenated at 25° C., 50 psi for 4 h. The palladium on carbon was filtered off and the mixture was evaporated, and concentrated to give intermediate 1B (yellow oily liquid, 23.10 g) used directly in the next step without further purification. LCMS (ESI) m/z: 215 (M+1). $^1$H NMR (400 MHz, CHLOROFORM-d) δ ppm 1.38 (t, J=7.15 Hz, 3H), 1.90-2.06 (m, 2H), 2.97 (t, J=7.59 Hz, 2H), 3.73 (s, 2H), 4.34 (d, J=7.03 Hz, 2H), 6.81-6.89 (m, 1H), 7.61-7.70 (m, 1H).

Intermediate 1C: ethyl 4-bromo-5-(3-hydroxypropyl)thiophene-2-carboxylate

Liquid bromine (14.13 g, 88.40 mmol) was added dropwise to the suspension of embodiment 1B (23 g, 88.40 mmol) and aluminum trichloride (35.36 g, 265.21 mmol) in dichloromethane (150 mL) at 0° C. under nitrogen while stirring. After the addition, the mixture was stirred at 25° C. for 2 h, then quenched with water (100 mL), extracted with ethyl acetate (800 mL), and organic phase was washed with saturated sodium thiosulfate (100 mL*2), dried over anhydrous sodium sulfate, filtered, concentrated, and the residue was purified by column chromatography to afford intermediate 1C (yellow oil, 26.01 g, 97.54% yield). LCMS (ESI) m/z: 295 (M+1). $^1$H NMR (400 MHz, CHLOROFORM-d) δ ppm 1.36 (t, J=7.15 Hz, 3H), 1.88-2.00 (m, 2H), 2.93 (t, J=7.59 Hz, 2H), 3.66-3.79 (m, 2H), 4.33 (d, J=7.03 Hz, 2H), 7.57-7.66 (s, 1H).

Intermediate 1D: ethyl 5-(3-hydroxypropyl)-4-(1H-pyrazol-3-yl) thiophene-2-carboxylate Intermediate 1C (18.52 g, 61.40 mmol), 3-(4,4,5,5-tetramethyl-1,3,2-dioxaborolan-2-yl)-1H-pyrazole (16.98 g, 73.68 mmol, hydrochloride), Pd(dppf)Cl$_2$ (4.49 g, 6.14 mmol) and cesium carbonate (40.01 g, 122.80 mmol) were stirred in the mixed solvent of DMF (100.00 mL) and water (20.00 mL) at 105° C. for 4 h. Then the reaction mixture was cooled to room temperature, adjusted to pH=5 with 2 N hydrochloric acid, and extracted with ethyl acetate (150 mL*2). The organic phases were combined, washed with saturated brine (60 mL*2), dried over anhydrous sodium sulfate, filtered, and concentrated. The residue was purified by column chromatography to afford intermediate 1D (yellow solid, 14.30 g, 67.54% yield). LCMS (ESI) m/z: 281 (M+1). $^1$H NMR (400 MHz, CHLOROFORM-d) δ ppm 1.24-1.40 (m, 3H), 1.84-1.97 (m, 2H), 2.78-2.93 (m, 2H), 3.22-3.26 (m, 1H), 3.53-3.68 (m, 2H), 4.19-4.34 (m, 2H), 6.27-6.41 (m, 1H), 7.49-7.60 (m, 2H), 7.72-7.98 (m, 1H).

Intermediate 1E: ethyl 5-(3-bromopropyl)-4-(1H-pyrazol-3-yl)thiophene-2-carboxylate A solution of triphenylphosphine (15.11 g, 57.60 mmol) in dichloromethane (100 mL) was added dropwise to a solution of the intermediate 1D (14.3 g, 44.31 mmol) and carbon tetrabromide (17.63 g, 44.31 mmol) in dichloromethane (100 mL) at 0° C. under nitrogen. The reaction was stirred at 0-8° C. for 3 h and then at 20° C. for another 9 h. The reaction was concentrated and the residue was purified by column chromatography to afford intermediate 1E (yellow solid, 15.00 g, 98.62% yield). LCMS (ESI) m/z: 343 (M+1). $^1$H NMR (400 MHz, CHLOROFORM-d) δ ppm 1.41 (t, J=7.09 Hz, 3H), 2.24-2.37 (m, 2H), 3.23-3.33 (m, 2H), 3.49 (s, 2H), 4.33-4.58 (m, 2H), 6.49-6.58 (m, 1H), 7.45-7.71 (m, 1H), 7.87-7.97 (m, 1H).

Intermediate 1F: ethyl 6,7-dihydro-5H-pyrazolo[1,5-a]thieno [3,2-c]azepine-9-carboxylate Caesium carbonate (27.38 g, 84.02 mmol) and potassium iodide (10.46 g, 63.02 mmol) were added to a solution of intermediate 1E (14.42 g, 42.01 mmol) in DMF (100.00 mL), and the mixture was stirred at 10-20° C. for 12 h. The mixture was quenched with water (50 mL), extracted with ethyl acetate (200 mL*2). The organic phase was washed with saturated brine (50 mL*2), dried over anhydrous sodium sulfate, filtered, and evaporated. The residue was purified by column chromatography to afford intermediate 1F (yellow solid, 6.10 g, 53.32% yield). LCMS (ESI) m/z: 263 (M+1). $^1$H NMR (400 MHz, CHLOROFORM-d) δ ppm 1.39 (t, J=7.09 Hz, 3H), 2.22-2.44 (m, 2H), 3.16-3.31 (m, 2H), 4.36 (d, J=7.15 Hz, 2H), 4.46-4.61 (m, 2H), 6.44-6.55 (m, 1H), 7.39-7.50 (m, 1H), 7.82-7.93 (s, 1H).

Intermediate 1G: ethyl 1-chloro-6,7-dihydro-5H-pyrazolo[1,5-a]thieno[3,2-c]azepine-9-carboxylate NCS (1.95 g, 14.60 mmol) was added to a solution of intermediate 1F (3.37 g, 12.85 mmol) in tetrahydrofuran (50 mL) at 20° C. The reaction mixture was stirred at 20° C. for 4 h, then quenched with water (10 mL), extracted with ethyl acetate (80 mL*2). The organic phase was washed with saturated brine (10 mL*2), dried over anhydrous sodium sulfate, filtered, and evaporated. The residue was purified by column chromatography to afford intermediate 1G (yellow solid, 3.2 g, 76.16% yield). LCMS (ESI) m/z: 297 (M+1). $^1$H NMR (400 MHz, CHLOROFORM-d) δ ppm 1.41 (t, J=7.15 Hz, 3H), 2.39 (d, J=5.77 Hz, 2H), 3.17 (t, J=6.96 Hz, 2H), 4.32-4.43 (m, 4H), 7.46 (s, 1H), 8.27 (s, 1H).

Intermediate 1H: 1-chloro-6,7-dihydro-5H-pyrazolo[1,5-a]thieno[3,2-c]azepine-9-carboxylic acid Lithium hydroxide monohydrate (3.4 g, 81.04 mmol) was added to a solution of the intermediate 1G (2.65 g, 8.10 mmol) in tetrahydrofuran (10 mL) and water (10 mL), then the mixture was reacted at 20-60° C. for 2 h. The reaction solution was cooled to room temperature, adjusted to pH=5 with 2 N hydrochloric acid, extracted with ethyl acetate (80 mL*2). The organic phase was washed with saturated brine (10 mL*2), dried over anhydrous sodium sulfate, filtered and concentrated to give intermediate 1H (yellow solid, 2.13 g, 96.98% yield). LCMS (ESI) m/z: 269 (M+1). $^1$H NMR (400 MHz, METHANOL-d4) δ ppm 2.29-2.42 (m, 1H), 3.23 (s, 1H), 4.34-4.43 (m, 1H), 7.48-7.55 (s, 1H), 8.22-8.26 (s, 1H).

Intermediate 1I: 1-chloro-N—((S)-1-(1,3-dioxoisoindolin-2-yl)-3-(3-fluorophenyl)propan-2-yl)-6,7-dihydro-5H-pyrazolo[1,5-a]thieno[3,2-c]azepine-9-carboxamide Diisopropylethylamine (3.92 g, 30.37 mmol, 5.3 mL) and T$_3$P (6.44 g, 10.12 mmol, 6.02 mL, ethyl acetate solution with 50% purity) were added to a solution of the intermediate 1H (1.7 g, 5.06 mmol) and (S)-2-(2-amino-3-(3-fluorophenyl)propyl)isoindoline-1,3-dione (2.03 g, 6.07 mmol, hydrochloride) in DMF (50 mL) at 0° C. under nitrogen. The mixture was reacted at 25° C. for 2 h, and 2N hydrochloric acid (80 mL) was added, then the mixture was extracted with ethyl acetate (150 mL*2). The organic phase was washed with saturated brine (50 mL*2), dried over anhydrous sodium sulfate, filtered, and concentrated. The residue was purified by column chromatography to afford intermediate 1I (white solid, 2.2 g, 74.88% yield). LCMS (ESI) m/z: 549 (M+1). $^1$H NMR (400 MHz, CHLOROFORM-d) δ ppm 2.30-2.40 (m, 2H), 2.93-3.03 (m, 1H), 3.17 (t, J=6.96 Hz, 3H), 3.80-3.88 (m, 1H), 3.89-3.96 (m, 1H), 4.33-4.42 (m, 2H), 4.54-4.64 (m, 1H), 6.86-6.91 (m, 1H), 6.94-7.01 (m, 1H), 7.01-7.07 (m, 1H), 7.09-7.14 (m, 1H), 7.30-7.35 (m, 1H), 7.46-7.50 (m, 1H), 7.72-7.76 (m, 2H), 7.83-7.89 (m, 2H), 7.97-8.00 (m, 1H).

Preparation of Embodiment 1

Hydrazine hydrate (11.95 g, 238.79 mmol) was added to a solution of the intermediate 11 (4.60 g, 7.96 mmol) in tetrahydrofuran (50 mL), and the mixture was stirred at 20-60° C. for 3 h, then the solvent was removed in vacuo. The residue was purified by preparative HPLC to give embodiment 1 (2.8 g, 75.25% yield, 100% ee, formate). LCMS (ESI) m/z: 419 (M+1). $^1$H NMR (400 MHz, METHANOL-d4) δ ppm 2.30-2.38 (m, 2H), 2.94-3.07 (m, 1H), 3.09-3.24 (m, 3H), 4.28-4.40 (m, 1H), 4.48-4.57 (m, 1H), 6.94-7.00 (m, 1H), 7.07 (d, J=9.91 Hz, 1H), 7.10-7.16 (m, 1H), 7.27-7.39 (m, 1H), 7.51 (s, 1H), 8.14 (s, 1H), 8.48-8.60 (s, 1H).

Embodiment 2

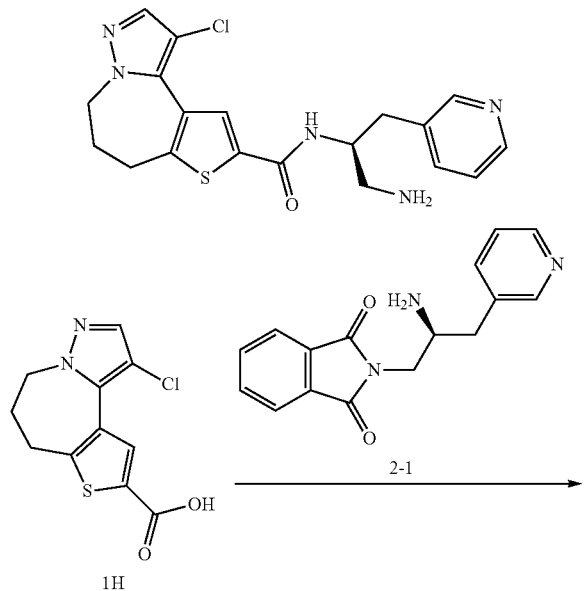

Intermediate 2A: 1-chloro-N—((S)-1-(1,3-dioxoisoindolin-2-yl)-3-(pyridin-3-yl)propan-2-yl)-6,7-dihydro-5H-pyrazolo[1,5-a]thieno[3,2-c]azepine-9-carboxamide Intermediate 2A was prepared according to the method as described in the preparation of intermediate 11. LCMS (ESI) m/z: 532 (M+1). $^1$H NMR (400 MHz, DMSO-d6) δ ppm 2.16 (d, J=4.64 Hz, 2H), 2.83-3.01 (m, 2H), 3.08 (t, J=6.84 Hz, 2H), 3.79-3.89 (m, 2H), 4.28-4.33 (m, 2H), 4.41-4.49 (m, 1H), 7.26 (dd, J=7.84, 4.83 Hz, 1H), 7.61 (s, 1H), 7.67-7.73 (m, 1H), 7.85 (d, J=3.01 Hz, 3H), 8.00 (s, 1H), 8.31-8.40 (m, 1H), 8.48 (s, 1H), 8.53-8.58 (m, 1H), 8.61-8.65 (m, 1H).

Preparation of Embodiment 2

Prepare according to the method as described in embodiment 1. LCMS (ESI) m/z: 402 (M+1). $^1$H NMR (400 MHz, DMSO-d6) δ ppm 2.24-2.39 (m, 2H), 2.95-3.03 (m, 1H), 3.09 (d, J=4.89 Hz, 1H), 3.17 (t, J=6.96 Hz, 3H), 3.25-3.31 (m, 1H), 4.27-4.40 (m, 2H), 4.56 (br. s., 1H), 7.39 (dd, J=7.72, 4.96 Hz, 1H), 7.51 (s, 1H), 7.81 (d, J=7.78 Hz, 1H), 8.13 (s, 1H), 8.41 (d, J=4.64 Hz, 3H), 8.49 (s, 1H).

Embodiment 3

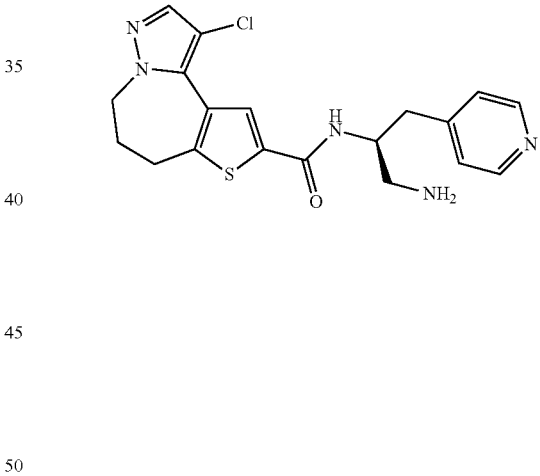

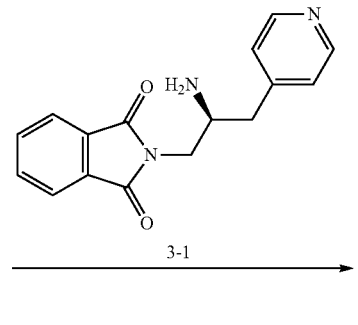

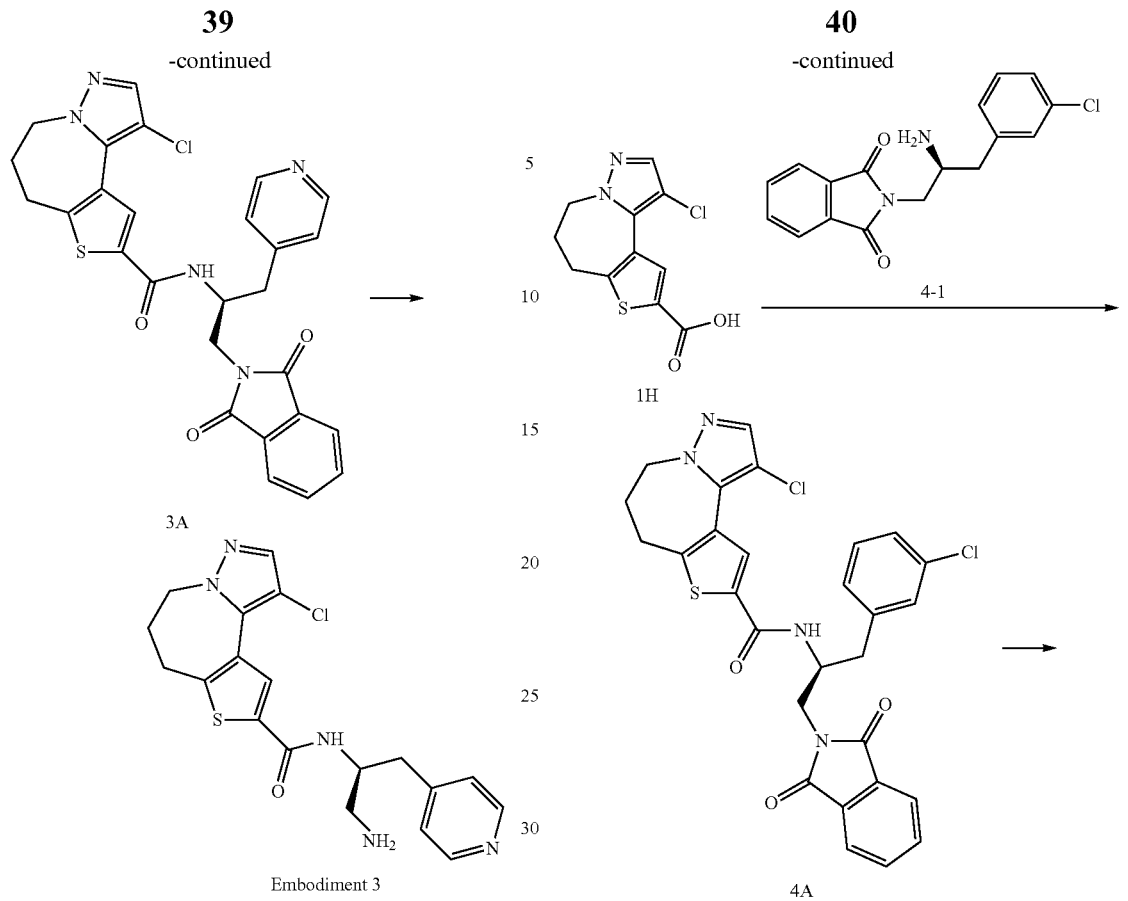

Intermediate 3A: 1-chloro-N—((S)-1-(1,3-dioxoisoindolin-2-yl)-3-(pyridin-4-yl)propan-2-yl)-6,7-dihydro-5H-pyrazolo[1,5-a]thieno [3,2-c]azepine-9-carboxamide Prepare according to the method as described in the preparation of intermediate 11. LCMS (ESI) m/z: 532. 1H NMR (400 MHz, DMSO-d6) δ ppm 2.17 (d, J=4.39 Hz, 2H), 2.82-3.04 (m, 2H), 3.09 (t, J=6.84 Hz, 2H), 3.71-4.04 (m, 2H), 4.18-4.40 (m, 2H), 4.41-4.67 (m, 1H), 7.29 (d, J=5.52 Hz, 2H), 7.61 (s, 1H), 7.85 (d, J=2.64 Hz, 4H), 7.98 (s, 1H), 8.41 (d, J=5.40 Hz, 2H), 8.53 (d, J=9.03 Hz, 1H).

Preparation of Embodiment 3

Prepare according to the method as described in embodiment 1. LCMS (ESI) m/z: 402 (M+1). ¹H NMR (400 MHz, METHANOL-d4) δ ppm 2.27-2.38 (m, 2H), 2.88-3.29 (m, 6H), 4.33 (t, J=5.40 Hz, 2H), 4.57-4.69 (m, 1H), 7.40 (d, J=5.14 Hz, 2H), 7.51 (s, 1H), 8.12 (s, 1H), 8.40 (br. s., 1H), 8.43-8.48 (m, 2H).

Embodiment 4

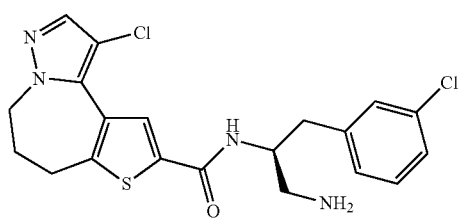

Intermediate 4A: 1-chloro-N—((S)-1-(3-chlorophenyl)-3-(1,3-dioxoisoindolin-2-yl)propan-2-yl)-6,7-dihydro-5H-pyrazolo[1,5-a]thieno [3,2-c]azepine-9-carboxamide Prepare according to the method as described in the preparation of intermediate 11. LCMS (ESI) m/z: 565.

Preparation of Embodiment 4

Hydrazine hydrate (108 mg, 2.12 mmol) was added to a solution of the intermediate 4A (60 mg crude) in THF (5 mL) and methanol (5 mL), and the mixture was stirred at 15° C. for 12 h, and the solution was removed in vacuo. The residue was purified by preparative HPLC to give embodiment 4 (30 mg, 64.16% yield). LCMS (ESI) m/z: 435 (M+1). ¹H NMR (400 MHz, DMSO-d6) δ ppm 2.20 (d, J=4.52 Hz, 2H), 2.91 (br. s., 4H), 3.11 (t, J=6.78 Hz, 2H), 4.29 (d, J=4.39 Hz, 1H), 4.42-4.51 (m, 2H), 7.13-7.34 (m, 3H), 7.36 (s, 1H), 7.61 (s, 1H), 8.15 (s, 1H), 8.40 (br. s., 1H), 9.07 (d, J=7.15 Hz, 1H).

Embodiment 5

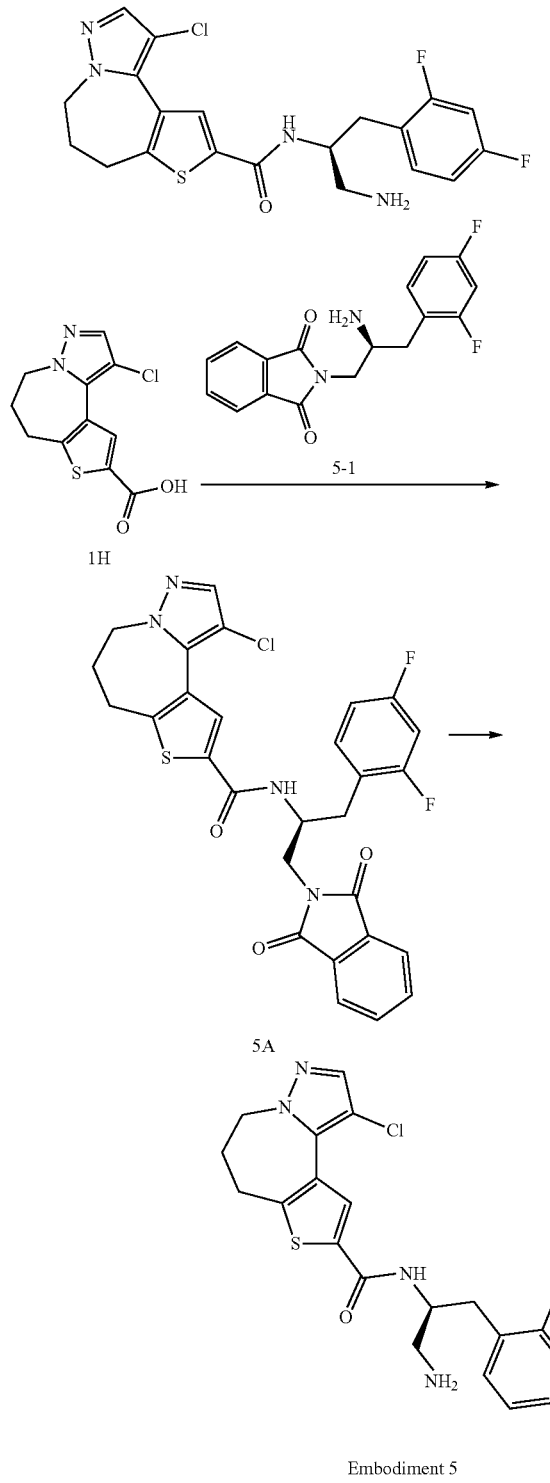

Intermediate 5A: 1-chloro-N—((S)-1-(2,4-difluoro-phenyl)-3-(1,3-dioxoisoindolin-2-yl)propan-2-yl)-6,7-dihydro-5H-pyrazolo[1,5-a]thieno[3,2-c]azepine-9-carboxamide Prepare according to the method as described in the preparation of intermediate 11. LCMS (ESI) m/z: 567.

Preparation of Embodiment 5

Prepare according to the method as described in embodiment 4. LCMS (ESI) m/z: 437 (M+1). $^1$H NMR (400 MHz, DMSO-d6) δ ppm 2.21 (t, J=6.46 Hz, 2H), 2.68-3.06 (m, 5H), 3.11 (t, J=6.90 Hz, 2H), 4.27-4.31 (m, 2H), 6.99 (td, J=8.44, 2.32 Hz, 1H), 7.17 (td, J=9.88, 2.45 Hz, 1H), 7.31-7.40 (m, 1H), 7.61 (s, 1H), 8.10 (s, 1H), 8.37 (br. s., 1H), 8.79 (d, J=8.28 Hz, 1H).

Embodiment 6

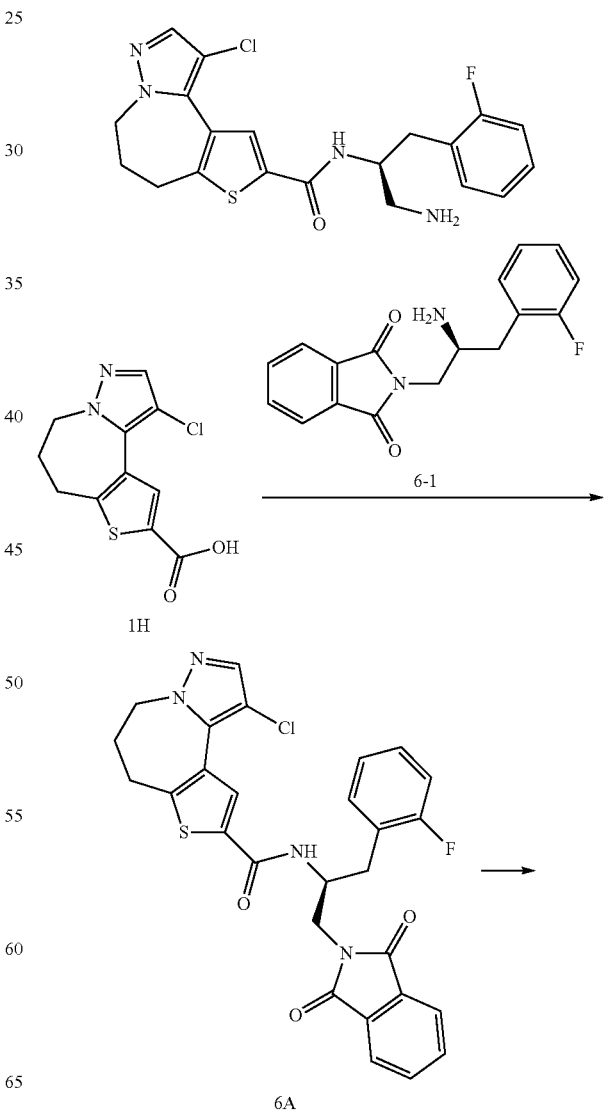

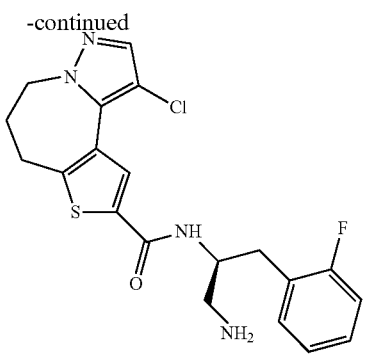

Embodiment 6

Intermediate 6A: 1-chloro-N—((S)-1-(1,3-dioxoisoindolin-2-yl)-3-(2-fluorophenyl)propan-2-yl)-6,7-dihydro-5H-pyrazolo[1,5-a]thieno [3,2-c]azepine-9-carboxamide Prepare according to the method as described in intermediate 11. LCMS (ESI) m/z: 549. 1H NMR (400 MHz, DMSO-d6) δ ppm 2.11-2.23 (m, 2H), 2.82-2.97 (m, 1H), 3.00-3.16 (m, 3H), 3.82 (d, J=6.11 Hz, 2H), 4.29 (t, J=5.44 Hz, 2H), 4.43-4.69 (m, 1H), 7.01-7.17 (m, 2H), 7.18-7.27 (m, 1H), 7.37 (t, J=7.09 Hz, 1H), 7.60 (s, 1H), 7.84 (d, J=1.59 Hz, 4H), 7.99 (s, 1H), 8.55 (d, J=9.17 Hz, 1H).

Preparation of Embodiment 6

Prepare according to the method as described in embodiment 4. LCMS (ESI) m/z: 419 (M+1). ¹H NMR (400 MHz, METHANOL-d4) δ ppm 2.33 (t, J=6.46 Hz, 2H), 3.02 (d, J=9.03 Hz, 1H), 3.09 (d, J=5.40 Hz, 1H), 3.14-3.23 (m, 3H), 3.24 (d, J=3.39 Hz, 1H), 4.18-4.44 (m, 2H), 4.50-4.69 (m, 1H), 6.97-7.17 (m, 2H), 7.20-7.40 (m, 2H), 7.51 (s, 1H), 8.15 (s, 1H), 8.49 (br. s., 1H).

Embodiment 7

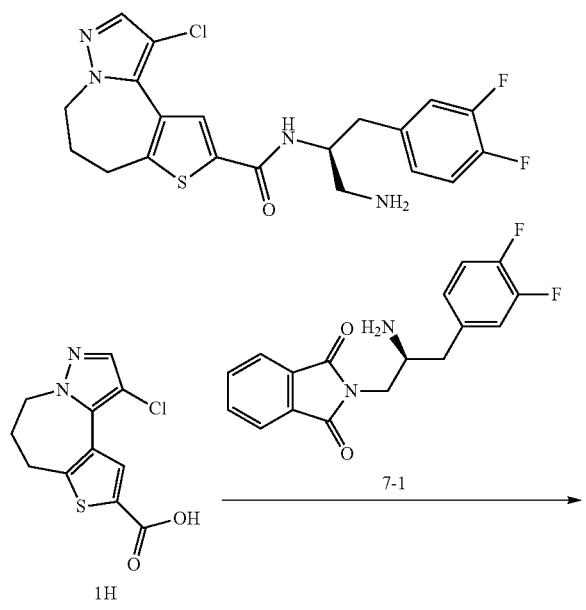

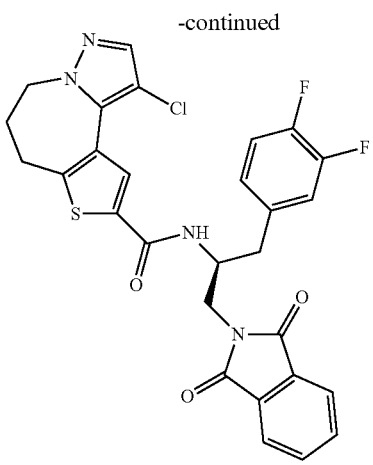

7A

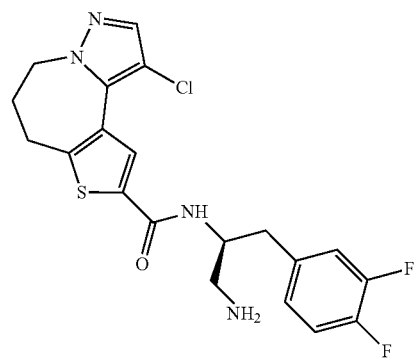

Embodiment 7

Intermediate 7A: 1-chloro-N—((S)-1-(3,4-difluorophenyl)-3-(1,3-dioxoisoindolin-2-yl)propan-2-yl)-6,7-dihydro-5H-pyrazolo[1,5-a]thieno[3,2-c]azepine-9-carboxamide Prepare according to the method as described in intermediate 11. LCMS (ESI) m/z: 567. ¹H NMR (400 MHz, DMSO-d6) δ ppm 2.12-2.27 (m, 2H), 2.88 (d, J=10.79 Hz, 1H), 3.00 (dd, J=13.36, 3.95 Hz, 1H), 3.10 (t, J=6.78 Hz, 2H), 3.77-3.87 (m, 2H), 4.31 (t, J=5.40 Hz, 2H), 4.40-4.47 (m, 1H), 7.13 (br. s., 1H), 7.26-7.38 (m, 2H), 7.61 (s, 1H), 7.85 (d, J=2.38 Hz, 4H), 7.99 (s, 1H), 8.48 (d, J=8.91 Hz, 1H).

Preparation of Embodiment 7

Prepare according to the method as described in embodiment 4. LCMS (ESI) m/z: 437 (M+1). ¹H NMR (400 MHz, METHANOL-d4) δ ppm 2.27-2.41 (m, 2H), 2.87-3.06 (m, 2H), 3.19 (s, 4H), 4.34 (dd, J=4.45, 1.82 Hz, 2H), 4.44-4.63 (m, 1H), 7.07-7.28 (m, 3H), 7.51 (s, 1H), 8.14 (s, 1H), 8.52 (br. s., 1H).

Embodiment 8

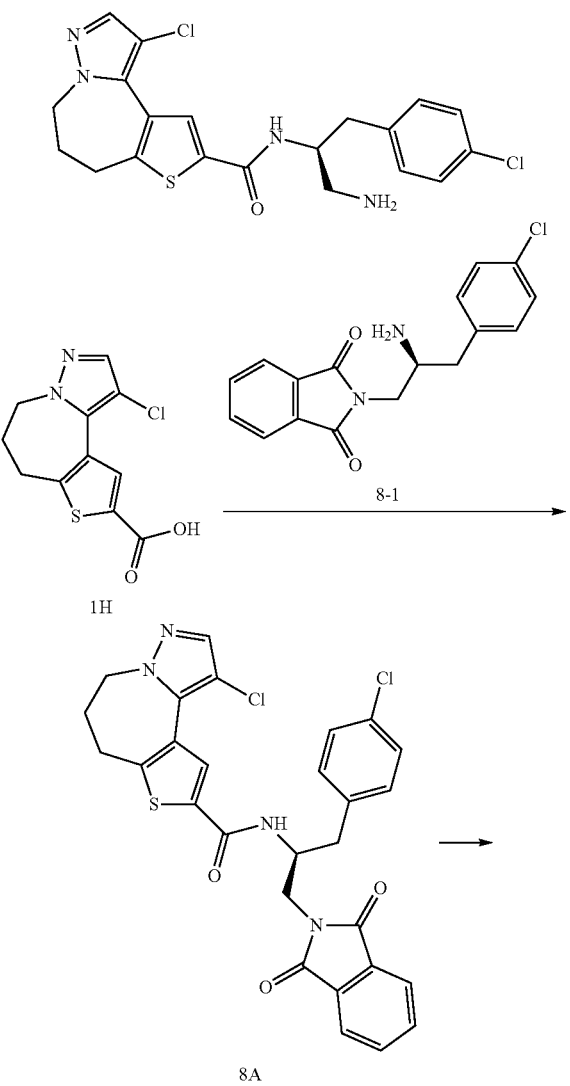

Intermediate 8A: 1-chloro-N—((S)-1-(4-chlorophenyl)-3-(1,3-dioxoisoindolin-2-yl)propan-2-yl)-6,7-dihydro-5H-pyrazolo[1,5a]thieno[3,2-c]azepine-9-carboxamide Prepare according to the method as described in intermediate 11. LCMS (ESI) m/z: 565.

Preparation of Embodiment 8

Prepare according to the method as described in embodiment 4. LCMS (ESI) m/z: 435 (M+1). $^1$H NMR (400 MHz, METHANOL-d4) δ ppm 2.34 (t, J=6.34 Hz, 2H), 2.89-3.05 (m, 2H), 3.19 (t, J=7.03 Hz, 4H), 4.34 (dt, J=6.21, 3.92 Hz, 2H), 4.45-4.56 (m, 1H), 7.11-7.43 (m, 4H), 7.51 (s, 1H), 8.13 (s, 1H), 8.43-8.63 (m, 1H).

Embodiment 9

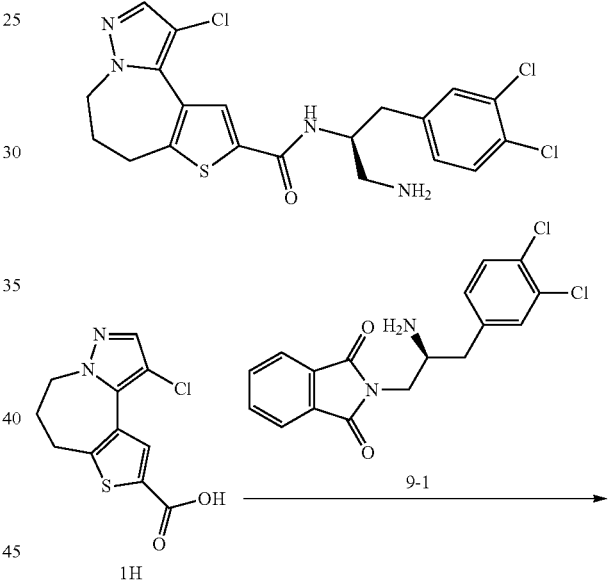

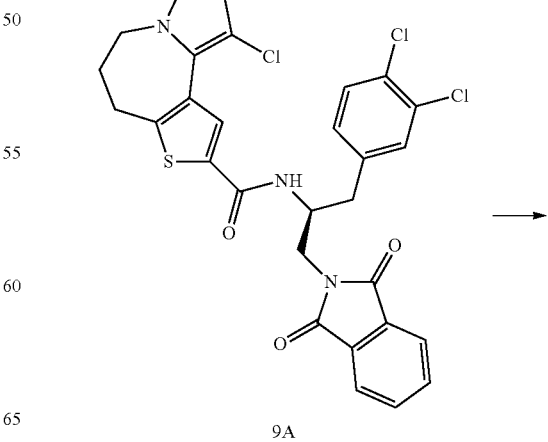

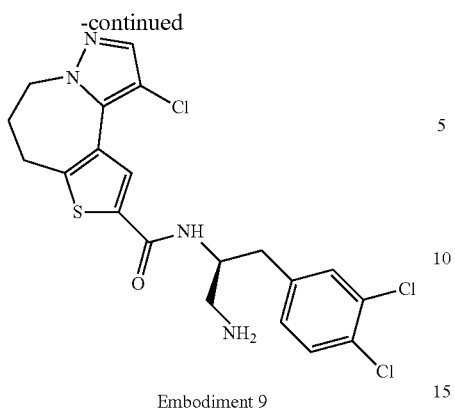

Embodiment 9

Intermediate 9A: 1-chloro-N—((S)-1-(3,4-dichlorophenyl)-3-(1,3-dioxoisoindolin-2-yl)propan-2-yl)-6,7-dihydro-5H-pyrazolo[1,5a]thieno[3,2-c]azepine-9-carboxamide Prepare according to the method as described in intermediate 11. LCMS (ESI) m/z: 599. $^1$H NMR (400 MHz, DMSO-d6) δ ppm 2.13-2.21 (m, 2H), 2.83-2.90 (m, 1H), 3.00 (d, J=4.16 Hz, 1H), 3.06-3.14 (m, 2H), 3.75-3.88 (m, 2H), 4.31 (t, J=5.56 Hz, 2H), 4.44 (d, J=3.79 Hz, 1H), 7.25-7.30 (m, 1H), 7.48 (d, J=8.19 Hz, 1H), 7.57 (d, J=1.83 Hz, 1H), 7.61 (s, 1H), 7.84 (d, J=2.57 Hz, 4H), 7.99 (s, 1H), 8.50 (d, J=9.05 Hz, 1H).

Preparation of Embodiment 9

Prepare according to the method as described in embodiment 4. LCMS (ESI) m/z: 469 (M+1). $^1$H NMR (400 MHz, METHANOL-d4) δ ppm 2.29-2.39 (m, 2H), 2.94 (d, J=9.54 Hz, 1H), 2.98-3.06 (m, 1H), 3.11-3.28 (m, 4H), 4.34 (ddd, J=7.53, 3.58, 2.45 Hz, 2H), 4.46-4.56 (m, 1H), 7.23 (dd, J=8.16, 1.63 Hz, 1H), 7.44 (d, J=8.28 Hz, 1H), 7.49 (d, J=1.63 Hz, 1H), 7.51 (s, 1H), 8.14 (s, 1H), 8.53 (s, 1H).

Embodiment 10

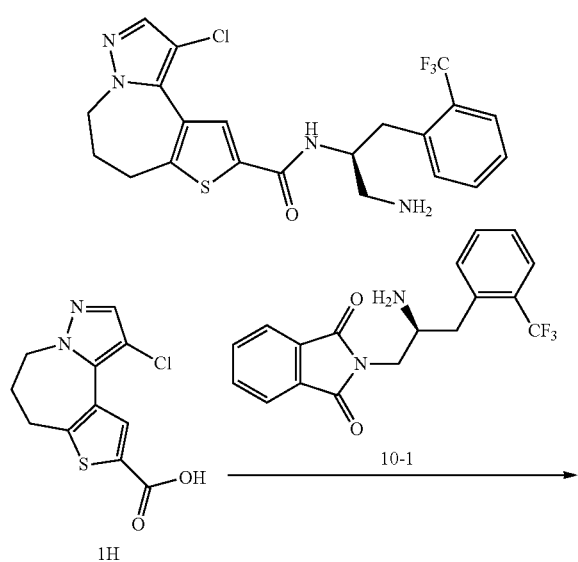

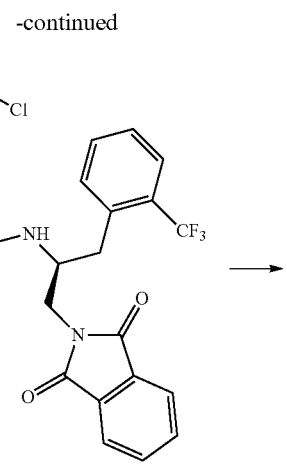

10A

Embodiment 10

Intermediate 10A: 1-chloro-N—((S)-1-(1,3-dioxoisoindolin-2-yl)-3-(2-(trifluoromethyl)phenyl)propan-2-yl)-6,7-dihydro-5H-pyrazolo[1,5-a]thieno[3,2-c]azepine-9-carboxamide Prepare according to the method as described in intermediate 11. LCMS (ESI) m/z: 599. $^1$H NMR (400 MHz, DMSO-d6) δ ppm 2.17 (d, J=6.15 Hz, 2H), 3.04-3.19 (m, 4H), 3.77-3.86 (m, 2H), 4.31 (t, J=5.40 Hz, 2H), 4.51 (d, J=3.26 Hz, 1H), 7.40 (s, 1H), 7.53 (d, J=10.92 Hz, 2H), 7.62 (s, 1H), 7.66-7.70 (m, 1H), 7.82-7.88 (m, 4H), 8.06 (s, 1H), 8.62 (d, J=9.29 Hz, 1H).

Preparation of Embodiment 10

Prepare according to the method as described in embodiment 1. LCMS (ESI) m/z: 469 (M+1). $^1$H NMR (400 MHz, METHANOL-d4) δ ppm 2.21-2.52 (m, 2H), 3.06-3.29 (m, 6H), 4.34 (d, J=5.75 Hz, 2H), 4.64 (br. s., 1H), 7.35-7.47 (m, 1H), 7.47-7.65 (m, 3H), 7.66-7.77 (m, 1H), 8.19 (s, 1H), 8.52 (br. s., 1H).

Embodiment 11

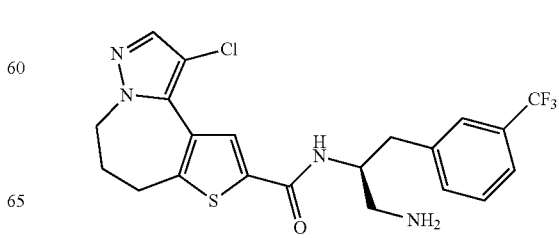

49

-continued

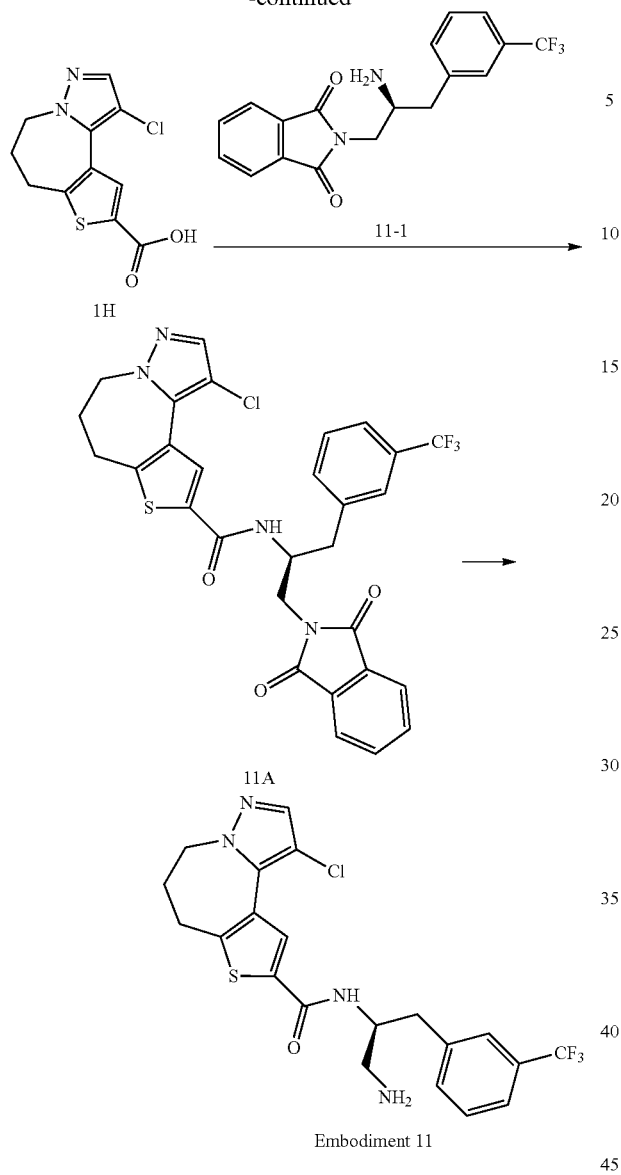

11A

Embodiment 11

Intermediate 11A: 1-chloro-N—((S)-1-(1,3-dioxoisoindolin-2-yl)-3-(3-(trifluoromethyl)phenyl)propan-2-yl)-6,7-dihydro-5H-pyrazolo[1,5-a]thieno[3,2-c]azepine-9-carboxamide Prepare according to the method as described in intermediate 11. LCMS (ESI) m/z: 599. $^1$H NMR (400 MHz, DMSO-d6) δ ppm 2.10-2.23 (m, 2H), 2.92-3.03 (m, 1H), 3.09 (t, J=6.84 Hz, 3H), 3.72-3.96 (m, 2H), 4.30 (t, J=5.52 Hz, 2H), 4.48 (d, J=4.39 Hz, 1H), 7.42-7.54 (m, 2H), 7.54-7.64 (m, 2H), 7.66 (s, 1H), 7.80-7.91 (m, 4H), 7.99 (s, 1H), 8.47-8.61 (m, 1H).

Preparation of Embodiment 11

Prepare according to the method as described in embodiment 1. LCMS (ESI) m/z: 469 (M+1). 1H NMR (400 MHz, METHANOL-d4) δ ppm 2.15-2.54 (m, 2H), 2.99-3.30 (m, 6H), 4.20-4.41 (m, 2H), 4.49-4.62 (m, 1H), 7.29-7.80 (m, 5H), 8.13 (s, 1H), 8.44-8.60 (m, 1H).

50

Embodiment 12

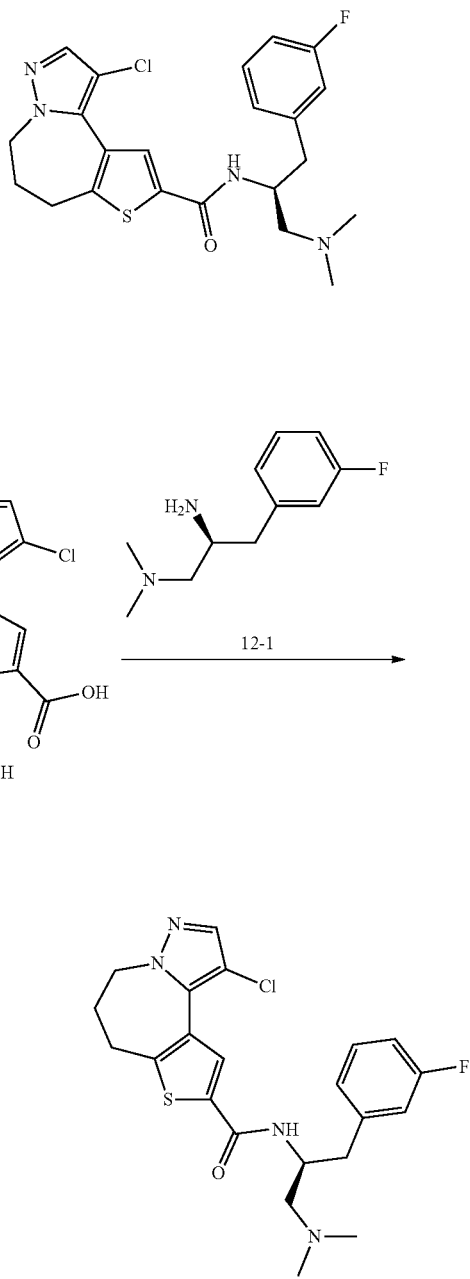

Embodiment 12

Preparation of Embodiment 12

Prepare according to the method as described in embodiment 1. LCMS (ESI) m/z: 447 (M+1). $^1$H NMR (400 MHz, METHANOL-d4) δ ppm 2.34 (t, J=6.59 Hz, 2H), 2.40 (s, 6H), 2.57 (br. s., 1H), 2.76 (d, J=10.42 Hz, 1H), 2.85 (dd, J=13.80, 8.66 Hz, 1H), 2.96-3.03 (m, 1H), 3.18 (t, J=6.96 Hz, 2H), 4.25-4.40 (m, 2H), 4.46-4.56 (m, 1H), 6.89-6.96 (m, 1H), 7.03 (d, J=10.04 Hz, 1H), 7.09 (d, J=7.78 Hz, 1H), 7.28 (td, J=7.87, 6.21 Hz, 1H), 7.50 (s, 1H), 8.11 (s, 1H).

Embodiment 13

Embodiment 14

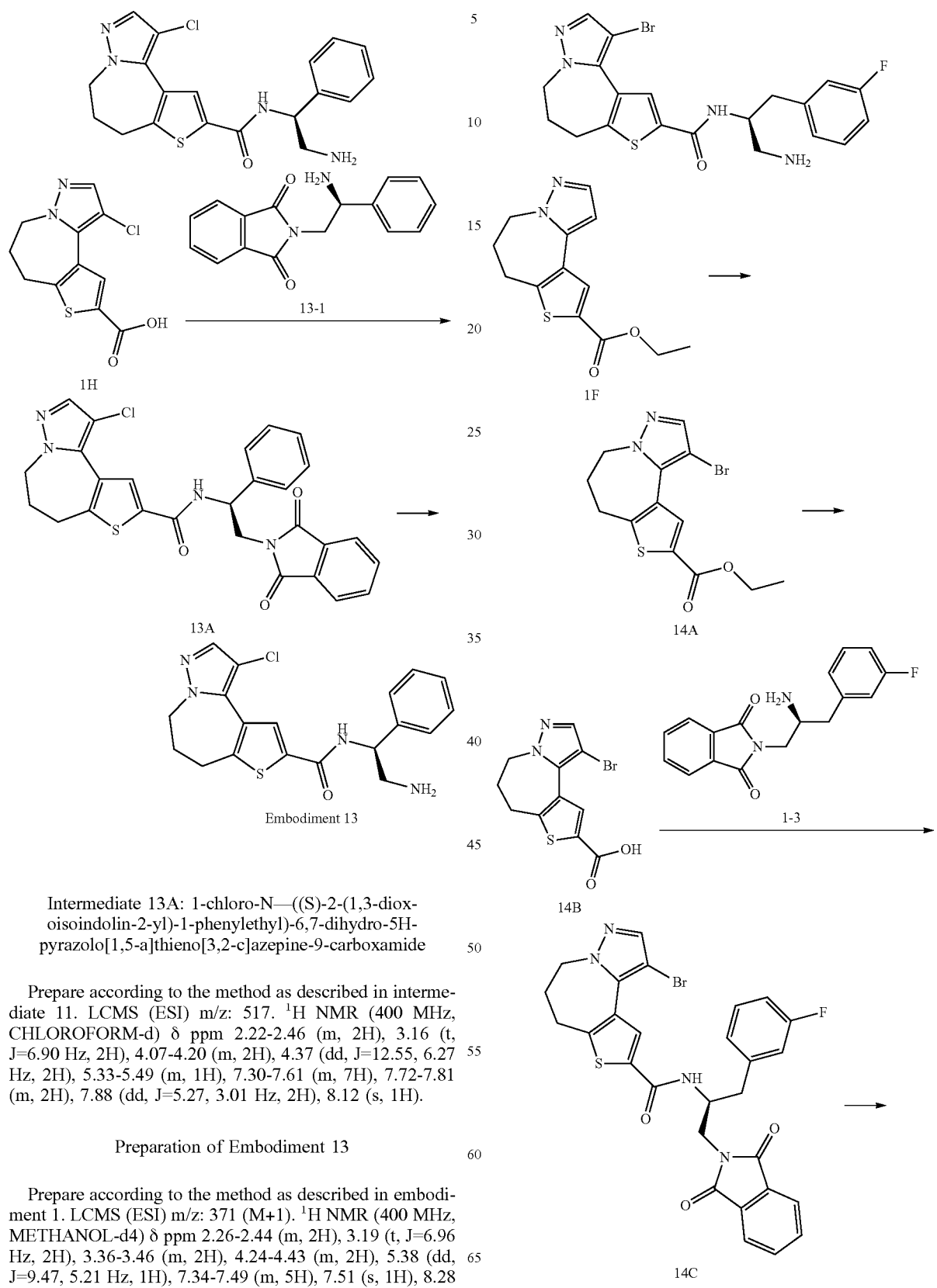

Intermediate 13A: 1-chloro-N—((S)-2-(1,3-dioxoisoindolin-2-yl)-1-phenylethyl)-6,7-dihydro-5H-pyrazolo[1,5-a]thieno[3,2-c]azepine-9-carboxamide Prepare according to the method as described in intermediate 11. LCMS (ESI) m/z: 517. $^1$H NMR (400 MHz, CHLOROFORM-d) δ ppm 2.22-2.46 (m, 2H), 3.16 (t, J=6.90 Hz, 2H), 4.07-4.20 (m, 2H), 4.37 (dd, J=12.55, 6.27 Hz, 2H), 5.33-5.49 (m, 1H), 7.30-7.61 (m, 7H), 7.72-7.81 (m, 2H), 7.88 (dd, J=5.27, 3.01 Hz, 2H), 8.12 (s, 1H).

Preparation of Embodiment 13

Prepare according to the method as described in embodiment 1. LCMS (ESI) m/z: 371 (M+1). $^1$H NMR (400 MHz, METHANOL-d4) δ ppm 2.26-2.44 (m, 2H), 3.19 (t, J=6.96 Hz, 2H), 3.36-3.46 (m, 2H), 4.24-4.43 (m, 2H), 5.38 (dd, J=9.47, 5.21 Hz, 1H), 7.34-7.49 (m, 5H), 7.51 (s, 1H), 8.28 (s, 1H), 8.54 (br. s., 1H).

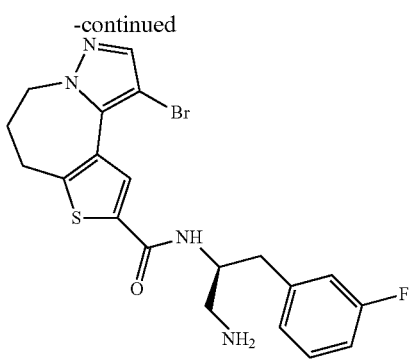

Embodiment 14

Intermediate 14A: ethyl 1-bromo-6,7-dihydro-5H-pyrazolo[1,5-a]thieno[3,2-c]azepine-9-carboxylate NBS (36 mg, 200.13 μmol) was added to a solution of intermediate 1F (50 mg, 190.65 μmol) in tetrahydrofuran (5 mL). The reaction mixture was stirred at 15° C. for 16 h, then ethyl acetate (15 mL) was added. The organic phase was washed with saturated brine (20 mL*3), dried over anhydrous sodium sulfate, filtered and concentrated to give the title compound (white solid crude, 63 mg). LCMS (ESI) m/z: 341 (M+1). $^1$H NMR (400 MHz, CHLOROFORM-d) δ ppm 1.40 (t, J=7.09 Hz, 3H), 2.34-2.46 (m, 2H), 3.10 (s, 2H), 4.30-4.35 (m, 2H), 4.35-4.42 (m, 2H), 7.49 (s, 1H), 8.24 (s, 1H).

Intermediate 14B: 1-bromo-6,7-dihydro-5H-pyrazolo[1,5-a]thieno[3,2-c]azepine-9-carboxylic acid Sodium hydroxide (30 mg, 738.52 μmol) was added to a solution of intermediate 14A (66 mg, 184.63 μmol) in methanol (3 mL) and water (1 mL), then the mixture was reacted at 50° C. for 16 h. The methanol was evaporated under reduced pressure, then the residue was adjusted to pH=4-5 with 1 N hydrochloric acid, extracted with ethyl acetate (20 mL*2), and the organic phase was washed with saturated brine solution (10 mL), dried over anhydrous sodium sulfate, filtered and concentrated to give the title compound (yellow solid, 80 mg), which was used directly in the next step without further purification. LCMS (ESI) m/z: 313 (M+1).

Intermediate 14C: (S)-1-bromo-N-(1-(1,3-dioxoisoindolin-2-yl)-3-(3-fluorophenyl)propan-2-yl)-6,7-dihydro-5H-pyrazolo[1,5-a]thieno [3,2-c]azepine-9-carboxamide Diisopropylethylamine (99 mg, 766.35 μmol), TBTU (123 mg, 383.18 μmol) and (S)-2-(2-amino-3-(3-fluorophenyl)propyl)isoindoline-1,3-dione (94 mg, 281 μmol) were added to a solution of intermediate 14B (80 mg, 255.45 μmol) in DMF (5 mL) at −20° C. under nitrogen. The mixture was reacted at −20-15° C. for 2 h, ethyl acetate (20 mL) was added, and the mixture was washed with saturated ammonium chloride (50 mL*3) and brine (50 mL*3). The organic phase was dried over anhydrous sodium sulfate, filtered and concentrated to give the title compound (white solid, 131 mg). LCMS (ESI) m/z: 593 (M+1).

Preparation of Embodiment 14

Hydrated hydrazine (226 mg, 4.41 mmol) was added to a mixed solution of intermediate 14C (131 mg crude) in THF (3 mL) and methanol (3 mL), and the mixture was stirred at 15° C. for 16 h, then the solution was removed in vacuo. The residue was purified by preparative HPLC to give the title compound (44 mg, 39.1% yield, 100% ee). LCMS (ESI) m/z: 463 (M+1). $^1$H NMR (400 MHz, METHANOL-d4) δ ppm 2.30-2.44 (m, 2H), 2.93-3.07 (m, 2H), 3.08-3.27 (m, 4H), 4.23-4.41 (m, 2H), 4.47-4.60 (m, 1H), 6.92-7.02 (m, 1H), 7.04-7.17 (m, 2H), 7.27-7.39 (m, 1H), 7.54 (s, 1H), 8.09-8.17 (m, 1H), 8.48-8.52 (m, 1H).

Embodiment 15

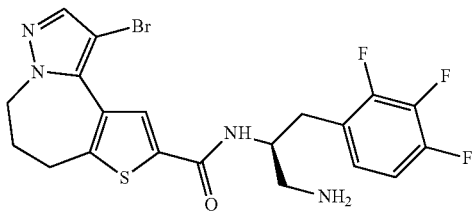

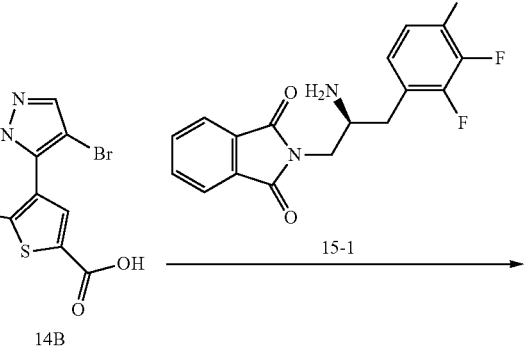

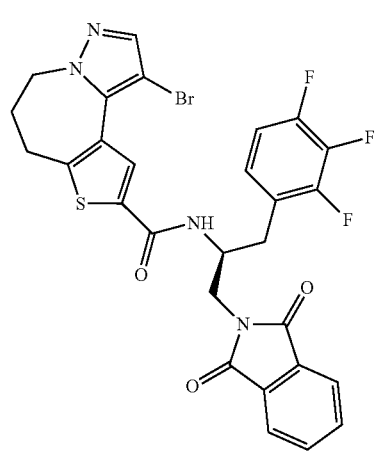

15A

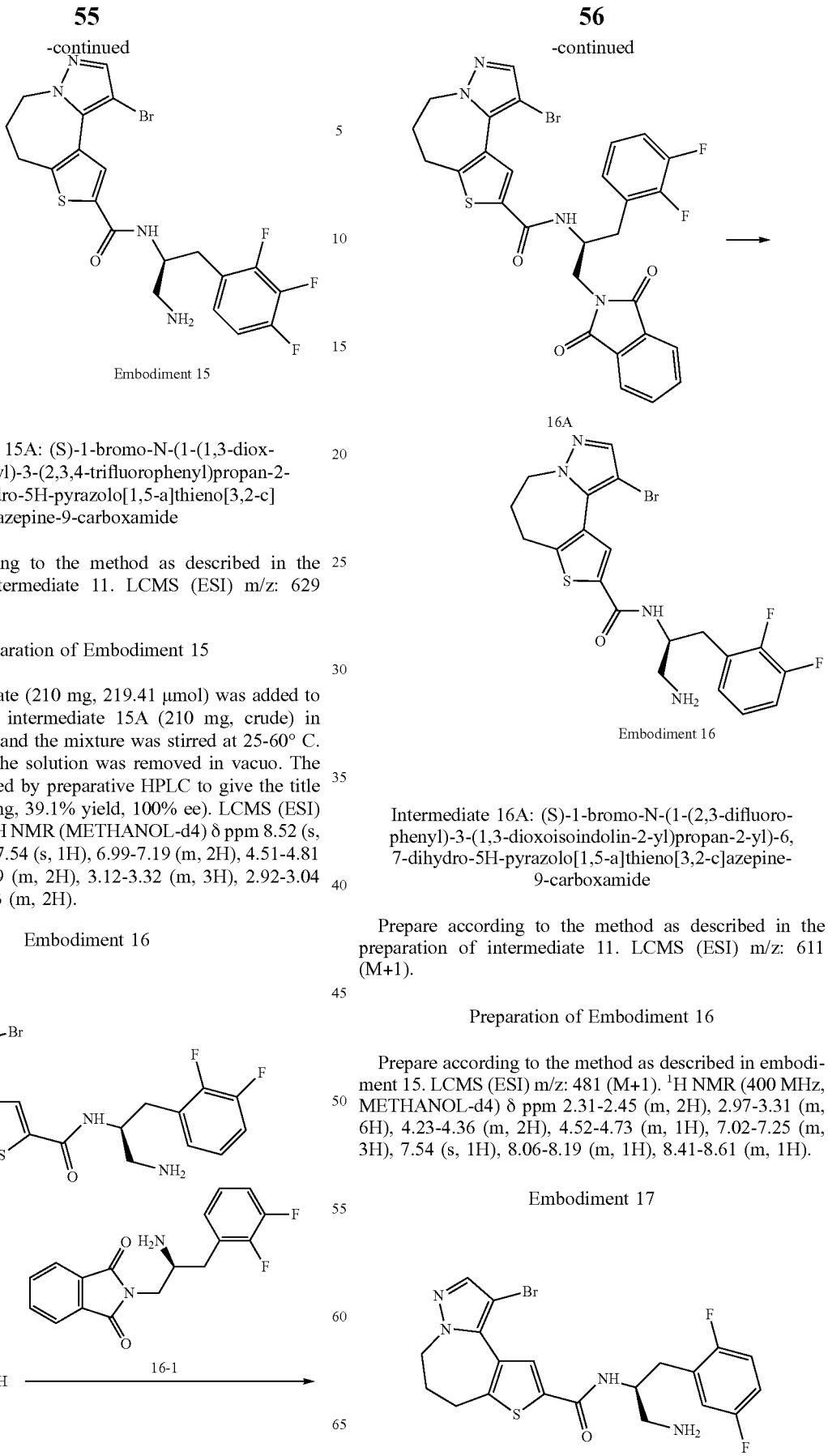

Embodiment 15

Intermediate 15A: (S)-1-bromo-N-(1-(1,3-dioxoisoindolin-2-yl)-3-(2,3,4-trifluorophenyl)propan-2-yl)-6,7-dihydro-5H-pyrazolo[1,5-a]thieno[3,2-c]azepine-9-carboxamide Prepare according to the method as described in the preparation of intermediate 11. LCMS (ESI) m/z: 629 (M+1).

Preparation of Embodiment 15

Hydrazine hydrate (210 mg, 219.41 μmol) was added to a solution of the intermediate 15A (210 mg, crude) in menthol (10 mL), and the mixture was stirred at 25-60° C. for 15 min, then the solution was removed in vacuo. The residue was purified by preparative HPLC to give the title compound (44.1 mg, 39.1% yield, 100% ee). LCMS (ESI) m/z: 463 (M+1). $^1$H NMR (METHANOL-d4) δ ppm 8.52 (s, 1H), 8.13 (s, 1H), 7.54 (s, 1H), 6.99-7.19 (m, 2H), 4.51-4.81 (m, 1H), 4.23-4.39 (m, 2H), 3.12-3.32 (m, 3H), 2.92-3.04 (m, 1H), 2.31-2.43 (m, 2H).

Embodiment 16

Intermediate 16A: (S)-1-bromo-N-(1-(2,3-difluorophenyl)-3-(1,3-dioxoisoindolin-2-yl)propan-2-yl)-6,7-dihydro-5H-pyrazolo[1,5-a]thieno[3,2-c]azepine-9-carboxamide Prepare according to the method as described in the preparation of intermediate 11. LCMS (ESI) m/z: 611 (M+1).

Preparation of Embodiment 16

Prepare according to the method as described in embodiment 15. LCMS (ESI) m/z: 481 (M+1). $^1$H NMR (400 MHz, METHANOL-d4) δ ppm 2.31-2.45 (m, 2H), 2.97-3.31 (m, 6H), 4.23-4.36 (m, 2H), 4.52-4.73 (m, 1H), 7.02-7.25 (m, 3H), 7.54 (s, 1H), 8.06-8.19 (m, 1H), 8.41-8.61 (m, 1H).

Embodiment 17

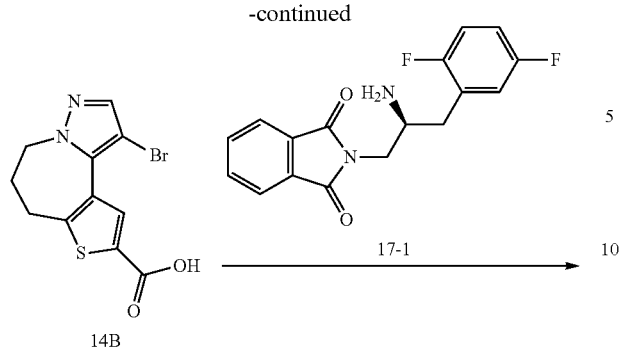
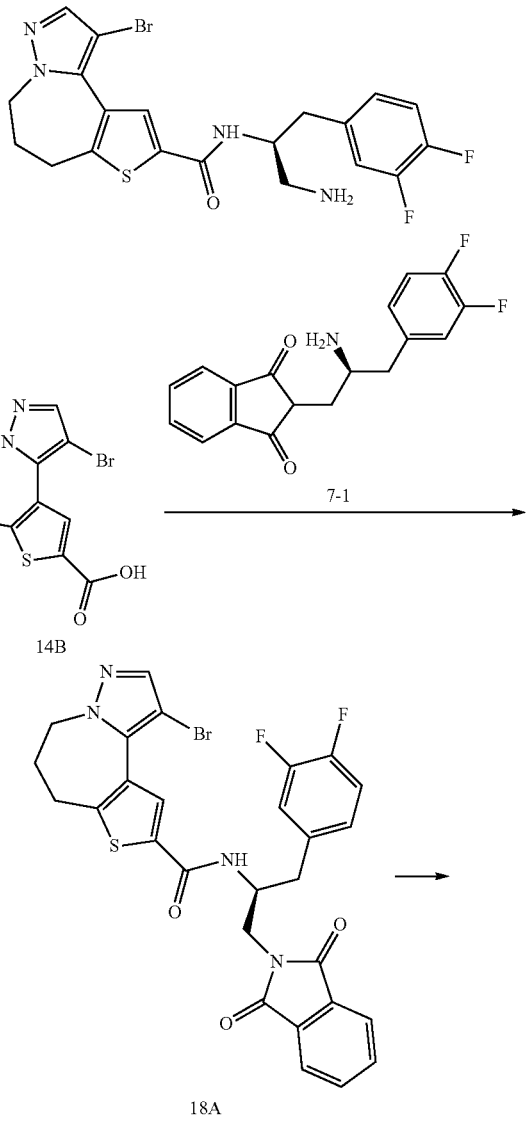

Intermediate 17A: (S)-1-bromo-N-(1-(2,5-difluorophenyl)-3-(1,3-dioxoisoindolin-2-yl)propan-2-yl)-6,7-dihydro-5H-pyrazolo[1,5-a]thieno[3,2-c]azepine-9-carboxamide Prepare according to the method as described in the preparation of intermediate 11. LCMS (ESI) m/z: 611 (M+1).

Preparation of Embodiment 17

Prepare according to the method as described in embodiment 15. LCMS (ESI) m/z: 481 (M+1). $^1$H NMR (400 MHz, METHANOL-d4) δ ppm 2.26-2.46 (m, 2H), 2.92-3.03 (m, 1H), 3.12 (s, 3H), 3.15-3.31 (m, 2H), 4.23-4.38 (m, 2H) 4.52-4.71 (m, 1H), 6.95-7.05 (m, 1H), 7.05-7.17 (m, 2H), 7.54 (s, 1H), 8.13 (s, 1H), 8.36-8.64 (m, 1H).

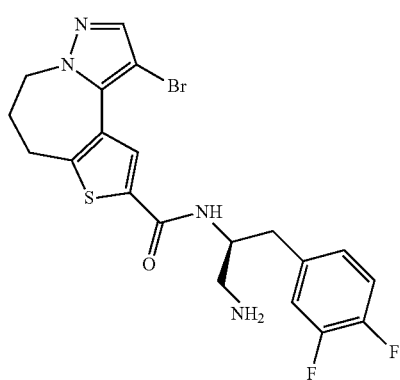

Intermediate 18A: (S)-1-bromo-N-(1-(3,4-difluorophenyl)-3-(1,3-dioxoisoindolin-2-yl)propan-2-yl)-6,7-dihydro-5H-pyrazolo[1,5-a]thieno[3,2-c]azepine-9-carboxamide Prepare according to the method as described in the preparation of intermediate 11. LCMS (ESI) m/z: 611 (M+1).

Preparation of Embodiment 18

Prepare according to the method as described in embodiment 15. LCMS (ESI) m/z: 481 (M+1). $^1$H NMR (400 MHz, METHANOL-d4) δ ppm 2.32-2.43 (m, 2H), 2.88-3.06 (m, 2H), 3.09-3.16 (m, 3H), 3.20-3.31 (m, 1H), 4.25-4.37 (m, 2H), 4.46-4.56 (m, 1H), 7.07-7.28 (m, 3H), 7.54 (s, 1H), 8.12 (s, 1H), 8.51 (s, 1H).

Embodiment 19

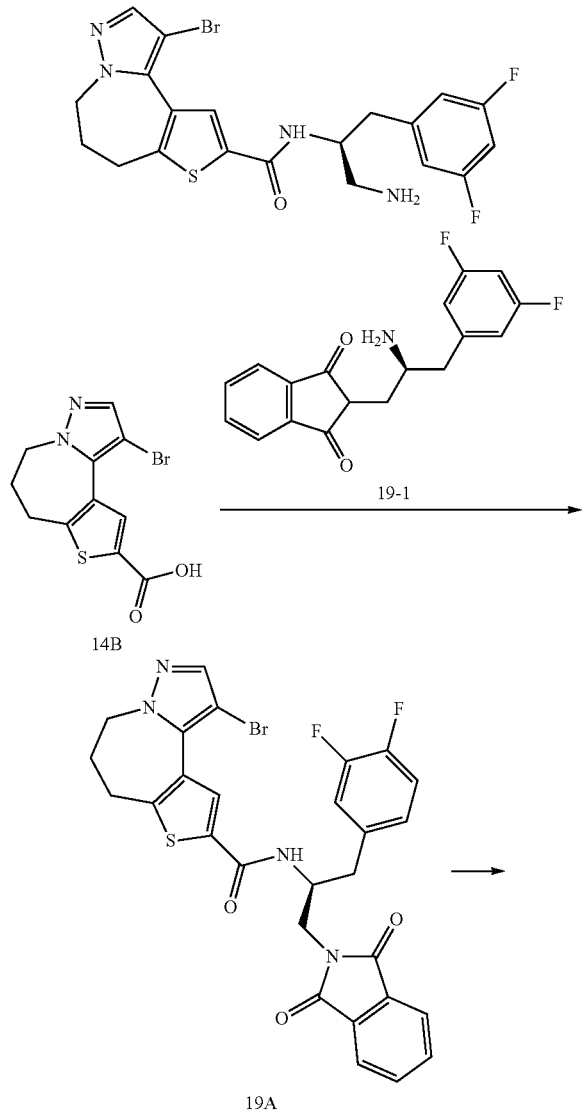

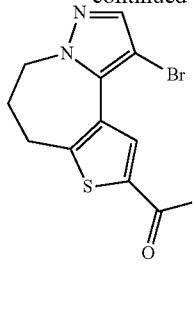

Embodiment 19

Intermediate 19A: (S)-1-bromo-N-(1-(3,5-difluorophenyl)-3-(1,3-dioxoisoindolin-2-yl)propan-2-yl)-6,7-dihydro-5H-pyrazolo[1,5-a]thieno[3,2-c]azepine-9-carboxamide Prepare according to the method as described in the preparation of intermediate 14C. LCMS (ESI) m/z: 611 (M+1).

Preparation of Embodiment 19

Prepare according to the method as described in embodiment 14. LCMS (ESI) m/z: 481 (M+1). $^1$H NMR (400 MHz, METHANOL-d4) δ ppm 2.23-2.25 (m, 7.07 Hz, 2H), 2.88-2.96 (m, 4H), 3.04-3.07 (t, J=7.09 Hz, 2H), 4.23-4.29 (m, 3H), 7.70-7.07 (m, 3H), 7.63 (s, 1H), 8.13 (s, 1H), 8.36 (s, 1H), 8.84-8.36 (br d, J=8.19 Hz, 1H).

Embodiment 20

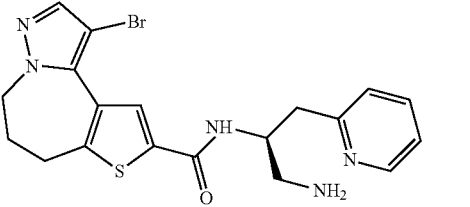

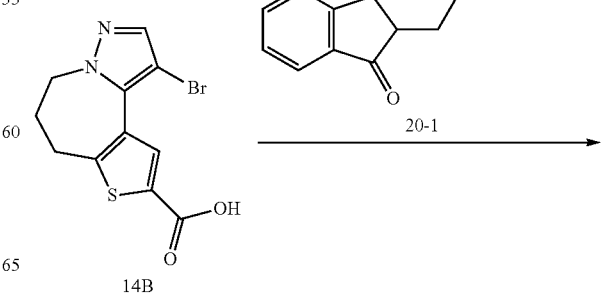

61
-continued

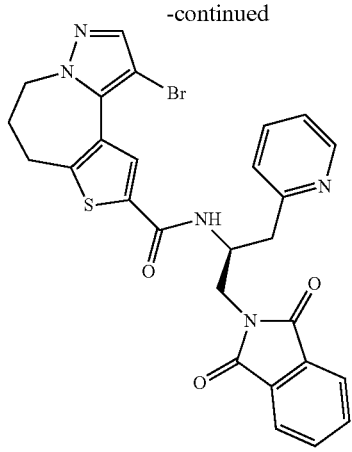

20A

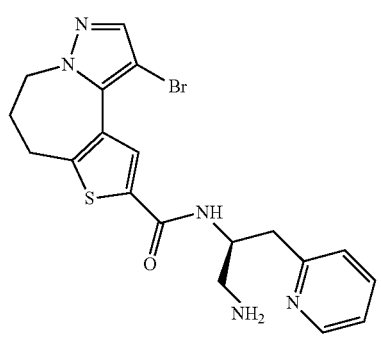

Embodiment 20

Intermediate 20A: (S)-1-bromo-N-(1-(1,3-dioxoisoindolin-2-yl)-3-(pyridin-2-yl)propan-2-yl)-6,7-dihydro-5H-pyrazolo[1,5-a]thieno[3,2-c]azepine-9-carboxamide Prepare according to the method as described in the preparation of intermediate 14C. LCMS (ESI) m/z: 576 (M+1).

Preparation of Embodiment 20

Prepare according to the method as described in embodiment 14. LCMS (ESI) m/z: 446 (M+1). $^1$H NMR (400 MHz, DMSO-d6) δ ppm 2.25 (q, J=6.79 Hz, 2H), 2.88 (br d, J=5.99 Hz, 2H), 3.02-3.07 (m, 4H), 4.23-4.32 (m, 2H), 4.36-4.50 (m, 1H), 7.22 (dd, J=6.85, 5.14 Hz, 1H), 7.30 (d, J=7.70 Hz, 1H), 7.62 (s, 1H), 7.70 (td, J=7.58, 1.59 Hz, 1H), 8.09 (s, 1H), 8.36 (s, 1H), 8.49 (d, J=4.03 Hz, 1H), 8.79 (br d, J=7.82 Hz, 1H).

62

Embodiment 21

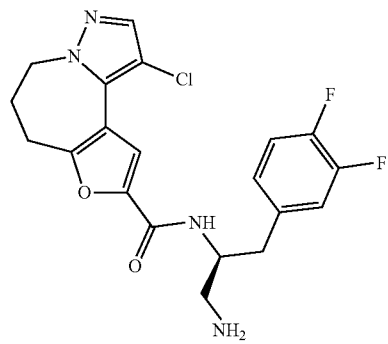

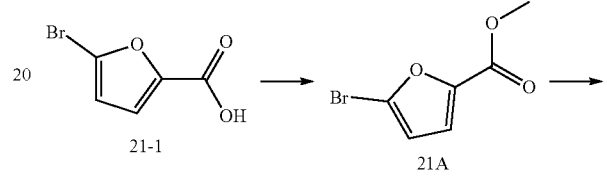

21-1    21A

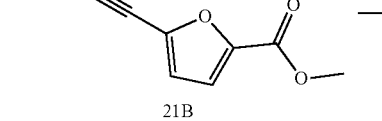

21B

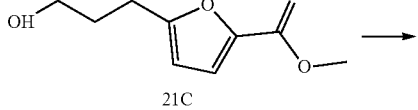

21C

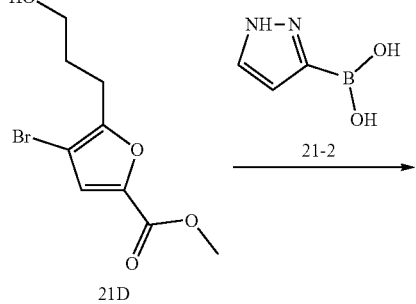

21D

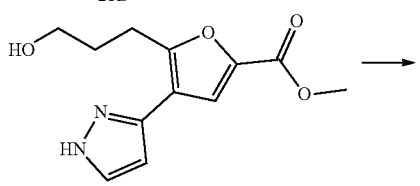

21E

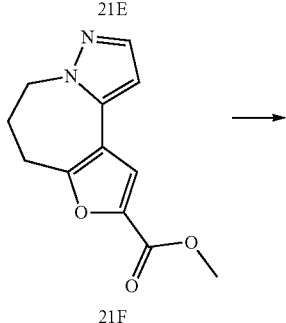

21F

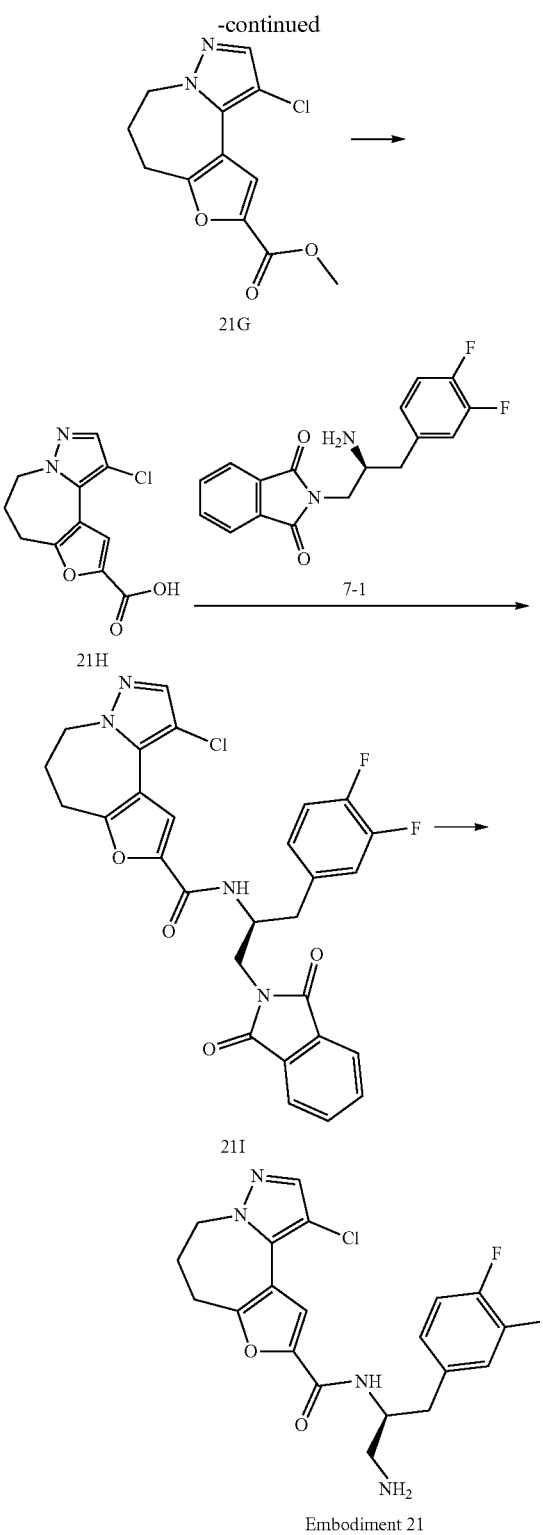

Embodiment 21

Intermediate 21A: methyl 5-bromofuran-2-carboxylate

Concentrated sulfuric acid (14.72 g, 150.08 mmol, 8 mL) was added to a solution of 5-bromofuran-2-carboxylic acid (8.00 g, 41.89 mmol) in methanol. The mixture was refluxed at 90° C. for 24 h, and then cooled to room temperature, the methanol was evaporated under reduced pressure. The residue was diluted with ethyl acetate (150 mL), washed with saturated sodium hydrogen carbonate solution (50 mL*3) and saturated brine (20 mL*2). The organic phase was dried over anhydrous sodium sulfate, filtered and concentrated by rotary evaporator to give the title compound (white solid, 8.12 g, 94.55% yield) which was used for the next step without further purification. $^1$H NMR (400 MHz, CHLOROFORM-d) 6 ppm 3.90 (s, 3H), 6.43-6.49 (m, 1H), 7.10-7.16 (m, 1H).

Intermediate 21B: methyl 5-(3-hydroxyprop-1-yn-1-yl)furan-2-carboxylate

Intermediate 21A (3.8 g, 18.54 mmol), Pd(PPh$_3$)$_2$Cl$_2$ (650.51 mg, 926.78 µmol) and cuprous iodide (176.51 mg, 926.78 µmol) were suspended in a mixed solvent of triethylamine (18.83 g, 186.10 mmol, 25.80 mL) and acetonitrile (12.50 mL) at 20° C. under nitrogen, and propargyl alcohol (2.08 g, 37.07 mmol, 2.19 mL) was added dropwise to the resultant mixture. The mixture was reacted at 100° C. for 3 h, and monitored by thin layer chromatography to detect the completion of the reaction. The reaction solution was cooled to room temperature, diluted with methylene chloride (150 mL), filtered, and the filtrate was washed with 2 N hydrochloric acid (100 mL*2), dried over anhydrous magnesium sulfate, filtered and concentrated with rotary evaporator. The residue was purified by HPLC to give the title compound (yellow oil, 2.2 g, 63.18% yield). LCMS (ESI) m/z: 181 (M+1). $^1$H NMR (400 MHz, CHLOROFORM-d) δ ppm 1.69-1.79 (m, 1H), 3.93 (s, 3H), 4.53 (d, J=6.27 Hz, 2H), 6.62-6.72 (m, 1H), 7.13-7.21 (m, 1H).

Intermediate 21C: methyl 5-(3-hydroxypropyl)furan-2-carboxylate

Dry palladium carbon (0.3 g, 10%) was added to a solution of the intermediate 21B (2.2 g, 10.94 mmol) in methanol (100 mL) under nitrogen. The suspension was charged three times with hydrogen and then hydrogenated at 25° C., 50 psi for 4 h. The palladium on carbon was filtered, and the organic phase was concentrated to give the title compound (yellow oil, 2.0 g, 84.30% yield), which was used directly in the next step without further purification. LCMS (ESI) m/z: 185 (M+1). $^1$H NMR (400 MHz, CHLOROFORM-d) δ ppm 1.91-2.04 (m, 2H), 2.78-2.88 (m, 2H), 3.67-3.77 (m, 2H), 3.89 (s, 3H), 6.15-6.21 (m, 1H), 7.08-7.16 (m, 1H).

Intermediate 21D: methyl 4-bromo-5-(3-hydroxypropyl)furan-2-carboxylate

Liquid bromine (2.21 g, 13.83 mmol) was added dropwise to a solution of intermediate 21C (2.0 g, 9.22 mmol) and aluminum trichloride (3.69 g, 27.67 mmol) in dichloromethane (50 mL) at 0° C. under nitrogen. After the addition, the mixture was stirred at 25° C. for 2 h, then quenched with water (30 mL), extracted with ethyl acetate (80 mL). The organic phase was washed with saturated sodium thiosulfate (30 mL*2), dried over anhydrous sodium sulfate, filtered and evaporated. The residue was purified by column chromatography to give the title compound (yellow oil, 2.10 g, 85.22% yield). LCMS (ESI) m/z: 263 (M+1). $^1$H NMR 1H NMR (400 MHz, CHLOROFORM-d) δ ppm 1.95 (t, J=7.15 Hz, 2H), 2.85 (s, 2H), 3.68 (s, 2H), 3.88 (s, 3H), 7.08-7.17 (s, 1H).

Intermediate 21E: methyl 5-(3-hydroxypropyl)-4-(1H-pyrazol-3-yl) furan-2-carboxylate A mixture of intermediate 21D (700 mg, 2.62 mmol), 1H-pyrazol-3-yl boronic acid (586.19 mg, 5.24 mmol, hydrochloride), Pd(dppf)Cl$_2$ (191.67 mg, 261.95 μmol) and sodium bicarbonate (1.32 g, 15.72 mmol) in a mixed solvent of DMF (5 mL) and water (1 mL) was stirred at 105° C. for 4 h under nitrogen. The mixture was cooled to room temperature, adjusted to pH=5 with 2 N hydrochloric acid. The aqueous phase was extracted with ethyl acetate (50 mL*2), and the organic phase was combined, washed with saturated brine (10 mL*2), dried over anhydrous sodium sulfate, filtered and concentrated. The residue was purified by column chromatography to give the title compound (yellow solid, 142 mg, 19.46% yield). LCMS (ESI) m/z: 251 (M+1). $^1$H NMR (400 MHz, CHLOROFORM-d) δ ppm 1.92-2.12 (m, 2H), 2.78-3.24 (m, 2H), 3.58-3.77 (m, 2H), 3.85-4.00 (m, 3H), 6.16-6.51 (m, 1H), 7.10-7.16 (m, 1H), 7.29-7.45 (m, 1H), 7.12-7.66 (m, 1H).

Intermediate 21F: methyl 6,7-dihydro-5H-furo[3,2-c]pyrazolo[1,5-a]azepine-9-carboxylate Triphenylphosphine (125.77 mg, 479.52 μmol) was added to a solution of intermediate 19E (133.55 mg, 479.52 μmol) and carbon tetrabromide (17.63 g, 44.31 mmol) in tetrahydrofuran (3 mL) at 0° C. under nitrogen. The reaction was stirred at 60° C. for 2 h and then concentrated to dryness. Cesium carbonate (156.24 mg, 479.52 μmol), potassium iodide (79.60 mg, 479.52 μmol) and DMF (3 mL) were added to the above mixture. The mixture was further stirred at 20° C. for 2 h, then concentrated to dryness. The residue is purified by preparative thin layer chromatography to give the title compound (yellow solid, 101 mg, 85.79% yield). LCMS (ESI) m/z: 233 (M+1). $^1$H NMR (400 MHz, METHANOL-d4) δ ppm 2.22-2.31 (m, 2H), 3.15-3.22 (m, 2H), 3.90 (s, 3H), 4.43-4.51 (m, 2H), 6.56-6.61 (m, 1H), 7.43 (d, J=1.76 Hz, 1H), 7.51 (s, 1H).

Intermediate 21G: methyl 1-chloro-6,7-dihydro-5H-furo[3,2-c]pyrazolo[1,5-a]azepine-9-carboxylate NCS (63.96 mg, 478.99 μmol) was added to a solution of intermediate 21F (98 mg, 399.16 μmol) in tetrahydrofuran (8 mL) at 20° C. The reaction mixture was stirred at 20° C. for 4 h, then quenched with water (10 mL), and extracted with ethyl acetate (80 mL*2). The organic phase was washed with saturated brine (10 mL*2), dried over anhydrous sodium sulfate, filtered and evaporated. The residue was purified by preparative thin layer chromatography to give the title compound (yellow solid, 72 mg, 51.71% yield). LCMS (ESI) m/z: 267 (M+1). $^1$H NMR (400 MHz, CHLOROFORM-d) δ ppm 2.08-2.27 (m, 2H), 3.11 (s, 2H), 3.86 (s, 3H), 4.35 (d, J=9.66 Hz, 2H), 7.32 (s, 1H), 7.82 (s, 1H).

Intermediate 21I: 1-chloro-6,7-dihydro-5H-furo[3,2-c]pyrazolo[1,5-a]azepine-9-carboxylic acid Lithium hydroxide monohydrate (87 mg, 2.06 mmol) was added to a mixed solution of the intermediate 21G (72 mg, 206.27 μmol) in tetrahydrofuran (3 mL) and water (3 mL), then the mixture was reacted at 10-20° C. for 12 h. After completion of the reaction, the mixture was adjusted to pH=5 with 2 N hydrochloric acid, and then extracted with ethyl acetate (80 mL*2). The organic phase was washed with saturated brine (10 mL*2), dried over anhydrous sodium sulfate, filtered and concentrated to give the title compound (yellow solid, 78 mg, 89.21% yield), which was used for next step without further purification. LCMS (ESI) m/z: 253 (M+1).

Intermediate 21L: (S)-1-chloro-N-(1-(3,4-difluorophenyl)-3-(1,3-dioxoisoindolin-2-yl)-6,7-dihydro-5H-furo[3,2-c]pyrazolo[1,5-a]azepine-9-carboxamide Diisopropylethylamine (143 mg, 1.1 mmol) and T$_3$P (234 mg, 368.03 μmol, 218.88 μL, ethyl acetate solution with 50% purity) were added to a mixed solution of intermediate 21H (78 mg, 184.02 μmol) and (S)-2-(2-amino-3-(3,4-difluorophenyl)propyl)isoindoline-1,3-dione (116 mg, 368.03 μmol, hydrochloride) in DMF (2 mL) at 0° C. under nitrogen. The mixture was reacted at 25° C. for 2 h, and then 2N hydrochloric acid (10 mL) was added. Then the mixture was extracted with ethyl acetate (50 mL*2), and the organic phase was washed with saturated brine (10 mL*2), dried over anhydrous sodium sulfate, filtered and concentrated. The residue was purified by preparative thin layer chromatography to give the title compound (white solid, 98 mg, 73.57% yield). LCMS (ESI) m/z: 551 (M+1).

Preparation of Embodiment 21

Hydrazine hydrate (203 mg, 4.06 mmol) was added to a solution of the intermediate 21I (98 mg, 135.38 μmol) in methanol (5 mL) at 20° C. The mixture was stirred at 60° C. for 0.5 h, and the solvent was removed in vacuo. The residue was purified by preparative HPLC to give the title compound (19.38 mg, 33.93% yield, 100% ee). LCMS (ESI) m/z: 421 (M+1). $^1$H NMR (400 MHz, METHANOL-d4) δ ppm 2.16-2.32 (m, 2H), 2.86-3.06 (m, 2H), 3.07-3.29 (m, 4H), 4.37-4.48 (m, 2H), 4.49-4.62 (m, 1H), 7.04-7.13 (m, 1H), 7.13-7.29 (m, 2H), 7.44 (s, 1H), 7.82 (s, 1H), 8.51 (s, 1H).

Embodiment 22

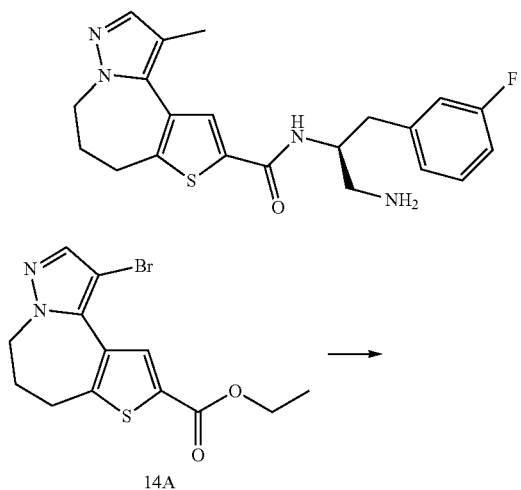

14A

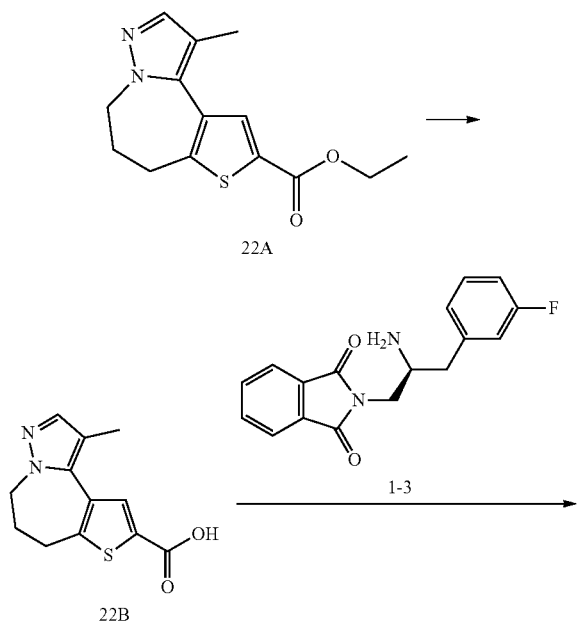

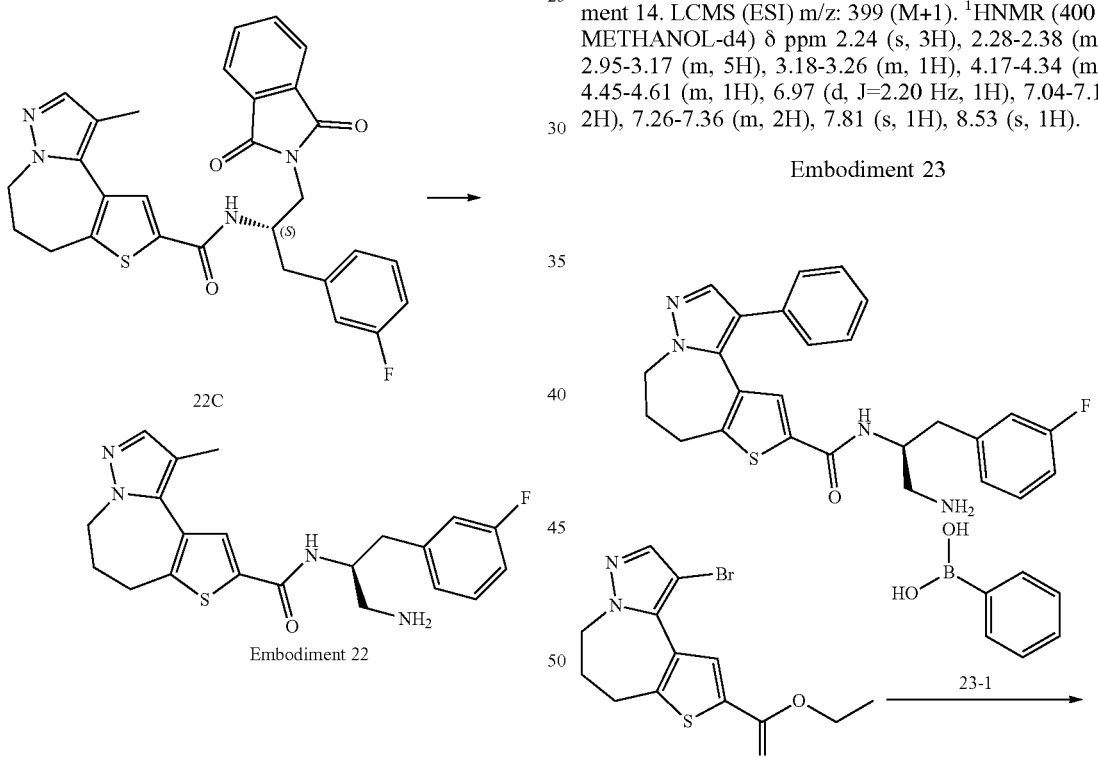

Intermediate 22A: ethyl 1-methyl-6,7-dihydro-5H-pyrazolo[1,5-a]thieno[3,2-c]azepine-9-carboxylate Pd(dppf)Cl$_2$·CH$_2$Cl$_2$ (47 mg, 57.87 µmol) and potassium carbonate (240 mg, 1.74 mmol) were added to a solution of intermediate 14A (100 mg, 289.35 µmol) and methyl boronic acid (139 mg, 2.31 mmol) in DMF (12 mL). The reaction solution was stirred at 110° C. for 7 h under nitrogen, then diluted with ethyl acetate (25 mL), washed with saturated brine (40 mL*3), dried over anhydrous sodium sulfate, filtered and concentrated to give the title compound (red solid, 100 mg, crude) which was used directly in the next step. LCMS (ESI) m/z: 277 (M+1).

Intermediate 22B: 1-methyl-6,7-dihydro-5H-pyrazolo[1,5-a]thieno[3,2-c]azepine-9-carboxylic acid Prepare according to the method as described in the preparation of intermediate 14B, the afforded intermediate 20B was used directly in the next step without further purification. LCMS (ESI) m/z: 249 (M+1).

Intermediate 22C: N—((S)-1-(1,3-dioxoisoindolin-2-yl)-3-(3-fluorophenyl) propan-2-yl)-1-methyl-6,7-dihydro-5H-pyrazolo[1,5-a]thieno[3,2-c]azepine-9-carboxamide Prepare according to the method as described in the preparation of intermediate 14C, which was purified by thin layer preparative chromatography to give the title compound. LCMS (ESI) m/z: 529 (M+1). $^1$HNMR (400 MHz, CHLOROFORM-d) δ ppm 2.31 (s, 5H), 2.92-3.23 (m, 4H), 3.77-4.00 (m, 2H), 4.22-4.42 (m, 2H), 4.55-4.63 (m, 1H), 6.87-6.92 (m, 1H), 6.95-7.06 (m, 2H), 7.09-7.14 (m, 1H), 7.29-7.38 (m, 2H), 7.59 (s, 1H), 7.70-7.79 (m, 2H), 7.81-7.90 (m, 2H).

Preparation of Embodiment 22

Prepare according to the method as described in embodiment 14. LCMS (ESI) m/z: 399 (M+1). $^1$HNMR (400 MHz, METHANOL-d4) δ ppm 2.24 (s, 3H), 2.28-2.38 (m, 2H), 2.95-3.17 (m, 5H), 3.18-3.26 (m, 1H), 4.17-4.34 (m, 2H), 4.45-4.61 (m, 1H), 6.97 (d, J=2.20 Hz, 1H), 7.04-7.17 (m, 2H), 7.26-7.36 (m, 2H), 7.81 (s, 1H), 8.53 (s, 1H).

Embodiment 23

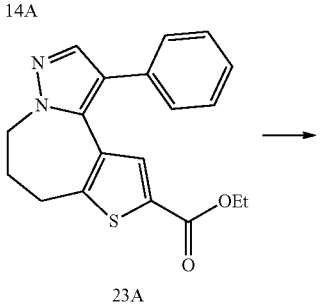

-continued

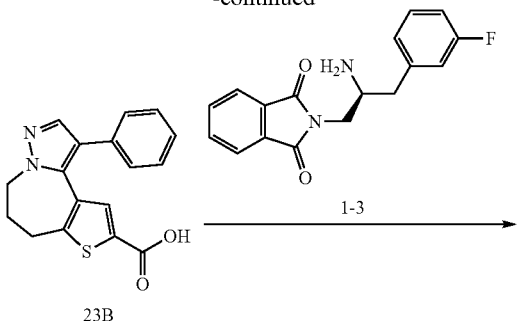

23B

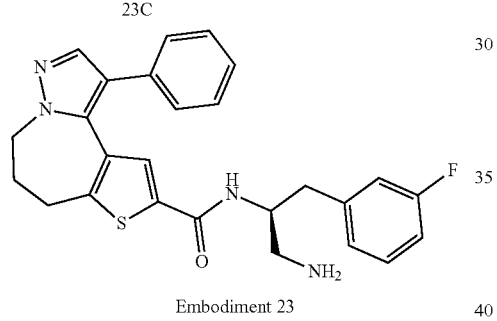

23C

Embodiment 23

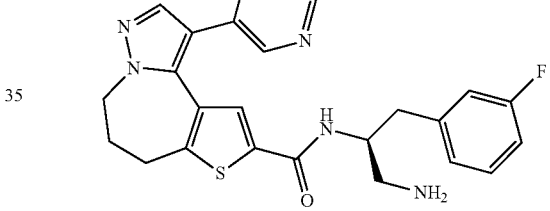

Embodiment 23

Intermediate 23A: ethyl 1-phenyl-6,7-dihydro-5H-pyrazolo[1,5-a]thieno [3,2-c]azepine-9-carboxylate Pd(dppf)Cl$_2$·CH$_2$Cl$_2$ (28.72 mg, 35.17 μmol) and sodium bicarbonate (30 mg, 351.67 μmol) were added to a solution of intermediate 14A (80 mg, 234.45 μmol) and phenyl boronic acid (34 mg, 281.34 μmol) in 1,4-dioxane (4 mL) and water (0.8 mL). The reaction solution was stirred at 110° C. for 16 h under nitrogen. After the completion of the reaction, the reaction mixture was filtered. The filtrate was then diluted with ethyl acetate (10 mL), washed with saturated brine (10 mL), dried over anhydrous sodium sulfate, filtered and concentrated. The residue was purified by thin layer preparative chromatography to give the title compound (transparent oil, 61 mg, 73.96% yield). LCMS (ESI) m/z: 339 (M+1).

Intermediate 23B: 1-phenyl-6,7-dihydro-5H-pyrazolo[1,5-a]thieno[3,2-c]azepine-9-carboxylic acid Prepare according to the method as described in the preparation of intermediate 14B, the afforded title compound was used directly in the next step without further purification.

Intermediate 23C: N—((S)-1-(1,3-dioxoisoindolin-2-yl)-3-(3-fluorophenyl) propan-2-yl)-1-phenyl-6,7-dihydro-5H-pyrazolo[1,5-a]thieno [3,2-c]azepine-9-carboxamide Prepare according to the method as described in the preparation of intermediate 14C, which was purified by thin layer preparative chromatography to give the title compound. LCMS (ESI) m/z: 591 (M+1). $^1$HNMR (400 MHz, METHANOL-d4) δ ppm 2.35-2.49 (m, 2H), 2.79-2.90 (m, 1H), 2.95-3.09 (m, 3H), 3.77-3.89 (m, 2H), 4.16-4.30 (m, 2H), 4.59-4.70 (m, 1H), 6.86-7.07 (m, 3H), 7.20-7.40 (m, 7H), 7.64-7.70 (m, 1H), 7.74-7.85 (m, 1H).

Preparation of Embodiment 23

Prepare according to the method as described in embodiment 14. LCMS (ESI) m/z: 461 (M+1). $^1$HNMR (400 MHz, METHANOL-d4) δ ppm 2.39-2.54 (m, 2H), 2.78-3.03 (m, 3H), 3.06-3.17 (m, 3H), 4.13-4.35 (m, 2H), 4.38-4.50 (m, 1H), 6.91-7.09 (m, 3H), 7.37 (d, J=4.14 Hz, 7H), 7.68 (s, 1H), 8.52 (s, 1H).

Embodiment 24

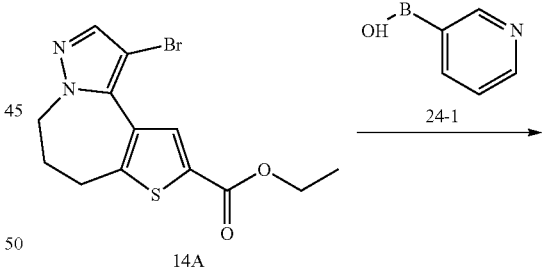

14A 24-1

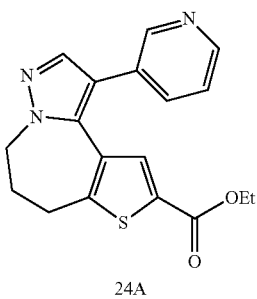

24A

-continued

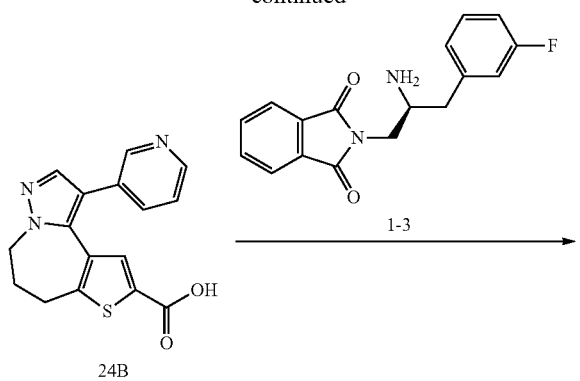

24B

24C

Embodiment 24

Intermediate 24A: ethyl 1-(pyridin-3-yl)-6,7-di-hydro-5H-pyrazolo[1,5-a]thieno[3,2-c]azepine-9-carboxylate Pd(dppf)Cl$_2$·CH$_2$Cl$_2$ (29 mg, 35.17 μmol) and sodium bicarbonate (30 mg, 351.67 μmol) were added to a solution of intermediate 14A (80 mg, 234.45 μmol) and 3-pyridine boronic acid (35 mg, 281.34 μmol) in 1,4-dioxane (4 mL) and water (0.8 mL). The reaction solution was stirred at 100° C. for 16 h under nitrogen, and then filtered. The filtrate was then diluted with ethyl acetate (10 mL), washed with saturated brine (10 mL), dried over anhydrous sodium sulfate, filtered and concentrated. The residue was purified by thin layer preparative chromatography to give the title compound (transparent oil, 56 mg, 69.46% yield). LCMS (ESI) m/z: 340 (M+1).

Intermediate 24B: 1-(pyridin-3-yl)-6,7-dihydro-5H-pyrazolo[1,5-a]thieno[3,2-c]azepine-9-carboxylic acid Prepare according to the method as described in the preparation of intermediate 14B, the afforded title compound was used directly in the next step without further purification.

Intermediate 224: N—((S)-1-(1,3-dioxoisoindolin-2-yl)-3-(3-fluorophenyl) propan-2-yl)-1-(pyridin-3-yl)-6,7-dihydro-5H-pyrazolo[1,5-a]thieno[3,2-c] azepine-9-carboxamide Prepare according to the method as described in the preparation of intermediate 14C, which was purified by thin layer preparative chromatography to give the title compound. LCMS (ESI) m/z: 592 (M+1). $^1$HNMR (400 MHz, METHANOL-d4) δ ppm 2.38-2.52 (m, 2H), 2.84-2.89 (m, 1H), 2.97-3.11 (m, 3H), 3.79-3.89 (m, 2H), 4.19-4.35 (m, 2H), 4.56-4.69 (m, 1H), 6.86-7.08 (m, 3H), 7.30 (s, 2H), 7.44-7.52 (m, 1H), 7.72-7.89 (m, 6H), 8.46-8.51 (m, 1H), 8.58-8.63 (m, 1H).

Preparation of Embodiment 24

Prepare according to the method as described in embodiment 14. LCMS (ESI) m/z: 462 (M+1). $^1$HNMR (400 MHz, METHANOL-d4) δ ppm 2.42-2.55 (m, 2H), 2.82-3.08 (m, 3H), 3.14 (s, 3H), 4.19-4.36 (m, 2H), 4.42-4.55 (m, 1H), 6.93-7.07 (m, 3H), 7.25-7.35 (m, 1H), 7.41 (s, 2H), 7.80 (s, 2H), 8.41-8.59 (m, 3H).

Embodiment 25

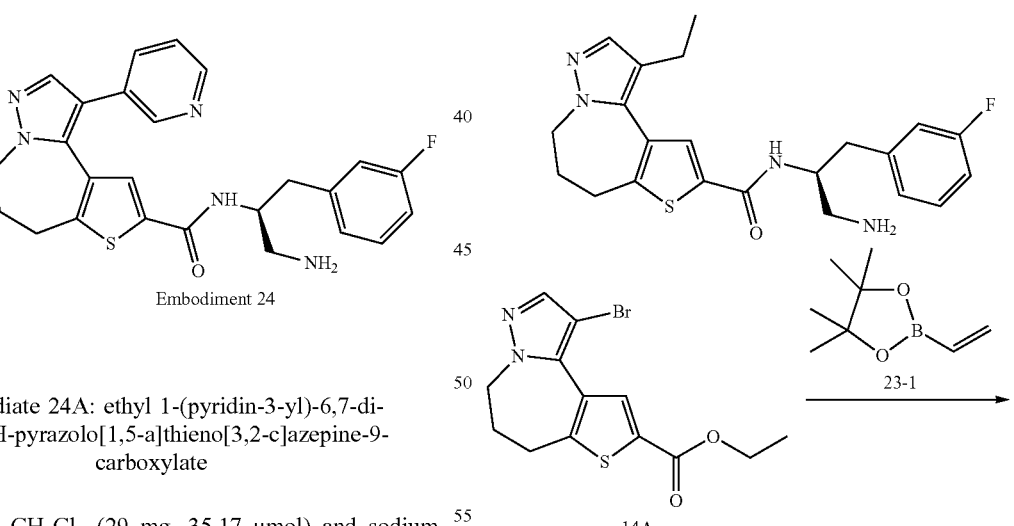

14A

25A

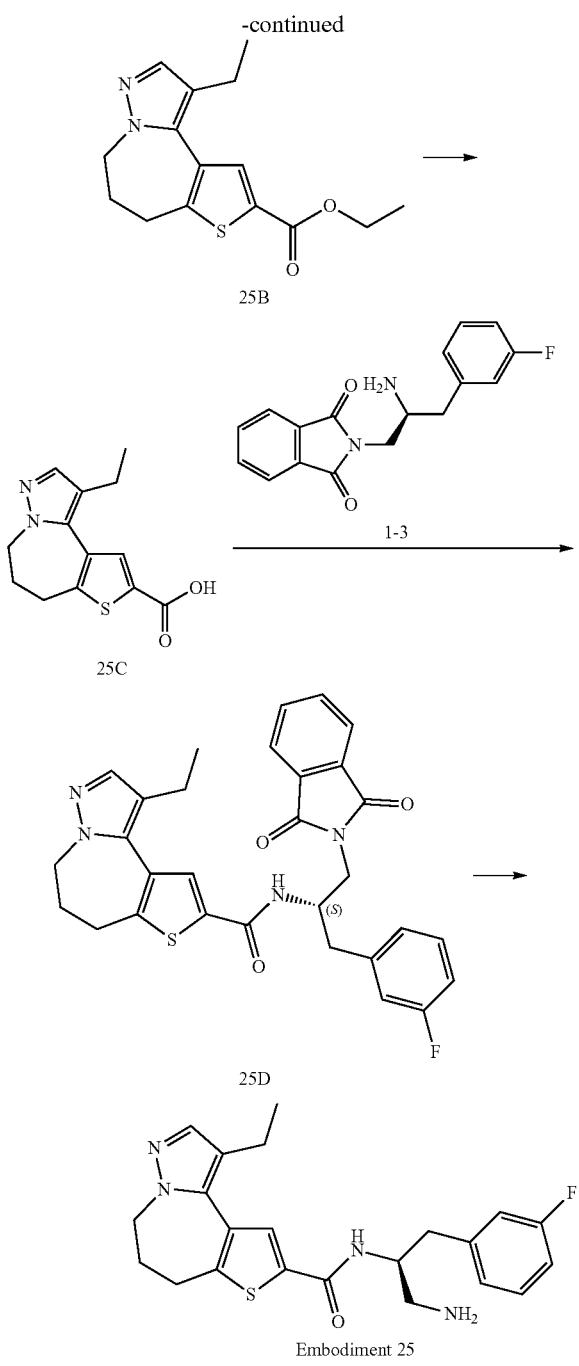

by thin layer preparative chromatography to give the title compound (transparent oil, 50 mg, 69.06% yield). LCMS (ESI) m/z: 289 (M+1).

Intermediate 25B: ethyl 1-ethyl-6,7-dihydro-5H-pyrazolo[1,5-a]thieno[3,2-c]azepine-9-carboxylate Dry palladium on carbon (50 mg, 10%) was added to a solution of intermediate 25A (50 mg, 161.91 μmol) in ethanol (10 mL) under nitrogen. The suspension was charged three times with hydrogen and then hydrogenated at 15° C., 1 atm for 1 h. The palladium on carbon was filtered off, and the organic solution was concentrated to give the title compound (yellow oil, 50 mg, 97.41% yield), which was used directly in the next step without further purification. LCMS (ESI) m/z: 291 (M+1). $^1$HNMR (400 MHz, CHLOROFORM-d) δ ppm 1.18-1.21 (m, 3H), 1.28-1.36 (m, 4H), 2.26-2.36 (m, 2H), 2.49-2.59 (m, 2H), 2.90-3.00 (m, 2H), 4.15-4.22 (m, 2H), 4.30 (d, J=7.21 Hz, 2H), 7.30 (s, 1H), 7.71-7.77 (m, 1H)

Intermediate 25C: 1-ethyl-6,7-dihydro-5H-pyrazolo[1,5-a]thieno[3,2-c]azepine-9-carboxylic acid Prepare according to the method as described in the preparation of intermediate 14B, the afforded title compound was used directly in the next step without further purification.

Intermediate 25D: N—((S)-1-(1,3-dioxoisoindolin-2-yl)-3-(3-fluorophenyl) propan-2-yl)-1-ethyl-6,7-dihydro-5H-pyrazolo[1,5-a]thieno[3,2-c]azepine-9-carboxamide Prepare according to the method as described in the preparation of intermediate 14C, the title compound was purified by thin layer preparative chromatography. LCMS (ESI) m/z: 543 (M+1). $^1$HNMR (400 MHz, CHLOROFORM-d) δ ppm 1.23 (s, 3H), 2.23-2.33 (m, 2H), 2.55-2.66 (m, 2H), 2.82-2.99 (m, 3H), 3.02-3.12 (m, 1H), 3.66-3.89 (m, 2H), 4.13-4.27 (m, 2H), 4.41-4.58 (m, 1H), 6.75-6.83 (m, 1H), 6.84-6.91 (m, 1H), 6.92-6.98 (m, 1H), 7.00-7.06 (m, 1H), 7.20-7.26 (m, 1H), 7.32 (s, 1H), 7.45 (s, 1H), 7.67 (s, 2H), 7.72-7.80 (m, 2H).

Preparation of Embodiment 25

Prepare according to the method as described in embodiment 14. LCMS (ESI) m/z: 413 (M+1). $^1$HNMR (400 MHz, METHANOL-d4) δ ppm 1.140 (t, J=7.58 Hz, 3H), 2.186-2.303 (m, 2H), 2.460-2.590 (m, 2H), 2.918 (s, 6H), 4.010-4.186 (m, 2H), 4.315-4.478 (m, 1H), 6.813-6.891 (m, 1H), 6.916-7.032 (m, 2H), 7.152-7.239 (m, 1H), 7.284 (s, 1H), 7.618-7.672 (m, 1H), 8.373-8.442 (m, 1H).

Embodiment 26

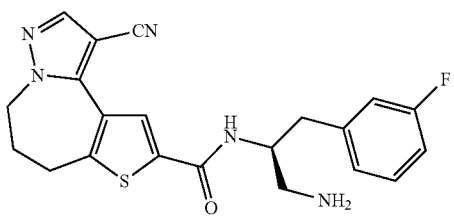

Intermediate 25A: ethyl 1-vinyl-6,7-dihydro-5H-pyrazolo[1,5-a]thieno[3,2-c]azepine-9-carboxylate Pd(dppf)Cl$_2$.CH$_2$Cl$_2$ (29 mg, 35.17 μmol) and sodium bicarbonate (30 mg, 351.67 μmol) were added to a solution of intermediate 14A (80 mg, 289.35 μmol) and intermediate 23-1 (72 mg, 468.9 μmol) in 1,4-dioxane (4 mL) and water (1 mL). The reaction solution was stirred at 100° C. for 16 h under nitrogen atmosphere, and then filtered. The filtrate was then diluted with ethyl acetate (10 mL), washed with saturated brine (10 mL), dried over anhydrous sodium sulfate, filtered and concentrated. The residue was purified

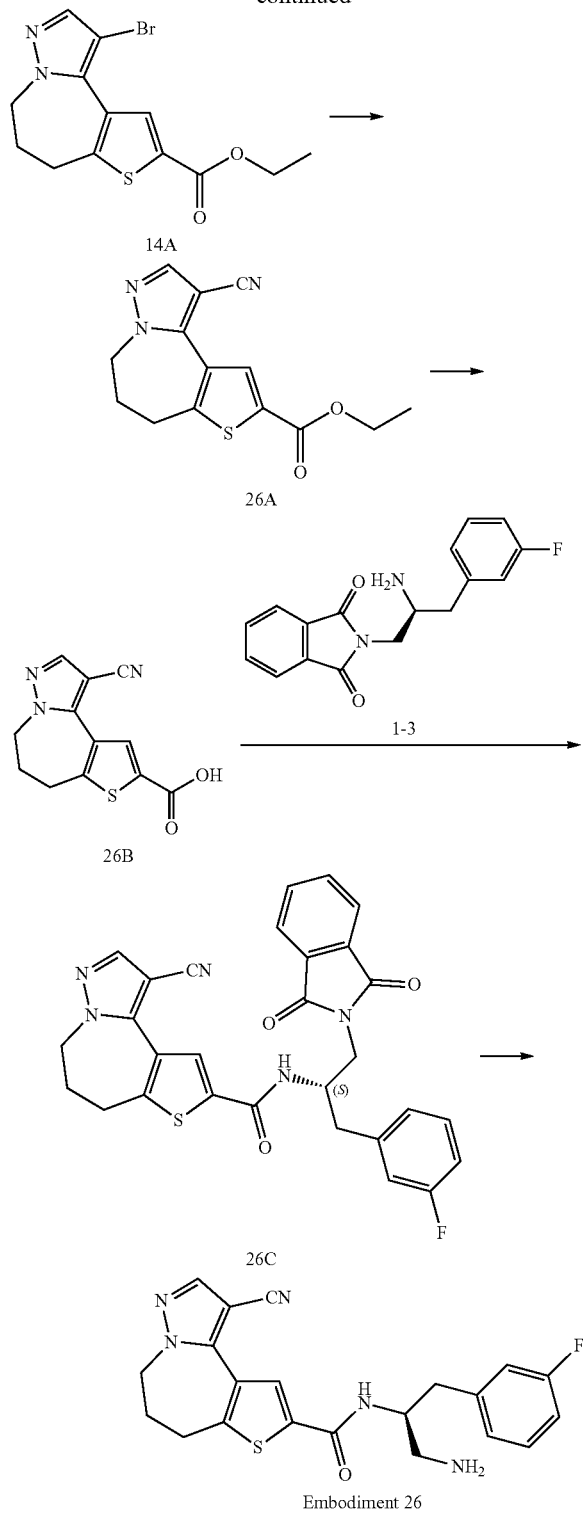

Intermediate 26A: ethyl 1-cyano-6,7-dihydro-5H-pyrazolo[1,5-a]thieno[3,2-c]azepine-9-carboxylate Pd$_2$(dba)$_3$ (32 mg, 35.17 μmol), DPPF (26 mg, 46.89 μmol), zinc cyanide (55 mg, 468.90 μmol), and Zn (31 mg, 468.90 μmol) were added to a solution of intermediate 14A (80 mg, 234.45 μmol) in DMF (5 mL). The reaction solution was stirred at 130° C. for 16 h under nitrogen, and then filtered. The filtrate was then diluted with ethyl acetate (10 mL), washed with saturated brine (10 mL), dried over anhydrous sodium sulfate, filtered and concentrated. The residue was purified by thin layer preparative chromatography to give the title compound (colorless transparent oil, 61 mg, 89.24% yield). LCMS (ESI) m/z: 288 (M+1). $^1$HNMR (400 MHz, METHANOL-d4) δ ppm 1.39 (t, J=7.15 Hz, 3H), 2.29-2.40 (m, 2H), 3.34-3.38 (m, 2H), 4.33-4.41 (m, 2H), 4.49-4.57 (m, 2H), 7.90 (s, 1H), 8.29-8.41 (m, 1H).

Intermediate 26B: 1-cyano-6,7-dihydro-5H-pyrazolo[1,5-a]thieno[3,2-c]azepine-9-carboxylic acid Prepare according to the method as described in the preparation of intermediate 14B, the afforded title compound was used directly in the next step without further purification.

Intermediate 26C: 1-cyano-N—((S)-1-(1,3-dioxoisoindolin-2-yl)-3-(3-fluorophenyl)propan-2-yl)-6,7-dihydro-5H-pyrazolo[1,5-a]thieno[3,2-c]azepine-9-carbox amide Prepare according to the method as described in the preparation of intermediate 14C, which was purified by thin layer preparative chromatography to give the title compound. LCMS (ESI) m/z: 540 (M+1). $^1$HNMR (400 MHz, CHLOROFORM-d) δ ppm 2.22-2.40 (m, 2H), 2.92-3.12 (m, 4H), 3.87-3.97 (m, 2H), 4.39-4.55 (m, 2H), 4.61-4.67 (m, 1H), 6.85-6.94 (m, 1H), 7.05-7.10 (m, 1H), 7.13-7.19 (m, 1H), 7.25-7.34 (m, 1H), 7.75-7.87 (m, 4H), 7.88-7.93 (m, 1H), 7.98-8.04 (m, 1H).

Preparation of Embodiment 26

Prepare according to the method as described in embodiment 14. LCMS (ESI) m/z: 399 (M+1). $^1$HNMR (400 MHz, METHANOL-d4) δ ppm 2.28-2.41 (m, 2H), 2.91-3.07 (m, 2H), 3.09-3.18 (m, 1H), 3.20-3.31 (m, 3H), 4.41-4.60 (m, 3H), 6.91-7.00 (m, 1H), 7.02-7.19 (m, 2H), 7.33 (d, J=6.27 Hz, 1H), 7.87-7.95 (m, 1H), 8.15 (s, 1H), 8.42-8.54 (m, 1H).

Embodiment 27

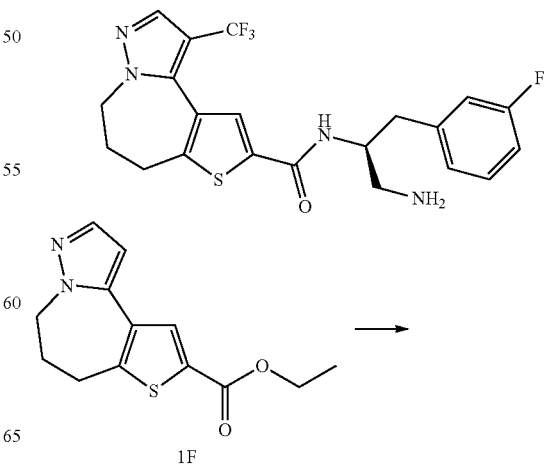

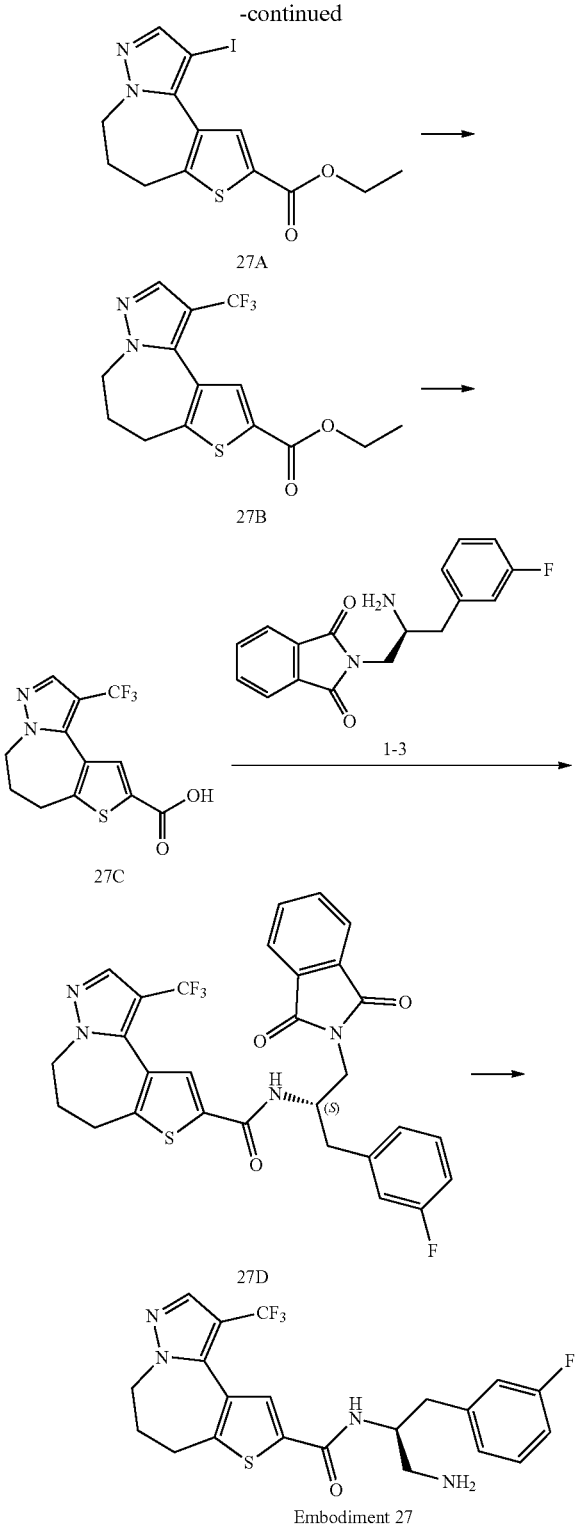

Intermediate 27A: ethyl 1-iodo-6,7-dihydro-5H-pyrazolo[1,5-a]thieno[3,2-c]azepine-9-carboxylate NIS (180 mg, 800 μmol) was added to a solution of intermediate 1F (200 mg, 762.40 μmol) in THF (5 mL). The reaction solution was stirred at 15-50° C. for 32 h. The reaction solution was directly concentrated to give the title compound (red solid, crude, 500 mg).

Intermediate 27B: ethyl 1-(trifluoromethyl)-6,7-dihydro-5H-pyrazolo[1,5-a]thieno[3,2-c]azepine-9-carboxylate Cuprous iodide (108 mg, 566.68 μmol) and methyl 2,2-difluoro-2-fluorosulfonyl-acetate (272.16 mg, 1.42 mmol) were added to a solution of intermediate 27A (110 mg, 283.34 μmol)) in DMF (5 mL). The reaction solution was stirred at 70° C. for 16 h, and then filtered. The filtrate was diluted with ethyl acetate (15 mL), washed with saturated brine solution (10 mL*2), dried over anhydrous sodium sulfate, filtered and concentrated. The residue was purified by thin layer preparative chromatography to give the title compound (white solid, 70 mg, 72.42% yield). LCMS (ESI) m/z: 331 (M+1).

Intermediate 27C: 1-(trifluoromethyl)-6,7-dihydro-5H-pyrazolo[1,5-a]thieno[3,2-c]azepine-9-carboxylic acid Prepare according to the method as described in the preparation of intermediate 14B, the afforded title compound was used directly in the next step without further purification.

Intermediate 27D: N—((S)-1-(1,3-dioxoisoindolin-2-yl)-3-(3-fluorophenyl) propan-2-yl)-1-(trifluoromethyl)-6,7-dihydro-5H-pyrazolo[1,5-a]thieno [3,2-c]azepine-9-carboxamide Prepare according to the method as described in the preparation of intermediate 14C, the title compound was purified by thin layer preparative chromatography. LCMS (ESI) m/z: 583 (M+1).

Preparation of Embodiment 27

Prepare according to the method as described in embodiment 14. LCMS (ESI) m/z: 453 (M+1). ¹HNMR (400 MHz, METHANOL-d4) δ ppm 2.43-2.53 (m, 2H), 2.94-3.07 (m, 4H), 3.10-3.25 (m, 2H), 4.19-4.34 (m, 2H), 4.48-4.59 (m, 1H), 6.92-7.01 (m, 1H), 7.03-7.17 (m, 2H), 7.25-7.38 (m, 1H), 7.77-7.81 (m, 1H), 7.81-7.86 (m, 1H), 8.41-8.56 (m, 1H).

Embodiment 28

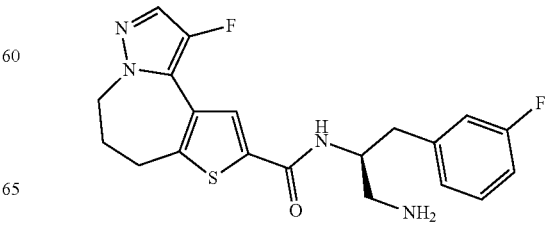

-continued

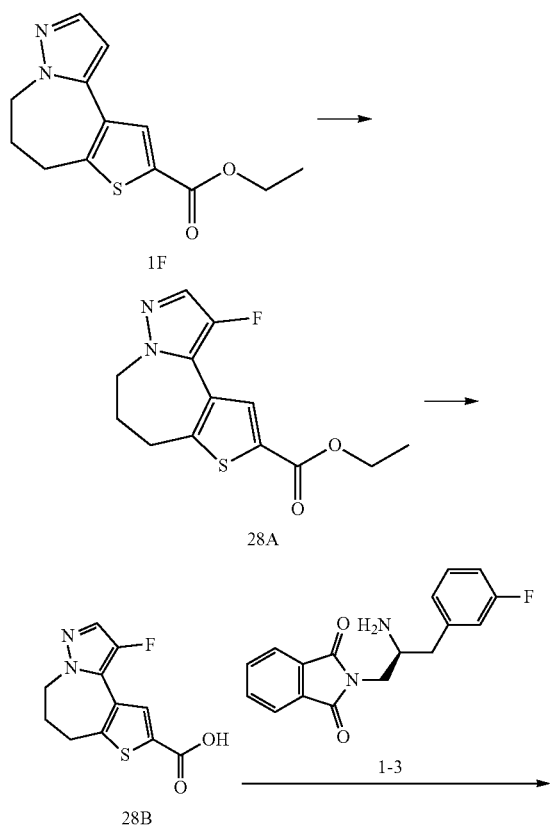

Intermediate 28A: ethyl 1-fluoro-6,7-dihydro-5H-pyrazolo[1,5-a]thieno[3,2-c]azepine-9-carboxylate Select F (243 mg, 686.16 μmol) was added to a solution of intermediate 1F (60 mg, 228.72 μmol) in THF (5 mL) and water (0.35 mL). The reaction solution was stirred at 70° C. for 40 h and concentrated directly. The residue was purified by thin layer preparative chromatography to give the title compound (white product, 45 mg, 68.07% yield). LCMS (ESI) m/z: 281 (M+1).

Intermediate 28B: 1-fluoro-6,7-dihydro-5H-pyrazolo[1,5-a]thieno[3,2-c]azepine-9-carboxylic acid Prepare according to the method as described in the preparation of intermediate 14B, the title compound was used directly in the next step without further purification.

Intermediate 28C: N—((S)-1-(1,3-dioxoisoindolin-2-yl)-3-(3-fluorophenyl) propan-2-yl)-1-fluoro-6,7-dihydro-5H-pyrazolo[1,5-a]thieno[3,2-c]azepine-9-carboxamide Prepare according to the method as described in the preparation of intermediate 14C, the title compound was purified by thin layer preparative chromatography. LCMS (ESI) m/z: 533 (M+1).

Preparation of Embodiment 28

Prepare according to the method as described in embodiment 14. LCMS (ESI) m/z: 403 (M+1). ¹HNMR (400 MHz, METHANOL-d4) δ ppm 2.22-2.34 (m, 2H), 2.93-3.05 (m, 2H), 3.08-3.29 (m, 4H), 4.40-4.57 (m, 3H), 6.93-7.01 (m, 1H), 7.03-7.15 (m, 2H), 7.28-7.36 (m, 1H), 7.43 (d, J=4.02 Hz, 1H), 8.00 (s, 1H), 8.41-8.58 (m, 1H).

Embodiment 29

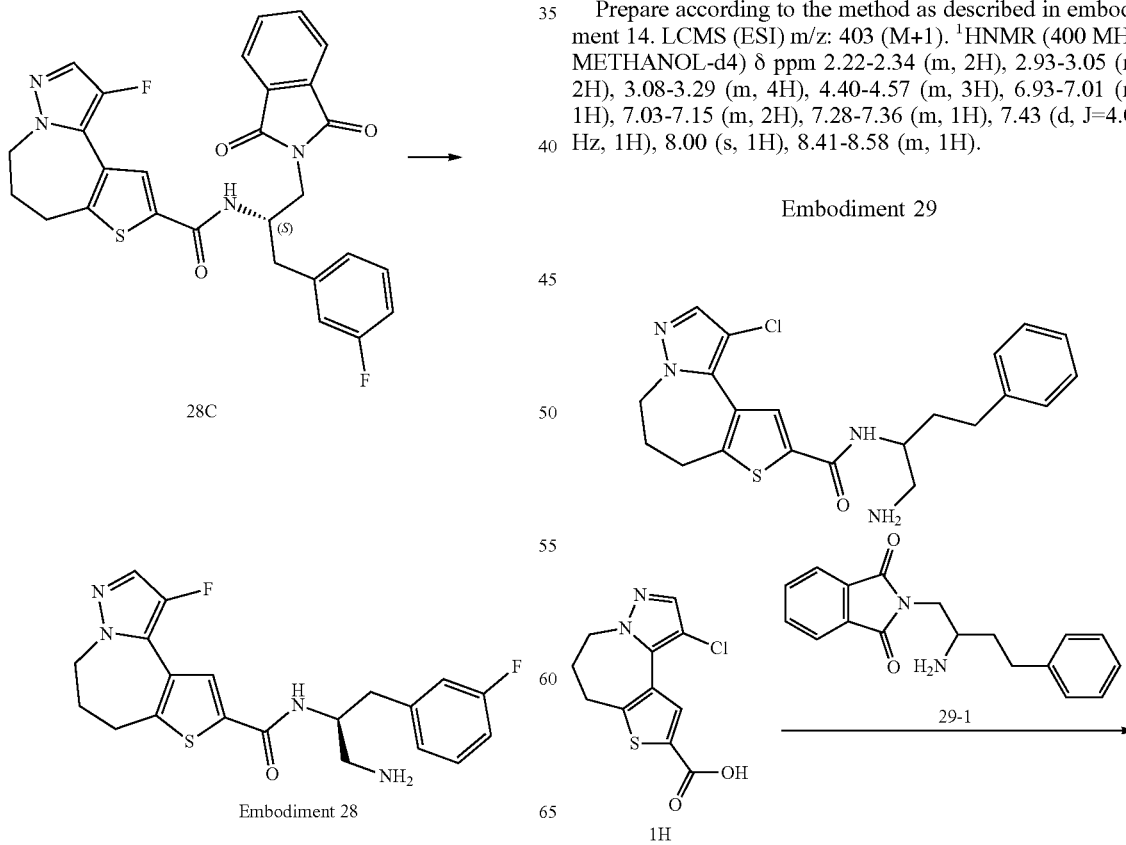

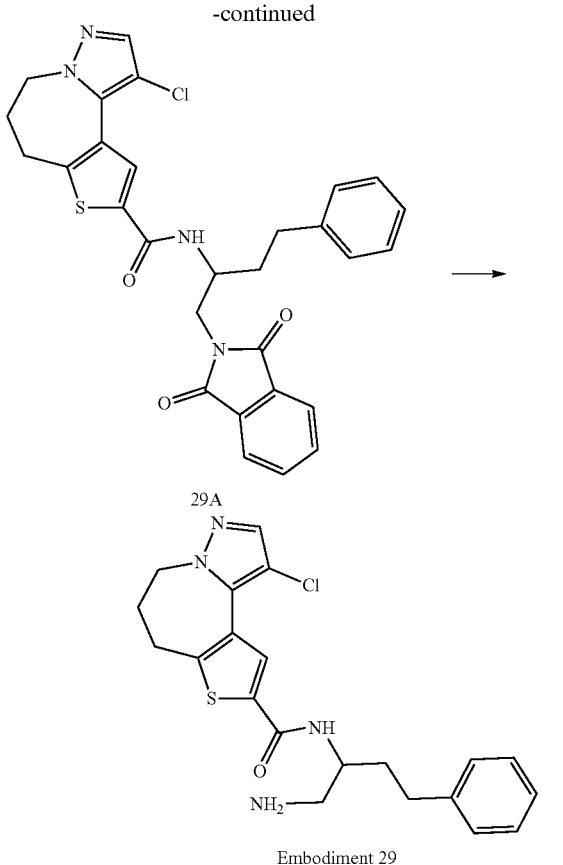

29A

Embodiment 29

Intermediate 29A: 1-chloro-N-(1-(1,3-dioxoisoindo-lin-2-yl)-4-phenyl butan-2-yl)-6,7-dihydro-5H-pyra-zolo[1,5-a]thieno[3,2-c]azepine-9-carboxamide Prepare according to the method as described in the preparation of intermediate 11, the title compound was purified by thin layer preparative chromatography. LCMS (ESI) m/z: 545 (M+1).

Preparation of Embodiment 29

Prepare according to the method as described in embodiment 14. LCMS (ESI) m/z: 415 (M+1). ¹HNMR (400 MHz, DMSO-d6) δ ppm 1.87 (d, J=6.90 Hz, 2H), 2.19-2.27 (m, 2H), 2.54-2.69 (m, 2H), 2.91 (br. s., 2H), 3.11-3.17 (m, 2H), 4.09 (d, J=5.27 Hz, 1H), 4.28-4.32 (m, 2H), 7.16-7.31 (m, 5H), 7.61 (s, 1H), 8.22 (s, 1H), 8.40 (s, 1H), 8.96 (d, J=7.91 Hz, 1H).

Embodiment 30

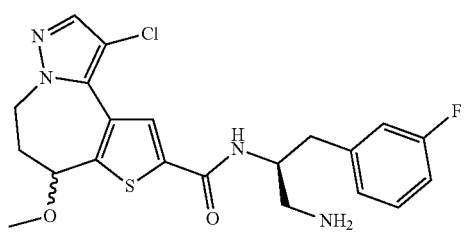

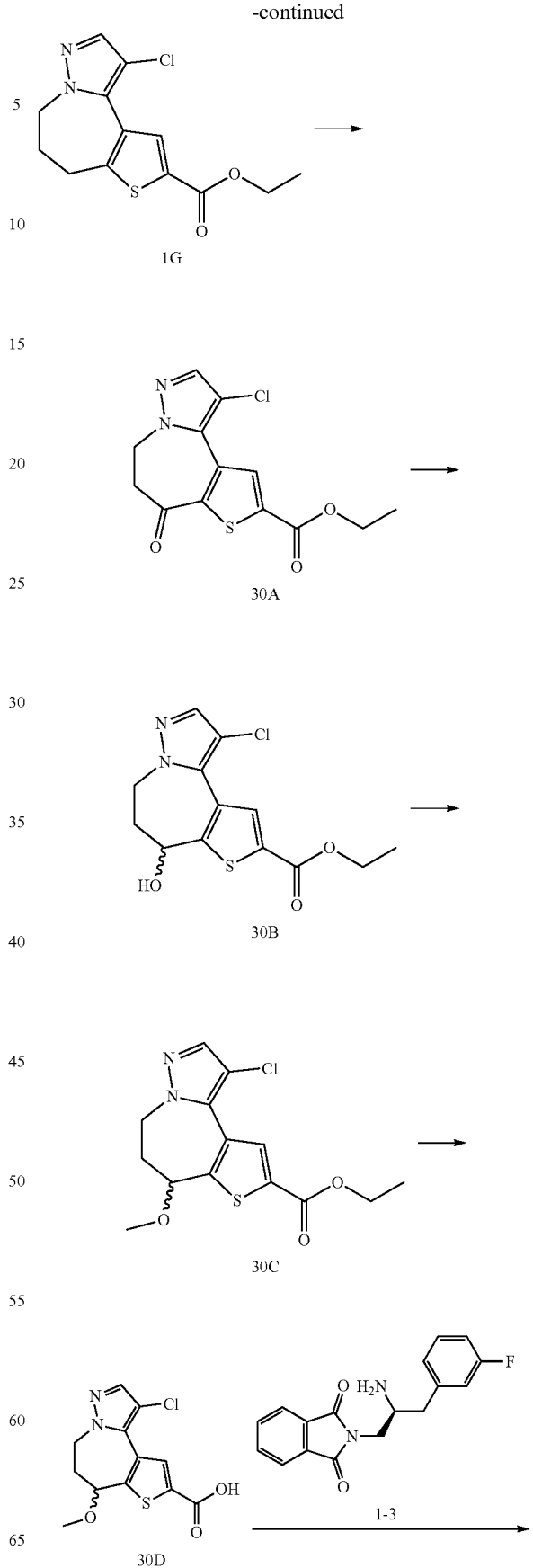

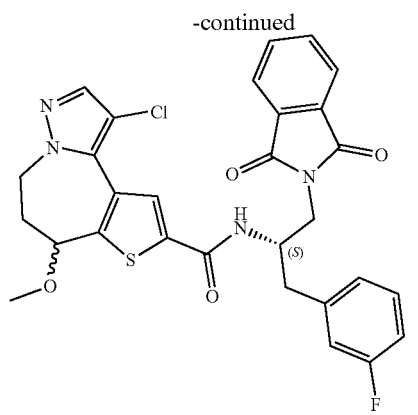

30E

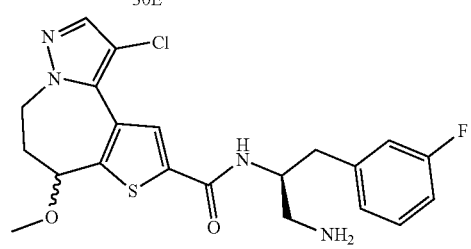

Embodiment 30

Intermediate 30A: ethyl 1-chloro-7-oxo-6,7-dihydro-5H-pyrazolo[1,5-a]thieno[3,2-c]azepine-9-carboxylate CAN (4.69 g, 8.56 mmol) was added to a mixture of intermediate 1G (700 mg, 2.14 mmol) in water (10 mL) and glacial acetic acid (10 mL). The reaction solution was stirred at 15° C. for 1 h. The reaction mixture was diluted with ethyl acetate (30 mL), washed with saturated sodium bicarbonate solution (50 mL*3) and brine (30 mL*2), dried over anhydrous sodium sulfate, filtered and concentrated to give the crude title compound (630 mg), which was used directly in the next step. LCMS (ESI) m/z: 311 (M+1).

Intermediate 30B: ethyl 1-chloro-7-hydroxy-6,7-dihydro-5H-pyrazolo[1,5-a]thieno[3,2-c]azepine-9-carboxylate Sodium borohydride (85.5 mg, 2.26 mmol) was added to a solution of the intermediate 30A (350 mg, 1.13 mmol) in methanol (20 mL) at 0° C. The reaction was stirred at 0° C. for 5 min, then quenched with water (20 mL), and then methanol was evaporated under reduced pressure. The residue was extracted with ethyl acetate (20 mL*2), dried over anhydrous sodium sulfate, filtered and concentrated. The residue was purified by column chromatography to give the title compound (white solid, 245 mg, 69.32% yield). LCMS (ESI) m/z: 313 (M+1).

Intermediate 30C: ethyl 1-chloro-7-methoxy-6,7-dihydro-5H-pyrazolo[1,5-a]thieno[3,2-c]azepine-9-carboxylate Sodium hydride (10 mg, 239.79 μmol) and methyl iodide (41 mg, 287.75 μmol) were added to a solution of intermediate 30B (75 mg, 239.79 μmol) in tetrahydrofuran (5 mL) at 0° C. The reaction solution was stirred at 0° C. for 1 h. After completion of the reaction, it was quenched with saturated ammonium chloride (20 mL). The mixture was extracted with ethyl acetate (10 mL*2), washed with saturated brine solution (20 mL), dried over anhydrous sodium sulfate, filtered and concentrated. The residue was purified by thin layer chromatography to give the title compound (white solid, 40 mg, 46.80% yield). LCMS (ESI) m/z: 327 (M+1).

Intermediate 30D: 1-chloro-7-methoxy-6,7-dihydro-5H-pyrazolo[1,5-a]thieno[3,2-c]azepine-9-carboxylic acid Prepare according to the method as described in the preparation of intermediate 14B, the afforded crude title compound was used directly in the next step without further purification.

Intermediate 30E: 1-chloro-N—((S)-1-(1,3-dioxoisoindolin-2-yl)-3-(3-fluorophenyl)propan-2-yl)-7-methoxy-6,7-dihydro-5H-pyrazolo[1,5-a]thieno[3,2-c]azepine-9-carboxamide Prepare according to the method as described in the preparation of intermediate 14C, the title compound was purified by thin layer preparative chromatography. LCMS (ESI) m/z: 579 (M+1).

Preparation of Embodiment 30

Prepare according to the method as described in embodiment 14. LCMS (ESI) m/z: 449 (M+1). $^1$HNMR (400 MHz, METHANOL-d4) δ ppm 2.36-2.67 (m, 2H), 2.93-3.20 (m, 4H), 3.45 (d, J=1.63 Hz, 3H), 4.28-4.44 (m, 2H), 4.47-4.61 (m, 1H), 4.72-4.77 (m, 1H), 6.94-7.02 (m, 1H), 7.04-7.18 (m, 2H), 7.28-7.37 (m, 1H), 7.49-7.55 (m, 1H), 8.17-8.23 (m, 1H), 8.48-8.57 (m, 1H).

Embodiment 31

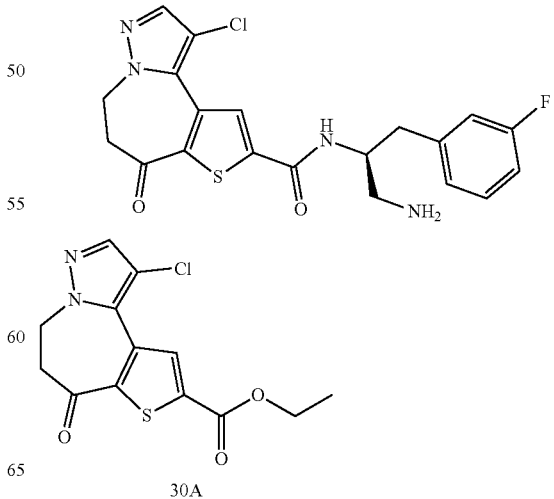

30A

85

-continued

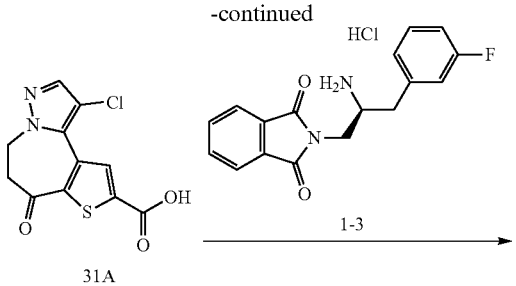

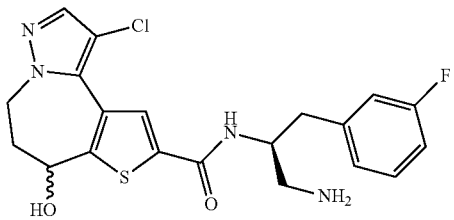 [SMILES: NC[C@H](Cc1cccc(F)c1)NC(=O)c1cc2c(s1)C(O)CCn1ncc(Cl)c1-2]

31A

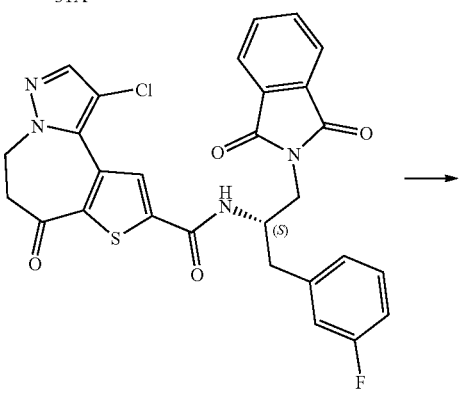

31B

Embodiment 31

Intermediate 31A: 1-chloro-7-oxo-6,7-dihydro-5H-pyrazolo[1,5-a]thieno[3,2-c]azepine-9-carboxylic acid Prepare according to the method as described in the preparation of intermediate 14B, the afforded title compound was used directly in the next step without further purification. LCMS (ESI) m/z: 283 (M+1).

Intermediate 31B: 1-chloro-N—((S)-1-(1,3-dioxoisoindolin-2-yl)-3-(3-fluorophenyl)propan-2-yl)-7-oxo-6,7-dihydro-5H-pyrazolo[1,5-a]thieno [3,2-c] azepine-9-carboxamide Prepare according to the method as described in the preparation of intermediate 14C, the title compound was purified by thin layer preparative chromatography. LCMS (ESI) m/z: 563 (M+1).

Preparation of Embodiment 31

Embodiment 31 was prepared while embodiment 14 was prepared according to the method as described in embodiment 14. LCMS (ESI) m/z: 433(M+1). ¹HNMR (400 MHz, METHANOL-d4) δ ppm 2.91-3.01 (m, 1H), 3.14 (d, J=10.54 Hz, 5H), 4.48-4.58 (m, 1H), 4.63-4.68 (m, 2H), 6.94-7.01 (m, 1H), 7.05-7.15 (m, 2H), 7.27-7.38 (m, 1H), 7.61 (s, 1H), 8.31-8.37 (m, 1H), 8.52-8.54 (m, 1H).

86

Embodiment 32

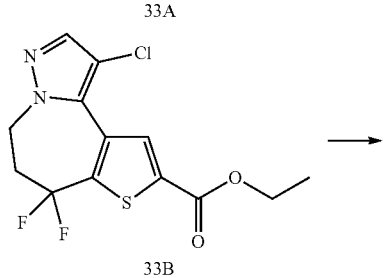

Embodiment 32 was prepared according to the method as described in embodiment 31. LCMS (ESI) m/z: 435 (M+1). ¹HNMR (400 MHz, METHANOL-d4) δ ppm 2.24-2.40 (m, 1H), 2.46-2.61 (m, 1H), 2.90-2.98 (m, 1H), 3.05-3.13 (m, 1H), 3.14-3.29 (m, 2H), 4.38-4.42 (m, 2H), 4.55-4.58 (m, 1H), 5.14-5.17 (m, 1H), 6.92-7.01 (m, 1H), 7.05-7.16 (m, 2H), 7.26-7.36 (m, 1H), 7.54 (s, 1H), 8.13-8.23(m, 1H), 8.50-8.51 (m, 1H).

Embodiment 33

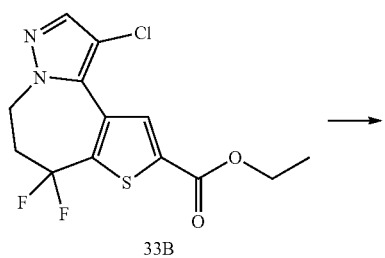

30A

33A

33B

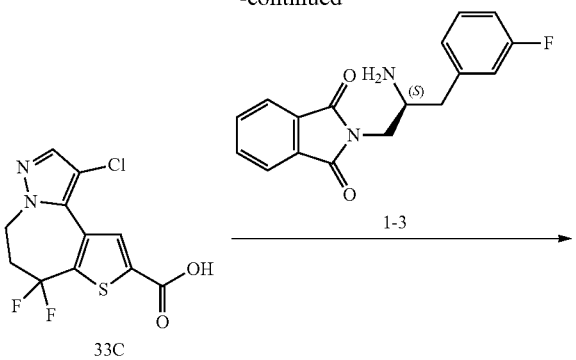

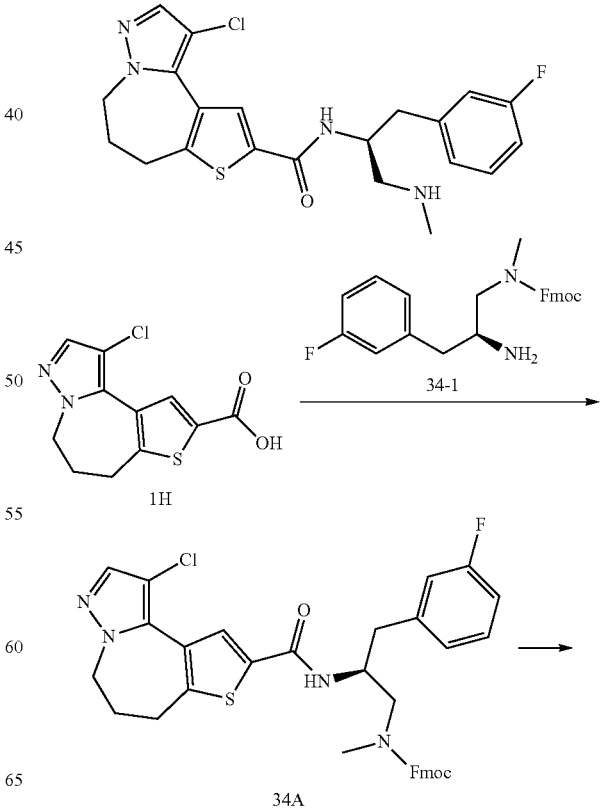

by thin layer chromatography to give the title compound as white solid (35 mg, 72.68% yield). LCMS (ESI) m/z: 333 (M+1).

Intermediate 33C: 1-chloro-7,7-difluoro-6,7-dihydro-5H-pyrazolo[1,5-a]thieno[3,2-c]azepine-9-carboxylic acid Prepare according to the method as described in the preparation of intermediate 14B, the afforded crude title compound was used directly in the next step without further purification. LCMS (ESI) m/z: 305 (M+1).

Intermediate 33D: ethyl 1-chloro-7,7-difluoro-6,7-dihydro-5H-pyrazolo[1,5-a]thieno[3,2-c]azepine-9-carboxylate Prepare according to the method as described in the preparation of intermediate 14C, the title compound was purified by thin layer preparative chromatography. LCMS (ESI) m/z: 585 (M+1).

Preparation of Embodiment 33

Prepare according to the method as described in embodiment 14. LCMS (ESI) m/z: 455 (M+1). $^1$HNMR (400 MHz, METHANOL-d4) δ ppm 2.78-2.92 (m, 2H), 2.94-3.09 (m, 2H), 3.12-3.20 (m, 1H), 3.21-3.28 (m, 1H), 4.48-4.62 (m, 3H), 6.92-7.03 (m, 1H), 7.04-7.17 (m, 2H), 7.27-7.39 (m, 1H), 7.57 (s, 1H), 8.26-8.37 (m, 1H), 8.44-8.60 (m, 1H).

Embodiment 34

Intermediate 33A: ethyl 1'-chloro-5',6'-dihydrospiro[[1,3]dithiolane-2,7'-pyrazolo[1,5-a]thieno[3,2-c]azepine]-9'-carboxylate Ethylenedithiol (27 mg, 282.08 μmol) and p-toluenesulfonic acid (32 mg, 188.05 μmol) were added to a solution of intermediate 30A (60 mg, 188.05 μmol) in toluene (3 mL). After reacted at 100° C. for 1 h, the reaction solution was concentrated. The residue was purified by thin layer chromatography to give the title compound as white solid. LCMS (ESI) m/z: 387 (M+1).

Intermediate 33B: ethyl 1-chloro-7,7-difluoro-6,7-dihydro-5H-pyrazolo[1,5-a]thieno[3,2-c]azepine-9-carboxylate Hydrogen fluoride pyridine (287 mg, 2.89 mmol) and intermediate 33A (59 mg, 144.73 μmol) were added to a solution of iodosuccinimide (260 mg, 1.16 mmol) in dichloromethane (8 mL) at −78° C. under nitrogen. The reaction mixture was reacted at −78° C. to 15° C. for 3 h. Then the mixture was neutralized with a saturated sodium bicarbonate solution, extracted with dichloromethane (20 mL*2), washed with 2 M hydrochloric acid, saturated brine, dried over anhydrous sodium sulfate, filtered and concentrated under reduced pressure to dryness. The residue was purified

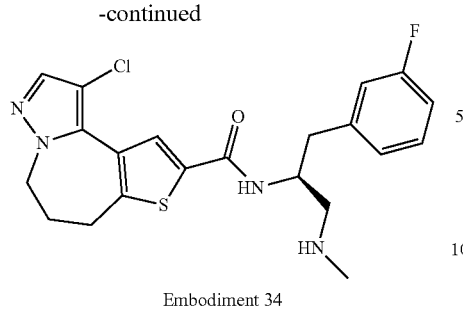

Embodiment 34

Intermediate 34A: (9H-fluoren-9-yl)methyl ((2S)-2-(1-chloro-6,7-dihydro-5H-pyrazolo[1,5-a]thieno[3,2-c]azepine-9-carboxamido)-3-(3-fluorophenyl)propyl)(methyl)carbamate Prepare according to the method as described in the preparation of intermediate 1I, the afforded crude title compound was used directly in the next step without further purification. LCMS (ESI) m/z: 655 (M+1).

Preparation of embodiment 34

A solution of intermediate 34A (50 mg, 65.02 μmol) and diethylamine (24 mg, 325.10 μmol) in DMF (2 mL) was stirred at room temperature for 12 h. After completed, the reaction was diluted with ethyl acetate (20 mL), washed with saturated ammonium chloride solution (10 mL*2) and saturated brine (10 mL*2), dried over anhydrous sodium sulfate, filtered and concentrated. The residue was purified by preparative high performance liquid chromatography (formic acid system) to give embodiment 32 (5 mg, 16.87% yield). LCMS (ESI) m/z: 433 (M+1). $^1$H NMR (400 MHz, METHANOL-d4) δ ppm 2.34 (br. s., 2H), 2.75 (s, 3H), 2.93-3.07 (m, 2H), 3.19 (t, J=6.91 Hz, 2H), 3.22-3.30 (m, 2H), 4.25-4.38 (m, 2H), 4.58-4.63 (m, 1H), 6.89-7.01 (m, 1H), 7.01-7.21 (m, 2H), 7.22-7.37 (m, 1H), 7.51 (s, 1H), 8.13 (s, 1H), 8.42-8.91 (m, 1H).

Embodiment 35

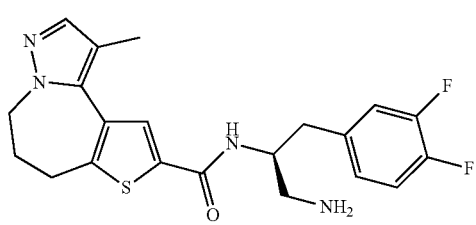

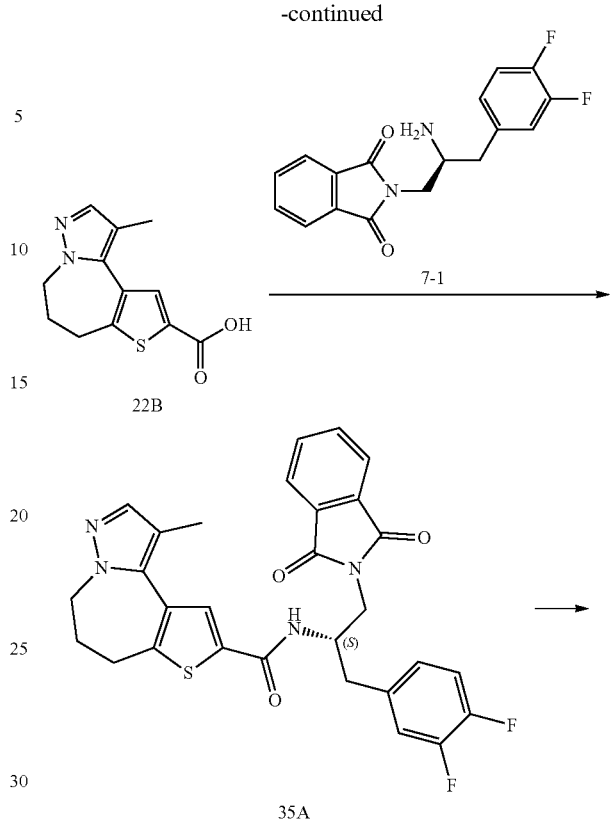

Embodiment 35

Intermediate 35A: N—((S)-1-(3,4-difluorophenyl)-3-(1,3-dioxoisoindolin-2-yl)propan-2-yl)-1-methyl-6,7-dihydro-5H-pyrazolo[1,5-a]thieno[3,2-c]azepine-9-carboxamide Prepare according to the method as described in the preparation of intermediate 14C, the title compound was purified by thin layer preparative chromatography. LCMS (ESI) m/z: 547 (M+1).

Preparation of Embodiment 35

Prepare according to the method as described in embodiment 14. LCMS (ESI) m/z: 417 (M+1). $^1$HNMR (400 MHz, METHANOL-d4) (400 MHz, METHANOL-d4) δ ppm 2.24 (s, 3H), 2.29-2.39 (m, 2H), 2.88-3.05 (m, 2H), 3.09 (s, 3H), 3.19-3.27 (m, 1H), 4.19-4.30 (m, 2H), 4.45-4.57 (m, 1H), 7.05-7.13 (m, 1H), 7.14-7.28 (m, 2H), 7.32-7.37 (m, 1H), 7.79-7.84 (m, 1H), 8.47-8.53 (m, 1H).

Embodiment 36

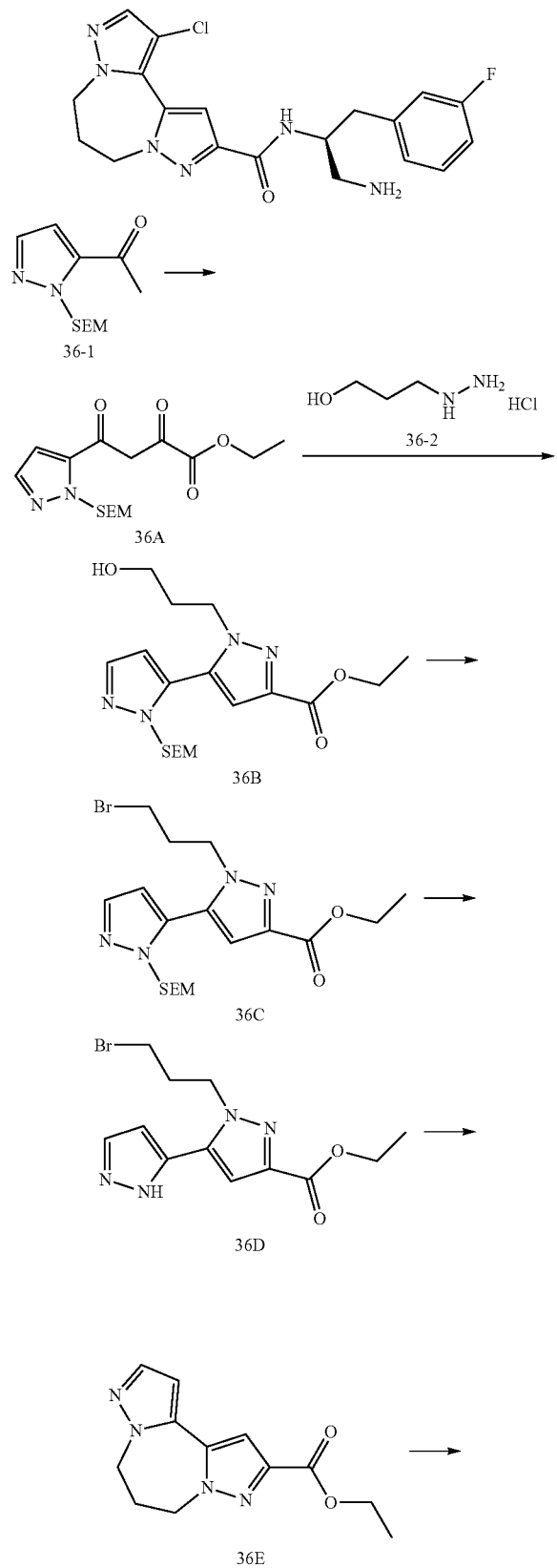

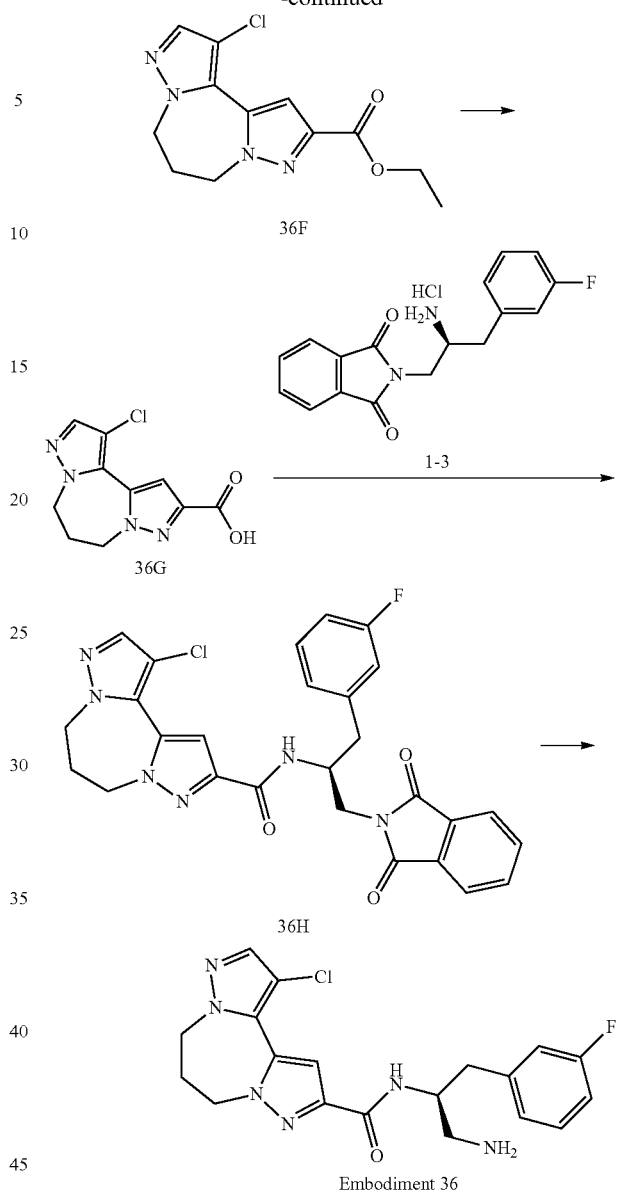

Intermediate 36A: ethyl 2,4-dioxo-4-(1-((2-(trimethylsilyl)ethoxy)methyl)-1H-pyrazol-5-yl)butanoate The sodium (571 mg, 24.84 mmol) was suspended in ethanol (30.00 mL), then diethyl oxalate (3.63 g, 24.84 mmol) and 1-[2-(2-trimethylsilylethoxy)methyl)pyrazol-3-yl]ethanone (3.00 g, 12.42 mmol) were added. The reaction was stirred at 15° C. for 1 h. The mixture was quenched with saturated ammonium chloride, extracted with ethyl acetate. The organic phases were combined, washed with saturated brine, dried over anhydrous sodium sulfate, filtered and concentrated to give the crude title compound (4.2 g), which was used directly in the next step. LCMS (ESI) m/z: 341 (M+1). $^1$HNMR (400 MHz, CHLOROFORM-d) δ ppm 0.04-0.03 (m, 9H), 1.37-1.41 (m, 5H), 3.55-3.68 (m, 2H), 4.36-4.43 (m, 4H), 5.52 (s, 2H), 6.93-7.00 (m, 1H), 7.27-7.28 (m, 1H), 7.57-7.70 (m, 1H).

Intermediate 36B: ethyl 2-(3-hydroxypropyl)-2'-((2-(trimethylsilyl) ethoxy)methyl)-2H,2'H-[3,3'-bipyrazole]-5-carboxylate Triethylamine (4.41 g, 43.60 mmol) was added to a solution of intermediate 36A (3.60 g, 8.72 mmol) and 3-mercaptopropan-1-ol (3.31 g, 26.16 mmol) in ethanol (50.00 mL). Then, the mixture was stirred at 78° C. for 0.5 h, and the ethanol was evaporated under reduced pressure. The residue was added with saturated ammonium chloride (200 mL), extracted with ethyl acetate (50 mL*2), dried over anhydrous sodium sulfate, filtered and concentrated to give crude title compound (3.32 g) as yellow oil, which was used directly in the next step. LCMS (ESI) m/z: 395 (M+1).

Intermediate 36C: ethyl 2-(3-bromopropyl)-2'-((2-(trimethylsilyl)ethoxy) methyl)-2H,2'H-[3,3'-bipyrazole]-5-carboxylate Prepare according to the method as described in preparation of intermediate 1E, the title compound was purified by column chromatography. LCMS (ESI) m/z: 459 (M+1).

Intermediate 36D: ethyl 2-(3-bromopropyl)-2H,2'H-[3,3'-bipyrazole]-5-carboxylate Trifluoroacetic acid (7 mL, 94.19 mmol) was added to a solution of intermediate 36C (2.48 g, 4.71 mmol) in dichloromethane (8 mL). The reaction mixture was stirred at 15° C. for 16 h, and concentrated to give the crude title compound (1.54 g). LCMS (ESI) m/z: 327 (M+1).

Intermediate 36E: ethyl 6,7-dihydro-5H-dipyrazolo[1,5-a:5',1'-c][1,4]diazepine-2-carboxylate Cesium carbonate (4.60 g, 14.13 mmol) was added to a solution of intermediate 36D (1.54 g, 4.71 mmol) in ethanol (20 mL). The reaction mixture was stirred at 15° C. for 0.5 h, and the ethanol was evaporated under reduced pressure. The residue was diluted with ethyl acetate (30 mL), washed with water, dried over anhydrous sodium sulfate, filtered and concentrated to give crude title compound as yellow oil. The crude product was purified by thin layer preparative chromatography to give the title compound (168 mg, 13.21% yield). LCMS (ESI) m/z: 247 (M+1). $^1$H NMR (400 MHz, CHLOROFORM-d) δ ppm 1.43 (s, 3H), 2.47-2.58 (m, 2H), 4.38-4.49 (m, 2H), 4.54-4.70 (m, 4H), 6.52-6.64 (m, 1H), 7.07 (s, 1H), 7.47-7.57 (m, 1H).

Intermediate 36F: ethyl 11-chloro-6,7-dihydro-5H-dipyrazolo[1,5-a:5',1'-c][1,4]diazepine-2-carboxylate NCS (77 mg, 577.86 μmol) and glacial acetic acid HOAc (35 mg, 577.86 μmol) were added to a solution of intermediate 36E (156 mg, 577.86 μmol) in tetrahydrofuran (5 mL). The reaction mixture was stirred at 60° C. for 24 h and concentrated under reduced pressure. The residue was diluted with ethyl acetate (10 mL), washed with saturated brine (20 mL*2), dried over anhydrous sodium sulfate, filtered and concentrated to give crude title compound (130 mg) as yellow oil, which was used directly in the next step. LCMS (ESI) m/z: 281 (M+1). $^1$H NMR (400 MHz, CHLOROFORM-d) δ ppm 1.33-1.38 (m, 3H), 2.39-2.51 (m, 2H), 4.34-4.41 (m, 2H), 4.41-4.46 (m, 2H), 4.51-4.57 (m, 2H), 7.43 (s, 1H), 7.45-7.47 (m, 1H).

Intermediate 36G: 11-chloro-6,7-dihydro-5H-dipyrazolo[1,5-a:5',1'-c][1,4]diazepine-2-carboxylic acid Sodium hydroxide (74 mg, 1.85 mmol) was added to a mixture of intermediate 36F (130 mg, 463.11 mmol) in methanol (2 mL), THF (2 mL) and water (2 mL). The reaction solution was stirred at 15° C. for 0.5 h. Methanol and tetrahydrofuran were evaporated under reduced pressure. The residue was adjusted to pH=3-4 with diluted hydrochloric acid (1 N), extracted with ethyl acetate (10 mL*2), washed with saturated brine (20 mL*2), dried over anhydrous sodium sulfate, filtered and concentrated to give crude title compound (130 mg) as yellow oil, which was used directly in the next step. LCMS (ESI) m/z: 253 (M+1).

Intermediate 36H: 11-chloro-N—((S)-1-(1,3-dioxoisoindolin-2-yl)-3-(3-fluorophenyl)propan-2-yl)-6,7-dihydro-5H-dipyrazolo[1,5-a: 5',1'-c][1,4]diazepine-2-carboxamide Prepare according to the method as described in the preparation of intermediate 14C, the title compound was purified by thin layer preparative chromatography. LCMS (ESI) m/z: 533 (M+1). $^1$H NMR (400 MHz, CHLOROFORM-d) δ ppm 2.45-2.59 (m, 2H), 2.93-3.12 (m, 2H), 3.83-3.90 (m, 2H), 4.47-4.57 (m, 4H), 4.71-4.85 (m, 1H), 6.89-6.97 (m, 1H), 6.99-7.05 (m, 1H), 7.07-7.15 (m, 2H), 7.27-7.31 (m, 1H), 7.36-7.40 (m, 1H), 7.47-7.51 (m, 1H), 7.66-7.74 (m, 2H), 7.78-7.86 (m, 2H).

Preparation of Embodiment 36

Prepare according to the method as described in embodiment 14. LCMS (ESI) m/z: 403 (M+1). $^1$H NMR (400 MHz, METHANOL-d4) δ ppm 2.45-2.58 (m, 2H), 2.98-3.05 (m, 2H), 3.11-3.25 (m, 2H), 4.55-4.66 (m, 5H), 6.93-7.01 (m, 1H), 7.05-7.16 (m, 2H), 7.28-7.36 (m, 1H), 7.48-7.52 (m, 1H), 7.57-7.62 (m, 1H), 8.41-8.57 (m, 1H).

Embodiment 37

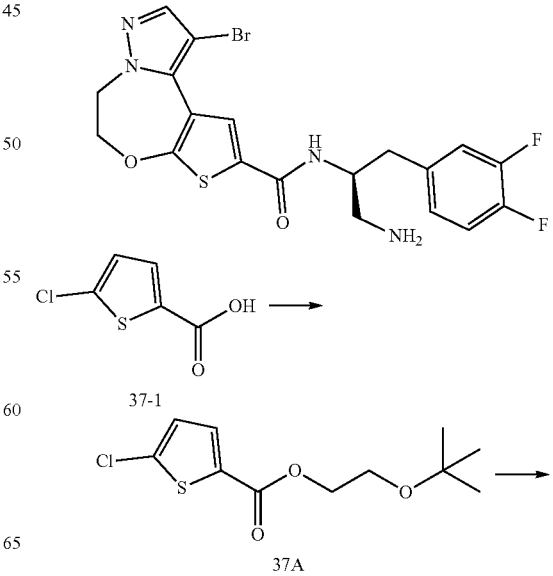

-continued

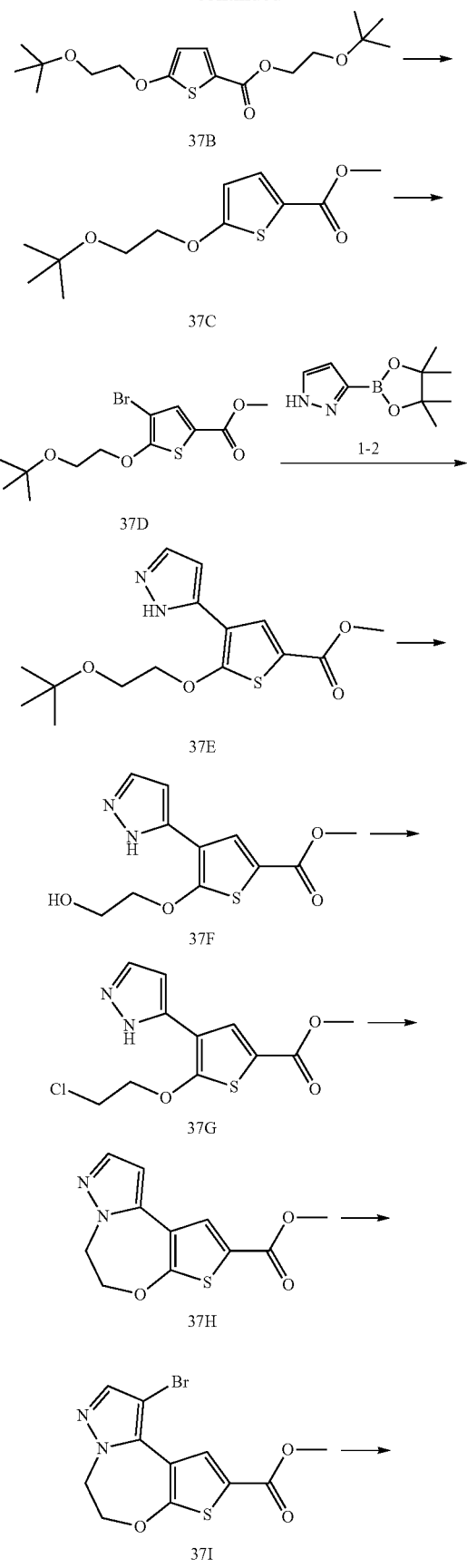

-continued

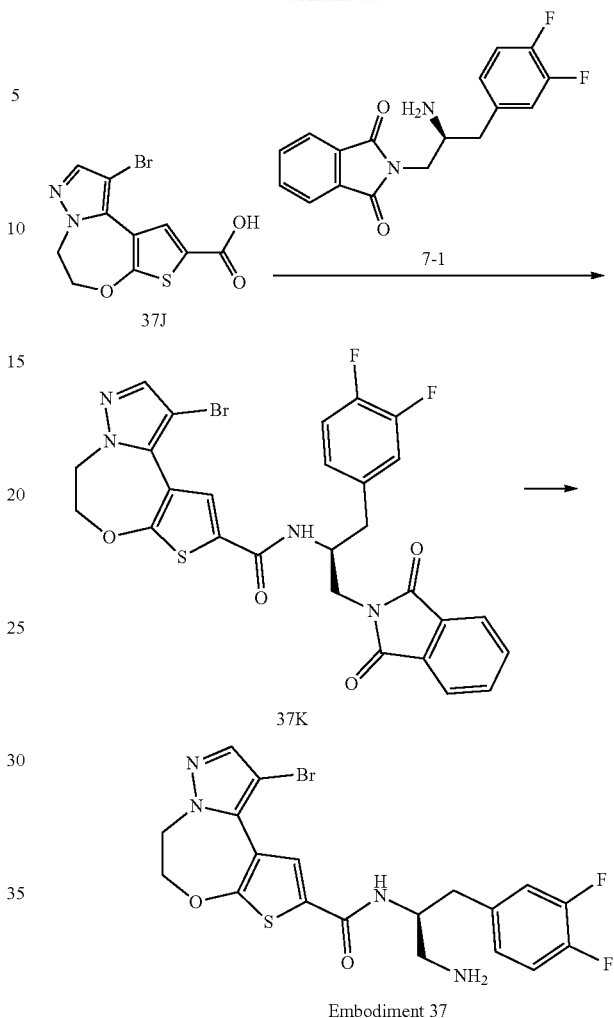

Intermediate 37A: 2-(tert-butoxy)ethyl 5-chlorothiophene-2-carboxylate

Oxalyl chloride (5.43 g, 42.80 mmol, 3.74 mL) was added dropwise to a solution of 5-chlorothiophene-2-carboxylic acid (5.80 g, 35.67 mmol) in dichloroethane (60.00 mL) at 0° C., then DMF (100.00 μL) was added, and the reaction mixture was stirred at 20° C. for 2 h. The reaction solution was then concentrated to dryness. The residue was redissolved in tetrahydrofuran (30 mL), then a mixed solvent of 2-t-butyloxyethyl alcohol (4.22 g, 35.67 mmol, 4.68 mL) and triethylamine (10.83 g, 107.01 mmol, 14.83 mL) in tetrahydrofuran (50.00 mL) were added dropwise at 0° C., and the reaction mixture was stirred at 20° C. for 2 h. After TLC showed the reaction finished, the reaction mixture was concentrated. The residue was redissolved in ethyl acetate (50 mL), washed with saturated brine, dried over anhydrous sodium sulfate, filtered and concentrated. The residue was purified by column chromatography to give the title compound (9.16 g, 95.56% yield) as colorless oil. LCMS (ESI) m/z: 263 (M+1). $^{1}$HNMR (400 MHz, CHLOROFORM-d) δ ppm 1.24 (s, 9H), 3.56-3.71 (m, 2H), 4.29-4.43 (m, 2H), 6.95 (d, J=4.02 Hz, 1H), 7.62 (d, J=4.14 Hz, 1H).

Intermediate 37B: 2-(tert-butoxy)ethyl 5-(2-(tert-butoxy)ethoxy) thiophene-2-carboxylate Sodium hydride (223 mg, 5.58 mmol, 60% purity) was added to a solution of 2-tert-butyloxyethyl alcohol (660 mg, 5.58 mmol) in DMF (10.00 mL) at 20° C. Intermediate 37B (1.00 g, 3.72 mmol) was then added. The reaction solution was stirred at 20 to 65° C. for 1.5 h under nitrogen. After TLC showed the reaction finished, the mixture was quenched with glacial acetic acid (1 mL), extracted with ethyl acetate (30 mL), washed with saturated sodium bicarbonate solution (30 mL) and saturated brine (30 mL*2), dried over anhydrous sodium sulfate, filtered and concentrated. The residue was purified by column chromatography to give the title compound (813 mg, 62.27% yield) as white solid. LCMS (ESI) m/z: 345 (M+1). 1HNMR (400 MHz, CHLOROFORM-d) δ ppm 1.2-1.3 (m, 18H), 3.6-3.7 (m, 2H), 3.71-3.76 (m, 2H), 4.17-4.26 (m, 2H), 4.30-4.39 (m, 2H), 6.27 (d, J=4.14 Hz, 1H), 7.55 (d, J=4.14 Hz, 1H).

Intermediate 37C: methyl 5-(2-(tert-butoxy)ethoxy)thiophene-2-carboxylate

Sodium methoxide (138 mg, 2.55 mmol) was added to a solution of intermediate 37B (813 mg, 2.32 mmol) in methanol (10.00 mL). The reaction solution was stirred at 65° C. for 1 h under nitrogen. After TLC showed the reaction finished, the mixture was quenched with glacial acetic acid (0.2 mL), and the methanol was evaporated under reduced pressure. The residue was diluted with ethyl acetate (20 mL), washed with saturated sodium bicarbonate solution (10 mL) and saturated brine (30 mL*2), dried over anhydrous sodium sulfate, filtered and concentrated to give the title compound (600 mg, crude) as white solid. LCMS (ESI) m/z: 259 (M+1). $^1$HNMR (400 MHz, CHLOROFORM-d) δ ppm 1.25 (s, 9H), 3.72-3.76 (m, 2H), 3.86 (s, 3H), 4.18-4.25 (m, 2H), 6.27 (d, J=4.27 Hz, 1H), 7.54 (d, J=4.27 Hz, 1H).

Intermediate 37D: methyl 4-bromo-5-(2-(tert-butoxy)ethoxy)thiophene-2-carboxylate NBS (496 mg, 2.79 mmol) was added to a solution of intermediate 37C (600 mg, 2.32 mmol) in THF (10.00 mL). The reaction solution was stirred at 20° C. for 1 h under nitrogen. After TLC showed the reaction finished, the mixture was concentrated. The residue was purified by column chromatography to give title compound (700 mg, 88.69 yield) as colorless transparent oil. LCMS (ESI) m/z: 337 (M+1). $^1$HNMR (400 MHz, CHLOROFORM-d) δ ppm 1.16 (s, 9H), 3.68 (t, J=5.01 Hz, 2H), 3.78 (s, 3H), 4.10-4.27 (m, 2H), 7.47(s, 1H).

Intermediate 37E: methyl 5-(2-(tert-butoxy)ethoxy)-4-(1H-pyrazol-5-yl) thiophene-2-carboxylate Sodium bicarbonate (310 mg, 3.69 mmol) and bis(tri-tert-butylphosphine)palladium (113 mg, 221.10 μmol) were added to a solution of intermediate 37D (500 mg, 1.47 mmol) and intermediate 1-2 (378 mg, 1.62 mmol, hydrochloride) in 1,4-dioxane (3 mL) and water (0.7 mL). The reaction solution was reacted at 110° C. for 0.5 h under nitrogen atmosphere. After TLC showed the reaction finished, the mixture was concentrated. The residue was diluted with ethyl acetate (15 mL), washed with water (10 mL) and saturated brine (10 mL), dried over anhydrous sodium sulfate and filtered. The residue was purified by column chromatography to give title compound (610 mg, 91.37 yield) as colorless transparent oil.

Intermediate 37F: methyl 5-(2-hydroxyethoxy)-4-(1H-pyrazol-5-yl) thiophene-2-carboxylate Hydrochloric acid-methanol solution (5 mL, 4 moles per liter) was added to a solution of intermediate 37E (610 mg, 1.88 mmol) in methanol (5 mL). The reaction solution was reacted at 50° C. for 0.5 h. After TLC showed the reaction finished, the mixture was concentrated. The residue was washed with dichloromethane (10 mL) to give the title compound (396 mg, 74.14 yield) as white solid. LCMS (ESI) m/z: 269 (M+1). $^1$HNMR (400 MHz, DMSO-d6) δ ppm 3.87 (s, 5H), 4.33 (br s, 2H), 5.03-5.36 (m, 1H), 6.76 (s, 1H), 7.58 (br s, 1H), 7.93-8.32 (m, 1H), 12.64-13.17 (m, 1H).

Intermediate 37G: methyl 5-(2-chloroethoxy)-4-(1H-pyrazol-5-yl) thiophene-2-carboxylate Pyridine (14 mg, 175.98 μmol) and dichlorosulfoxide (23 mg, 193.58 μmol) were added to a solution of intermediate 37F (50 mg, 175.98 μmol) in chloroform (5 mL) at −40° C. The reaction solution was stirred at −40-60° C. for 1 h. After the reaction was completed, the mixture was diluted with dichloromethane (10 mL), washed with water (10 mL), 1 N hydrochloric acid (10 mL) and saturated brine (10 mL), dried over anhydrous sodium sulfate, filtered and concentrated to give the title compound (50 mg, crude) as white solid.

Intermediate 37H: methyl 5,6-dihydropyrazolo[1,5-d]thieno[3,2-f][1,4]oxazepine-2-carboxylate Prepare according to the method as described in embodiment 1F. LCMS (ESI) m/z: 251 (M+1). $^1$HNMR (400 MHz, CHLOROFORM-d) δ ppm 3.90 (s, 3H), 4.59-4.65 (m, 2H), 4.71-4.78 (m, 2H), 6.44 (d, J=2.01 Hz, 1H), 7.48 (d, J=2.01 Hz, 1H), 7.74 (s, 1H).

Intermediate 37I: methyl 10-bromo-5,6-dihydropyrazolo[1,5-d]thieno[3,2-f][1,4]oxazepine-2-carboxylate Prepare according to the method as described in embodiment 14A. $^1$HNMR (400 MHz, CHLOROFORM-d) δ ppm 3.81 (s, 3H), 4.49-4.54 (m, 2H), 4.59-4.64 (m, 2H), 7.39 (s, 1H), 8.38 (s, 1H).

Intermediate 37J: 10-bromo-5,6-dihydropyrazolo[1,5-d]thieno[3,2-f][1,4]oxazepine-2-carboxylic acid Prepare according to the method as described in embodiment 36G.

Intermediate 37K: 10-bromo-N—((S)-1-(3,4-difluorophenyl)-3-(1,3-dioxoisoindolin-2-yl)propan-2-yl)-5,6-dihydropyrazolo[1,5-d]thieno[3,2-f][1,4]oxazepine-2-carboxamide Prepare according to the method as described in embodiment 14C. LCMS (ESI) m/z: 613 (M+1). $^1$HNMR (400 MHz, DMSO-d6) δ ppm 2.92-3.02 (m, 2H), 3.83-3.91 (m, 2H), 4.39-4.81 (m, 5H), 7.19 (br d, J=4.65 Hz, 1H), 7.29-7.49 (m, 2H), 7.68 (s, 1H), 7.85-7.98 (m, 4H), 8.09 (s, 1H), 8.49 (d, J=9.05 Hz, 1H).

Preparation of Embodiment 37

Prepare according to the method as described in embodiment 14. LCMS (ESI) m/z: 483 (M+1). $^1$HNMR (400 MHz, METHANOL-d4) δ ppm 2.86-2.96 (m, 1H), 2.96-3.05 (m, 1H), 3.06-3.15 (m, 1H), 3.17-3.25 (m, 1H), 4.42-4.53 (m, 1H), 4.56-4.66 (m, 2H), 4.66-4.73 (m, 2H), 7.10 (br d, J=2.13 Hz, 1H), 7.14-7.29 (m, 2H), 7.52 (s, 1H), 8.25 (s, 1H), 8.54 (br s, 1H).

Embodiment 38

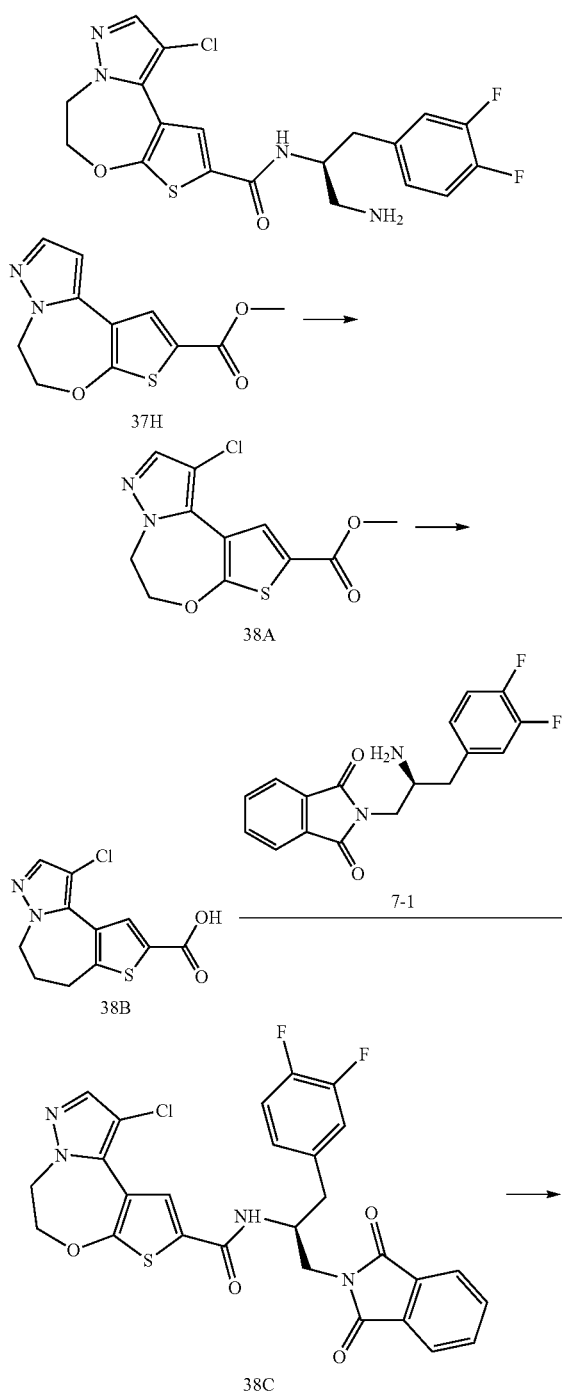

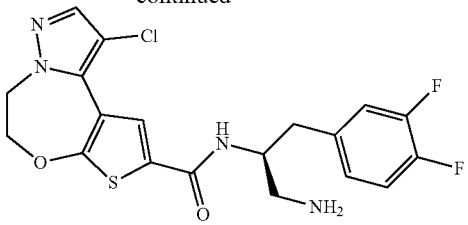

Embodiment 38

Intermediate 38A: methyl 10-chloro-5,6-dihydropyrazolo[1,5-d]thieno[3,2-f][1,4]oxazepine-2-carboxylate NCS (35 mg, 263.71 μmol) was added to a solution of the intermediate 37H (60 mg, 239.74 μmol, crude) in tetrahydrofuran (3 mL), and the mixture was stirred at 40° C. for 1 h. After TLC showed the reaction finished, the mixture was concentrated. The residue was diluted with ethyl acetate (10 mL), washed with saturated brine (10 mL*2), dried over anhydrous sodium sulfate, filtered and concentrated to give the title compound (70 mg, crude) as white solid, which was used directly in the next step. LCMS (ESI) m/z: 285 (M+1).

Intermediate 38B: 10-chloro-5,6-dihydropyrazolo[1,5-d]thieno[3,2-f][1,4]oxazepine-2-carboxylic acid Prepare according to the method as described in embodiment 14B. LCMS (ESI) m/z: 271 (M+1).

Intermediate 38C: 10-chloro-N—((S)-1-(3,4-difluorophenyl)-3-(1,3-dioxoisoindolin-2-yl)propan-2-yl)-5,6-dihydropyrazolo[1,5-d]thieno[3,2-f][1,4]oxazepine-2-carboxamide Prepare according to the method as described in embodiment 14C. LCMS (ESI) m/z: 569 (M+1).

Preparation of Embodiment 38

Prepare according to the method as described in embodiment 14. LCMS (ESI) m/z: 439 (M+1). $^1$H NMR (400 MHz, METHANOL-d4) δ ppm 2.85-2.95 (m, 1H), 2.96-3.03 (m, 1H), 3.05-3.14 (m, 1H), 3.16-3.25 (m, 1H), 4.42-4.51 (m, 1H), 4.61-4.64 (m, 2H), 4.67-4.72 (m, 2H), 7.08 (ddd, J=6.12, 4.11, 2.32 Hz, 1H), 7.13-7.28 (m, 2H), 7.51 (s, 1H), 8.20 (s, 1H), 8.53 (brs, 1H).

Embodiment 39

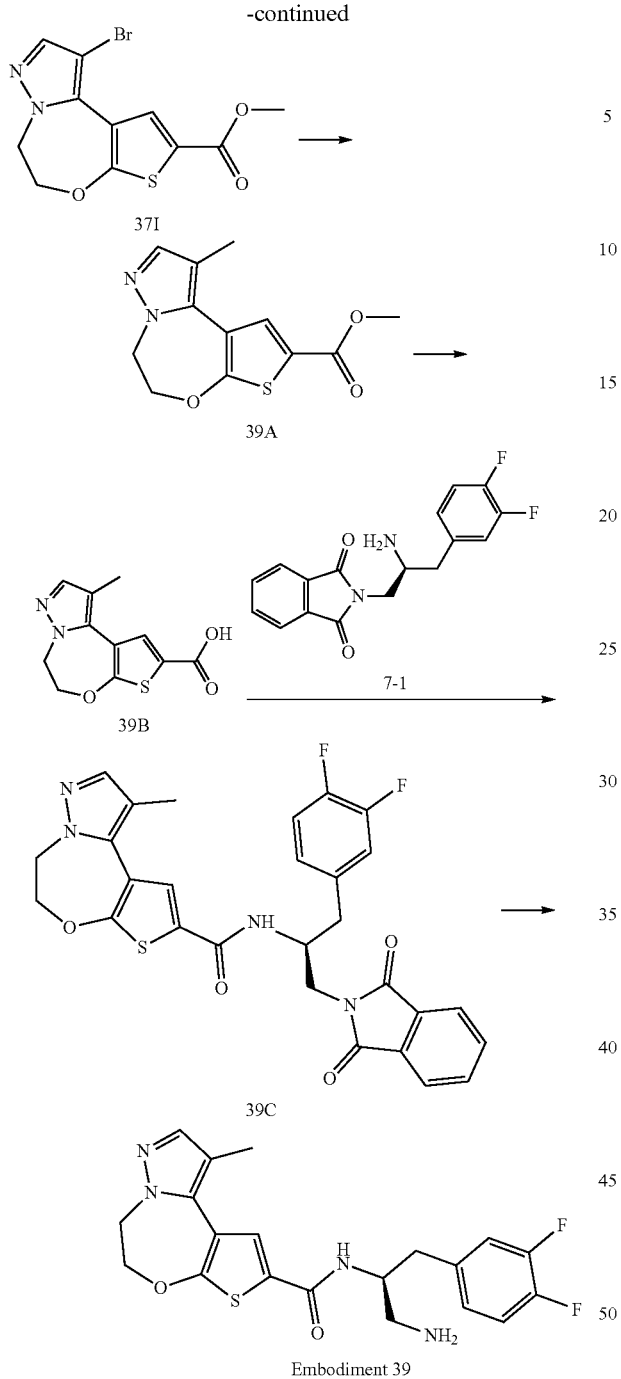

with saturated brine (25 mL*2), dried over anhydrous sodium sulfate, filtered and concentrated. The residue was purified by preparative thin layer chromatography to give the title compound as a yellow solid (180 mg). LCMS (ESI) m/z: 265 (M+1).

Intermediate 39B: 10-methyl-5,6-dihydropyrazolo [1,5-d]thieno[3,2-f][1,4]oxazepine-2-carboxylic acid Prepare according to the method as described in embodiment 36G. LCMS (ESI) m/z: 251 (M+1).

Intermediate 39C: N—((S)-1-(3,4-difluorophenyl)-3-(1,3-dioxoisoindolin -2-yl)propan-2-yl)-10-methyl-5,6-dihydropyrazolo[1,5-d]thieno[3,2-f][1,4] oxazepine-2-carboxamide Prepare according to the method as described in embodiment 14C. LCMS (ESI) m/z: 549 (M+1).

Preparation of Embodiment 39

Prepare according to the method as described in embodiment 14. LCMS (ESI) m/z: 419 (M+1). ¹H NMR (400 MHz, METHANOL-d4) δ ppm 2.31 (s, 3H), 2.88-3.04 (m, 2H), 3.12 (br d, J=9.90 Hz, 1H), 3.19 (br d, J=3.79 Hz, 1H), 4.45 (br s, 1H), 4.56-4.67 (m, 4H), 7.09 (br d, J=1.59 Hz, 1H), 7.15-7.26 (m, 2H), 7.32 (s, 1H), 7.76 (s, 1H), 8.49-8.60 (m, 1H).

Embodiment 40

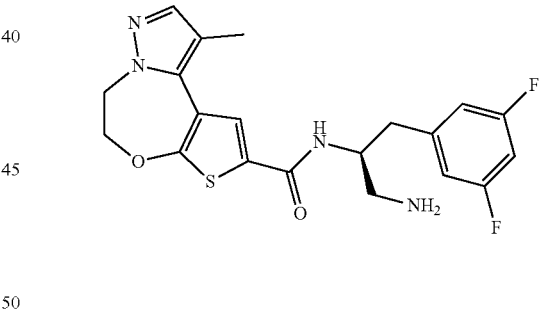

Intermediate 39A: methyl 10-methyl-5,6-dihydropyrazolo[1,5-d]thieno[3,2-f][1,4]oxazepine-2-carboxylate Methylboronic acid (493 mg, 8.24 mmol), potassium carbonate (854 mg, 6.18 mmol) and Pd(dppf)Cl₂.CH₂Cl₂ (168 mg, 206.00 μmol) were added to a solution of intermediate 37I (339 mg, 1.03 mmol) in DMF (6.00 mL) at 20° C. under nitrogen. The reaction was reacted at 100° C. for 12 h. After TLC showed the reaction finished, the mixture was filtered. Water (50 mL) was added to the filtrate, and the mixture was extracted with ethyl acetate (30 mL*3), washed

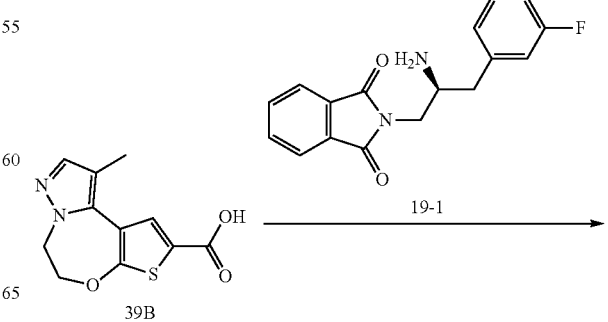

-continued

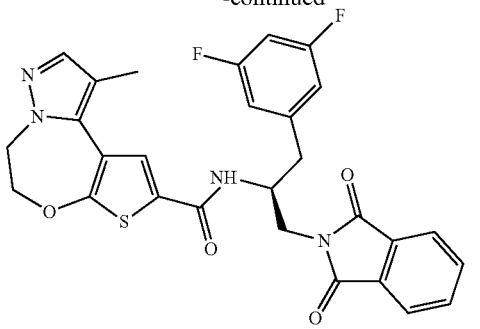

40A

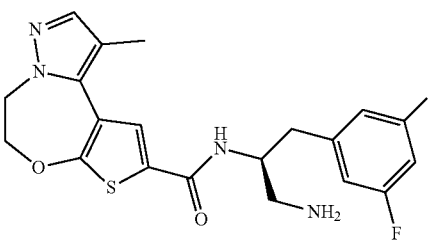

Embodiment 40

Intermediate 40A: N—((S)-1-(3,5-difluorophenyl)-3-(1,3-dioxoisoindolin-2-yl)propan-2-yl)-10-methyl-5,6-dihydropyrazolo[1,5-d]thieno[3,2-f][1,4]oxazepine-2-carboxamide Diisopropylethylamine (99 mg, 766.35 μmol), TBTU (121 mg, 377.59 μmol) and (S)-2-(2-amino-3-(3,5-difluorophenyl)propyl)isoindoline-1,3-dione (100 mg, 276.9 μmol) were added to a solution of intermediate 39B (90 mg, 251.73 μmol) in DMF (5 mL) at 20° C. under nitrogen. The mixture was reacted at 20° C. for 20 min. After LC-MS showed the reaction finished, ethyl acetate (100 mL) was added. The mixture was washed with saturated brine (50 mL*3), and the organic phase was dried over anhydrous sodium sulfate, filtered and concentrated. The residue was washed with methanol (30 mL) to give title compound (50 mg) as white solid. LCMS (ESI) m/z: 549 (M+1).

Preparation of Embodiment 40

Prepare according to the method as described in embodiment 4. LCMS (ESI) m/z: 419 (M+1). ¹H NMR (400 MHz, METHANOL-d4) δ ppm 2.31 (s, 3H), 2.96 (br d, J=9.41 Hz, 1H), 3.01-3.13 (m, 2H), 3.17-3.24 (m, 1H), 4.44-4.52 (m, 1H), 4.56-4.66 (m, 4H), 6.83 (s, 1H), 6.93 (br d, J=6.24 Hz, 2H), 7.32 (s, 1H), 7.76 (s, 1H), 8.54 (br s, 1H).

Embodiment 41

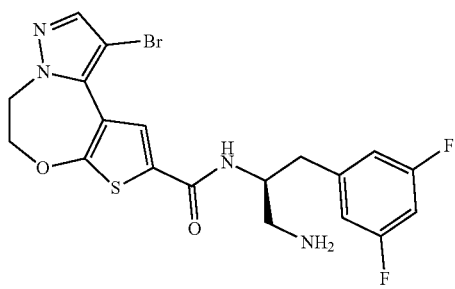

-continued

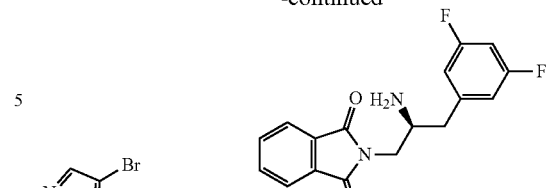

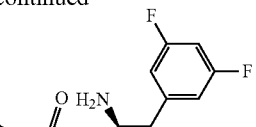

37J

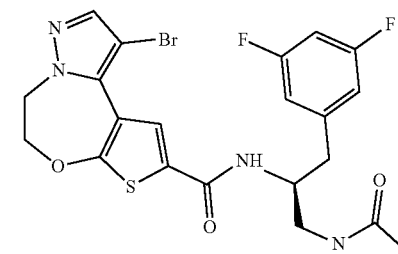

41A

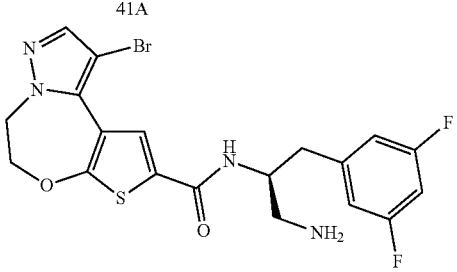

Embodiment 41

Intermediate 41A: 10-bromo-N—((S)-1-(3,5-difluorophenyl)-3-(1,3-dioxoisoindolin-2-yl)propan-2-yl)-5,6-dihydropyrazolo[1,5-d]thieno[3,2-f][1,4]oxazepine-2-carboxamide Diisopropylethylamine (103 mg, 766.35 μmol) and TBTU (76 mg, 237.99 μmol) were added to a solution of intermediate 37J (50 mg, 158.66 μmol) and (S)-2-(2-amino-3-(3,5-difluorophenyl)propyl)isoindoline-1,3-dione (62 mg, 174.53 μmol) in DMF (2 mL) at 0° C. under nitrogen. The mixture was reacted at 25° C. for 2 h. After LC-MS showed the reaction finished, the reaction was quenched with water (10 mL). The mixture was extracted with ethyl acetate (10 mL*2), washed with saturated brine (10 mL*2), and the organic phase was dried over anhydrous sodium sulfate, filtered and concentrated to give the title compound (90 mg, crude) as white solid. LCMS (ESI) m/z: 613(M+1).

Preparation of Embodiment 41

The hydrazine hydrate (147 mg, 2.93 mmol) was added to a solution of the intermediate 41A (90 mg, crude) in methanol (5 mL), and the mixture was stirred at 25° C. for 2 h. After LC-MS showed the reaction finished, the solvent was removed in vacuo. The residue was purified by preparative HPLC to give the title compound (36 mg, 46.35% yield). LCMS (ESI) m/z: 483 (M+1). ¹H NMR (METHANOL-d4)

δ ppm 2.88-2.97 (m, 1H), 3.00-3.12 (m, 2H), 3.16-3.24 (m, 1H), 4.61 (s, 3H), 4.68-4.74 (m, 2H), 6.79-6.86 (m, 1H), 6.93 (br d, J=6.15 Hz, 2H), 7.52 (s, 1H), 8.25 (s, 1H), 8.53 (s, 1H).

Embodiment 42

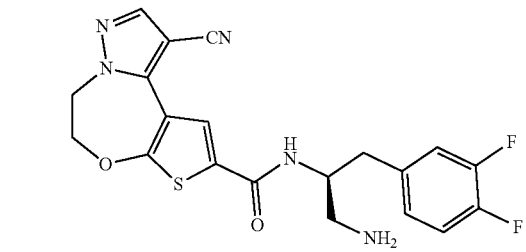

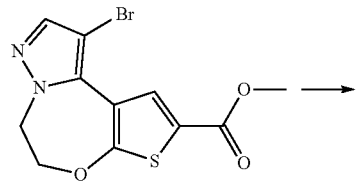
37I

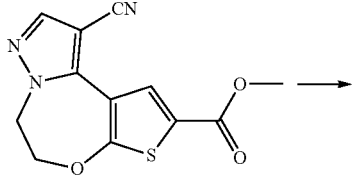
42A

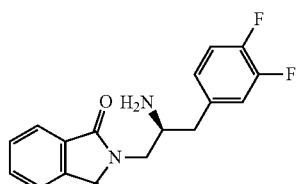
7-1

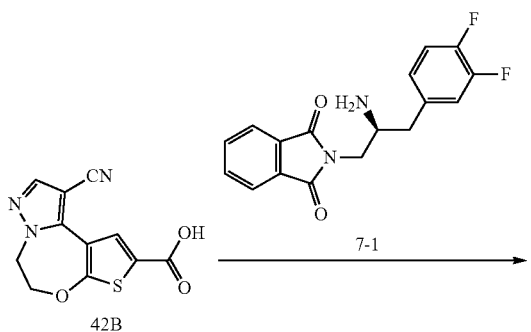
42B

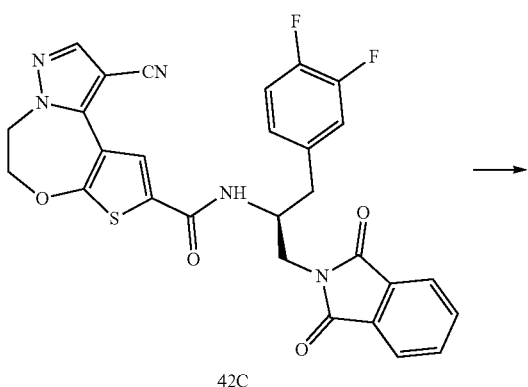
42C

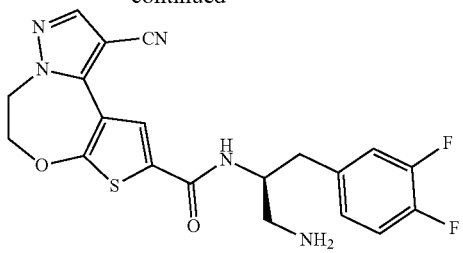
Embodiment 42

Intermediate 42A: methyl 10-cyano-5,6-dihydropyrazolo[1,5-d]thieno[3,2-f][1,4]oxazepine-2-carboxylate Prepare according to the method as described in embodiment 26A. LCMS (ESI) m/z: 276 (M+1).

Intermediate 42B: 10-cyano-5,6-dihydropyrazolo[1,5-d]thieno[3,2-f][1,4]oxazepine-2-carboxylic acid Prepare according to the method as described in embodiment 14B. LCMS (ESI) m/z: 262 (M+1).

Intermediate 42C: 10-cyano-N—((S)-1-(3,4-difluorophenyl)-3-(1,3-dioxoisoindolin-2-yl)propan-2-yl)-5,6-dihydropyrazolo[1,5-d]thieno[3,2-f][1,4]oxazepine-2-carboxamide Prepare according to the method as described in embodiment 41A. LCMS (ESI) m/z: 560 (M+1).

Preparation of Embodiment 42

Prepare according to the method as described in embodiment 15. LCMS (ESI) m/z: 430 (M+1). $^1$H NMR (400 MHz, METHANOL-d4) δ ppm 2.89-2.97 (m, 1H), 3.00-3.12 (m, 2H), 3.16-3.22 (m, 1H), 4.43-4.52 (m, 1H), 4.68 (dd, J=5.08, 2.20 Hz, 2H), 4.79 (dd, J=5.08, 1.94 Hz, 2H), 6.77-6.85 (m, 1H), 6.93 (dd, J=8.22, 2.20 Hz, 2H), 7.92 (s, 1H), 8.07 (s, 1H), 8.54 (br s, 1H).

Embodiment 43

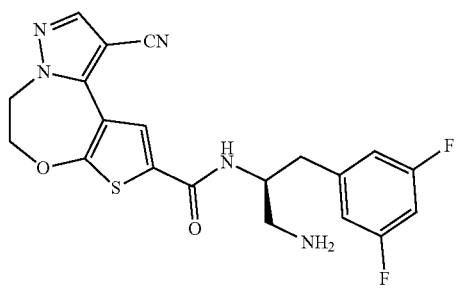

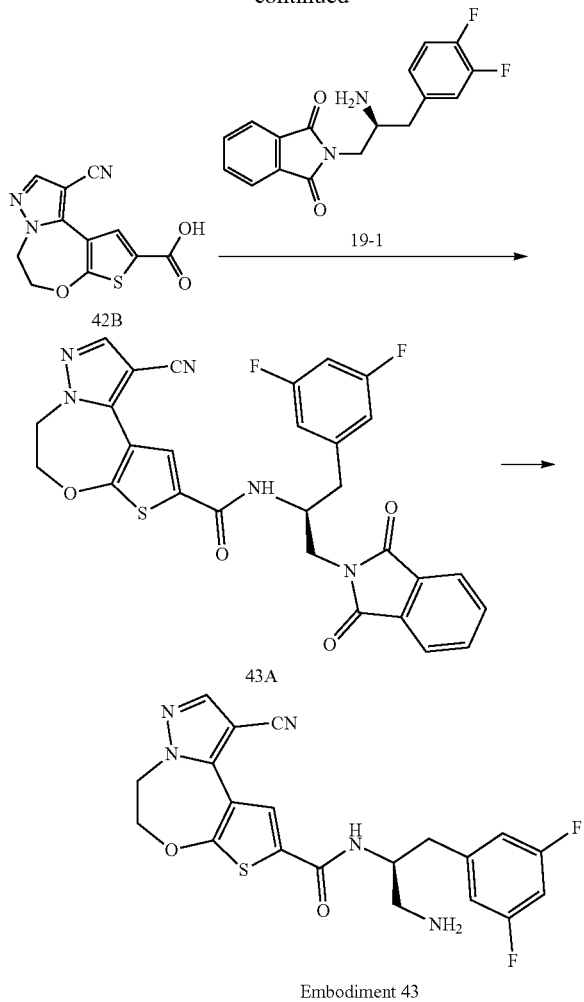

Embodiment 43

Intermediate 43A: 10-cyano-N—((S)-1-(3,5-difluorophenyl)-3-(1,3-dioxoisoindolin-2-yl)propan-2-yl)-5,6-dihydropyrazolo[1,5-d]thieno[3,2-f][1,4]oxazepine-2-carboxamide Prepare according to the method as described in embodiment 41A. LCMS (ESI) m/z: 560 (M+1).

Preparation of Embodiment 43

Prepare according to the method as described in embodiment 15. LCMS (ESI) m/z: 430 (M+1). $^1$H NMR (400 MHz, METHANOL-d4) δ ppm 2.83-2.92 (m, 1H), 2.98-3.10 (m, 2H), 3.16-3.23 (m, 1H), 4.43 (br dd, J=5.52, 4.27 Hz, 1H), 4.65-4.72 (m, 2H), 4.75-4.82 (m, 2H), 7.09-7.14 (m, 1H), 7.16-7.25 (m, 2H), 7.92 (s, 1H), 8.05 (s, 1H), 8.54 (br s, 1H).

Biological Assay

Study 1: The Inhibitory Effect of the Compounds on the Activity of Akt1, Akt2 and Akt3

Reagents and Materials:

ULight-CREBtide (PerkinElmer # TRF0107-M, lot2035700)

Europium-Anti-P-CREB (Ser-133) (PerkinElmer # TRF0200-M,lot2002391)

LANCE Detection Buffer, 10* (PerkinElmer # CR97-100)

ATP (Invitrogen # PV3227)

Akt1 protein (life technology # lot11629928C)

Akt2 protein (life technology # lot 28870GG)

Akt3 protein (life technology # lot 1715050B)

384-well platetest plate (PerkinElmer #6007299)

Experimental Principles:

In this experiment, a homogeneous time-resolved fluorescence conjugate energy transfer (LANCE TR-FRET®) method was used. In the assay plate, enzymes, biotinylated polypeptide substrates and compound to be tested were mixed, and ATP was added to initiate the reaction and the mixture was incubated. After that, EDTA was added to terminate the reaction while an Eu-labeled antibody was added to carry out the reaction and the reaction was then detected. The assay plate was analyzed by PE company's Envision, and the analysis mode was TR-FRET. The data were represented by fluorescence signals at 665 nm and 615 nm, respectively. A high ratio of fluorescence signal at 665 nm/615 nm indicates a higher activity, while a low ratio of 665 nm/615 nm indicates that the activity is inhibited.

Experimental Methods:

Compound formulation: compound to be tested and the reference compound were diluted with 100% DMSO, the initial concentration of the compound was 10 uM, and diluted by 10 times in a 3-fold gradient. Transfer the compound to the cell plate and duplicate each well.

Kinase assay: the enzyme and substrate were mixed with different concentrations of pre-diluted compounds. The final concentrations of Akt1, Akt2, and Akt3 kinase were 1.25 nM, 2 nM, and 2 nM, respectively. Leave at room temperature for 15 min and diplicate each concentration. ATP was added, and the final concentrations were 36 uM, 360 uM and 160 uM in Akt1, Akt2, and Akt3 kinase reactions, respectively, and the reaction was carried out for 90 min at room temperature (in which negative and positive controls were set). After the reaction was completed, the antibody was added and the mixture was detected, and the cells were incubated for 60 min at room temperature, and then collected by Evnvision. Data analysis and fitting according to *Lfit5 software.

Experimental results: See Table 1.

Conclusions: The embodiment compounds have strong inhibitory activities on Akt1, Akt2 and Akt3.

TABLE 1

| Compound to be tested | Akt1 IC$_{50}$ (nM) | Akt2 IC$_{50}$ (nM) | Akt3 IC$_{50}$ (nM) |
| --- | --- | --- | --- |
| Embodiment 1 | 0.36 | 24 | 21 |
| Embodiment 2 | 6.64 | 266 | 294 |
| Embodiment 3 | 39 | 163 | 1133 |
| Embodiment 4 | 0.6 | 32 | 40 |
| Embodiment 5 | 2.54 | 77 | 77 |
| Embodiment 6 | 3.78 | 101 | 95 |
| Embodiment 7 | 0.71 | 19 | 24 |
| Embodiment 8 | 3.62 | 107 | 69 |
| Embodiment 9 | 1.39 | 25 | 44 |
| Embodiment 10 | 0.63 | 17 | 29 |
| Embodiment 11 | 2.28 | 66 | 80 |
| Embodiment 12 | 116 | 4826 | 867 |
| Embodiment 13 | 11 | 188 | 189 |
| Embodiment 14 | 0.33 | 11 | 34 |
| Embodiment 15 | 0.67 | 20 | 16 |
| Embodiment 16 | 0.85 | 45 | 45 |
| Embodiment 17 | 0.68 | 38 | 41 |
| Embodiment 18 | 0.27 | 8 | 10 |
| Embodiment 19 | 0.03 | 8.0 | 8.7 |
| Embodiment 20 | 11 | 428 | 374 |
| Embodiment 21 | 13.3 | 312 | 98 |
| Embodiment 22 | 2.18 | 26 | 60 |

TABLE 1-continued

| Compound to be tested | Akt1 IC$_{50}$ (nM) | Akt2 IC$_{50}$ (nM) | Akt3 IC$_{50}$ (nM) |
|---|---|---|---|
| Embodiment 23 | 8.84 | 372 | 52 |
| Embodiment 24 | 67.36 | 1859 | 398 |
| Embodiment 25 | 5.22 | 143 | 83 |
| Embodiment 26 | 18.53 | 219 | 93 |
| Embodiment 27 | 14.71 | 304 | 119 |
| Embodiment 28 | 33.31 | 589 | 286 |
| Embodiment 29 | 35.99 | 1096 | 783 |
| Embodiment 30 | 12.43 | 281 | 485 |
| Embodiment 31 | 124 | 3131 | 819 |
| Embodiment 32 | 117 | 2929 | 814 |
| Embodiment 33 | 13 | 490 | 108 |
| Embodiment 34 | 36 | 983 | 513 |
| Embodiment 35 | 0.43 | 22 | 34 |
| Embodiment 36 | 9.78 | 235 | 195 |
| Embodiment 37 | 1.73 | 35 | 29 |
| Embodiment 38 | 0.36 | 57 | 68 |
| Embodiment 39 | 1.5 | 76 | 122 |
| Embodiment 40 | 0.87 | 66 | 170 |
| Embodiment 41 | 1.45 | 39 | 57 |
| Embodiment 42 | 27.5 | 900 | 416 |
| Embodiment 43 | 36 | 856 | 627 |

Study 2: inhibitory effects of compounds on LNCaP cell activity

Reagents and Materials:

1. Cell culture: RPMI-1640 medium, fetal bovine serum, Accutase, DPBS

2. Cell line: LNCaP

3. Detection reagent: live cell detection kit CellTiter-Glo

4. Materials and reagents: compound dilution plate, intermediate plate, test plate, DMSO Experimental Principles:

The amount of ATP directly reflects the number and the state of the cells, and the number of live cells can be detected by quantitatively measuring ATP. The live cell assay kit contains luciferase and its substrate. Through the participation of ATP, luciferase can catalyze the substrate, emit a stable optical signal, and the amount of ATP in the cell was determined by detecting the intensity of the signal. Wherein, the optical signal is proportional to the amount of ATP in the cell, and ATP is positively correlated with the number of live cells, so that the cell proliferation can be detected. The assay board is analyzed by PE company's Envision.

Experimental Methods:

1. Preparation of Cell Plates

LNCaP cell was separately seeded in a 384-well plate, each well contains 1000 cells. The cell plate was placed in a carbon dioxide incubator and incubated overnight.

2. Compound Formulation

A duplicated experiment was performed with 10 concentrations of compound in a 3-fold dilution with Bravo.

3. Compound Treating Cells

Compound was transferred to the cell plate with a starting concentration of 10 uM. The cell plate was incubated in a carbon dioxide incubator for 3 days.

4. Detection

The Promega CellTiter-Glo reagent was added to the cell plate and incubated for 10 min at room temperature to stabilize the optical signal. Read the data by a PerkinElmer Envision multi-label analyzer.

Experimental results: See Table 2.

Conclusions: The embodiment compounds showed better inhibitory activity against LNCaP cells.

TABLE 2

| Compound to be tested | LNcap cell IC$_{50}$ (nM) | Compound to be tested | LNcap cell IC$_{50}$ (nM) |
|---|---|---|---|
| Embodiment 1 | 58 | Embodiment 23 | 1339 |
| Embodiment 2 | 666 | Embodiment 24 | 3556 |
| Embodiment 3 | 2010 | Embodiment 25 | 389 |
| Embodiment 4 | 182 | Embodiment 26 | 613 |
| Embodiment 5 | 199 | Embodiment 27 | 971 |
| Embodiment 6 | 297 | Embodiment 28 | 1422 |
| Embodiment 7 | 59 | Embodiment 29 | 2615 |
| Embodiment 8 | 534 | Embodiment 30 | 654 |
| Embodiment 9 | 236 | Embodiment 31 | 5711 |
| Embodiment 10 | 159 | Embodiment 32 | >10000 |
| Embodiment 11 | 287 | Embodiment 33 | 1748 |
| Embodiment 12 | 4890 | Embodiment 34 | 2356 |
| Embodiment 13 | 514 | Embodiment 35 | 150 |
| Embodiment 14 | 36 | Embodiment 36 | 902 |
| Embodiment 15 | 85 | Embodiment 37 | 98 |
| Embodiment 16 | 233 | Embodiment 38 | 118 |
| Embodiment 17 | 230 | Embodiment 39 | 144 |
| Embodiment 18 | 77 | Embodiment 40 | 87 |
| Embodiment 19 | 23 | Embodiment 41 | 62 |
| Embodiment 20 | 487 | Embodiment 42 | 663 |
| Embodiment 21 | 615 | Embodiment 43 | 792 |
| Embodiment 22 | 61 | | |

What is claimed is:

1. A compound of formula (I) or a pharmaceutically acceptable salt thereof,

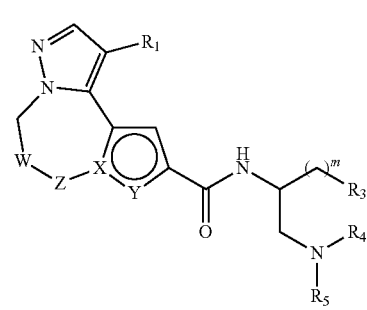

(I)

wherein, $R_1$ is H, halogen, CN, $CH_3$, $CH_2CH_3$, $CF_3$, cyclopropyl, phenyl or pyridyl;

X is C or N;

Y is S, O, N or $N(CH_3)$;

Z is $C(R_{21})(R_{22})$, $C(=O)$, O or S;

W is $C(R_{61})(R_{62})$ or $C(=O)$;

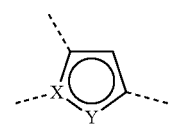

is a five-membered heteroaryl;

each of $R_{21}$, $R_{22}$, $R_{61}$ and $R_{62}$ is independently H, halogen, hydroxyl, amino or methoxy;

m is 0, 1 or 2;

$R_3$ is phenyl or pyridyl, which is optionally substituted by 1, 2 or 3 R;

each of $R_4$ and $R_5$ is independently H or $CH_3$;

R is F, Cl, CN or $CF_3$.

2. The compound or the pharmaceutically acceptable salt thereof according to claim 1, wherein $R_1$ is F, Cl, Br, I, CN, $CH_3$, $CH_2CH_3$, $CF_3$,

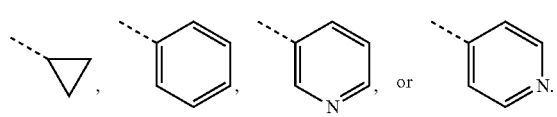

3. The compound or the pharmaceutically acceptable salt thereof according to claim 1, wherein the moiety

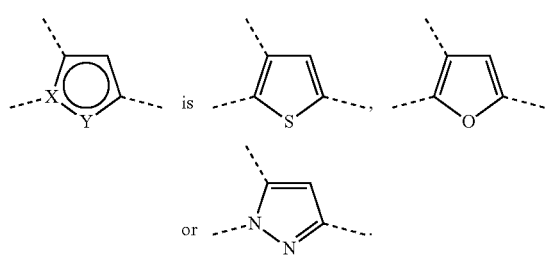

4. The compound or the pharmaceutically acceptable salt thereof according to claim 1, wherein the moiety

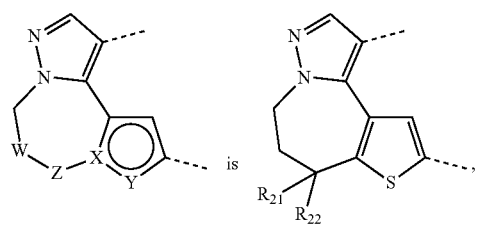

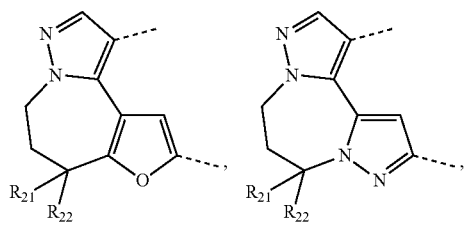

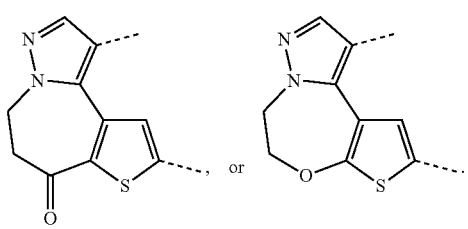

5. The compound or the pharmaceutically acceptable salt thereof according to claim 4, wherein the moiety

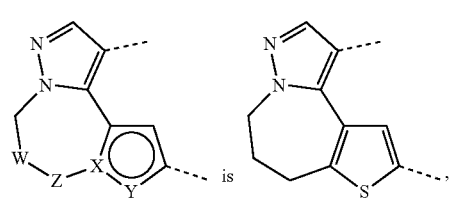

-continued

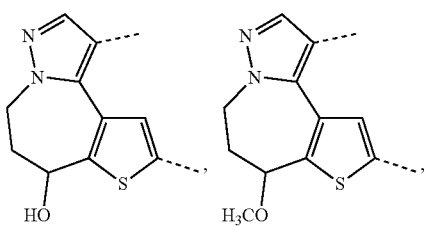

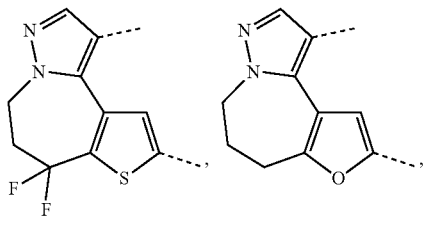

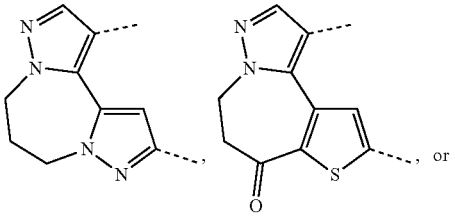

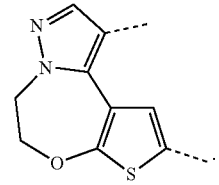

6. The compound or the pharmaceutically acceptable salt thereof according to claim 1, wherein $R_3$ is

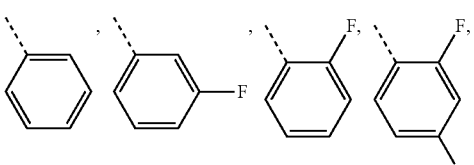

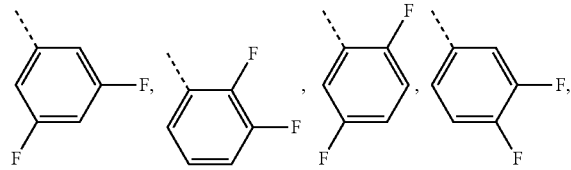

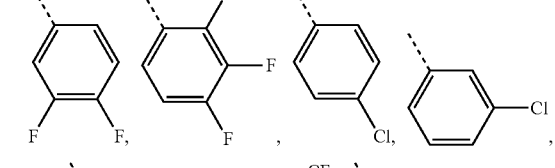

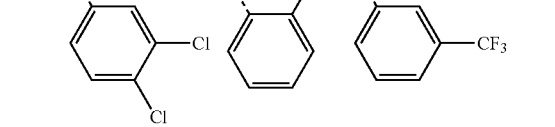

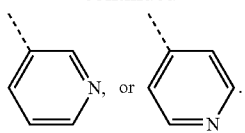
7. The compound or the pharmaceutically acceptable salt thereof according to claim 1, which is selected from the group consisting of
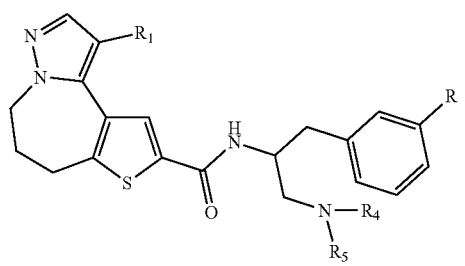
(I-1)
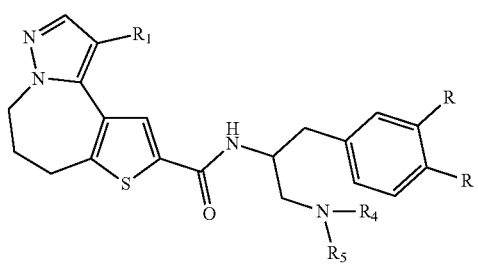
(I-2)
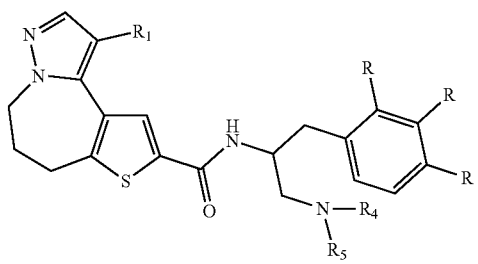
(I-3)
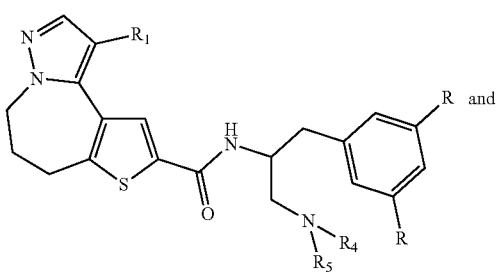
(I-4)
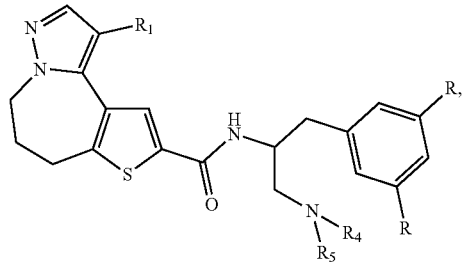
(I-5)
wherein R, $R_1$, $R_4$, $R_5$ are as defined in claim 1.
8. The compound or the pharmaceutically acceptable salt thereof according to claim 7, which is selected from the group consisting of
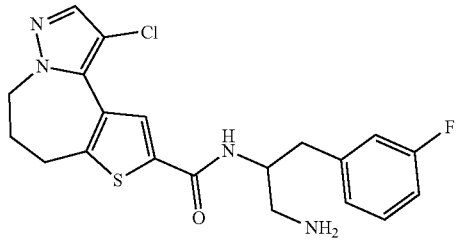
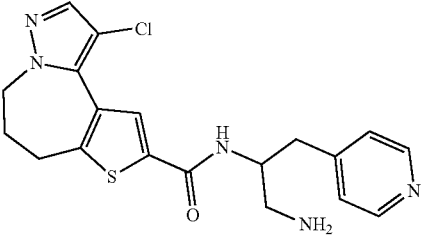
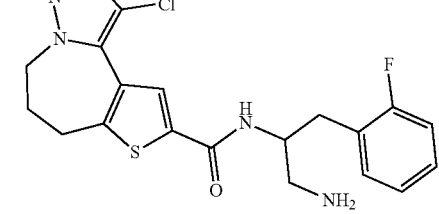
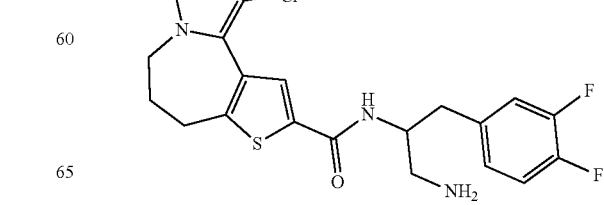

115
-continued
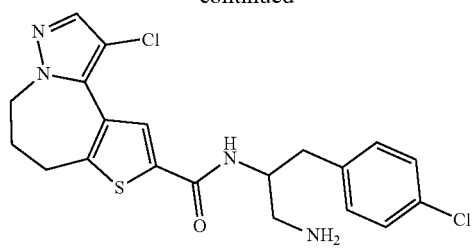
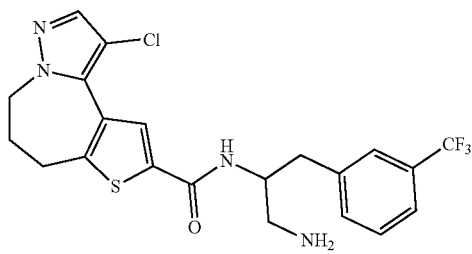
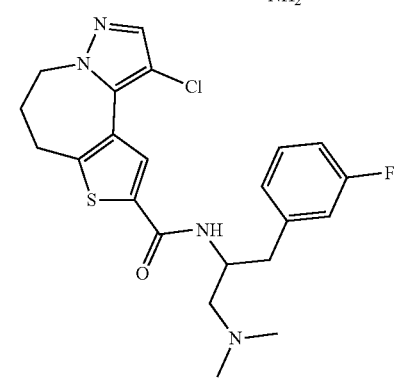
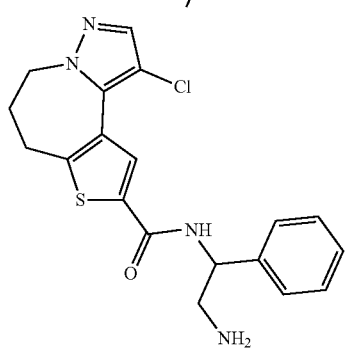
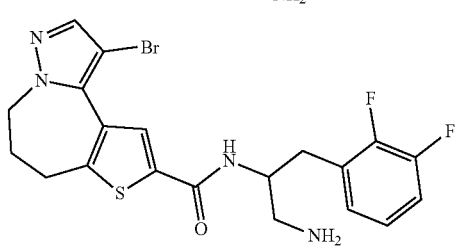
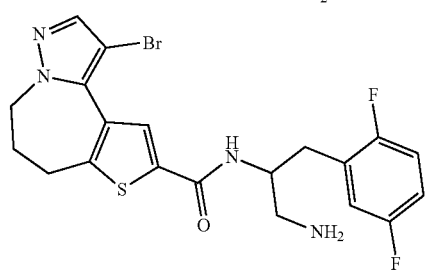
116
-continued
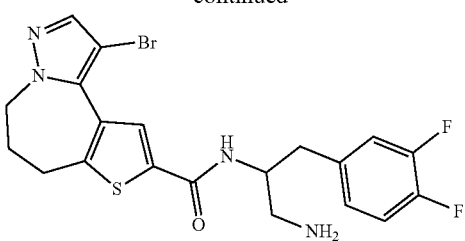
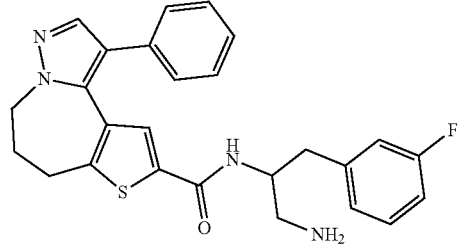
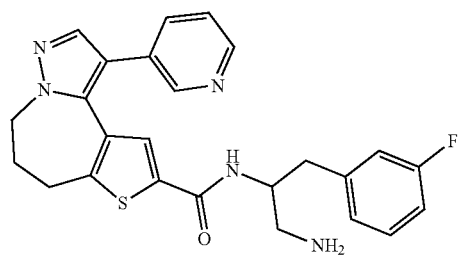
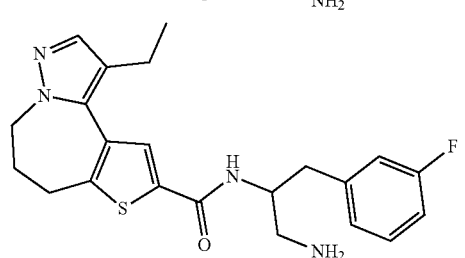
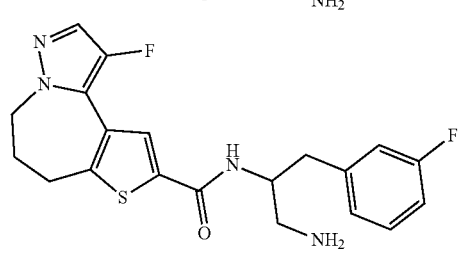
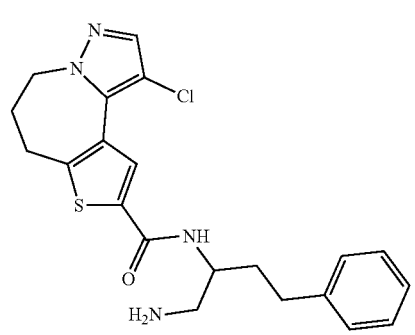

117
-continued
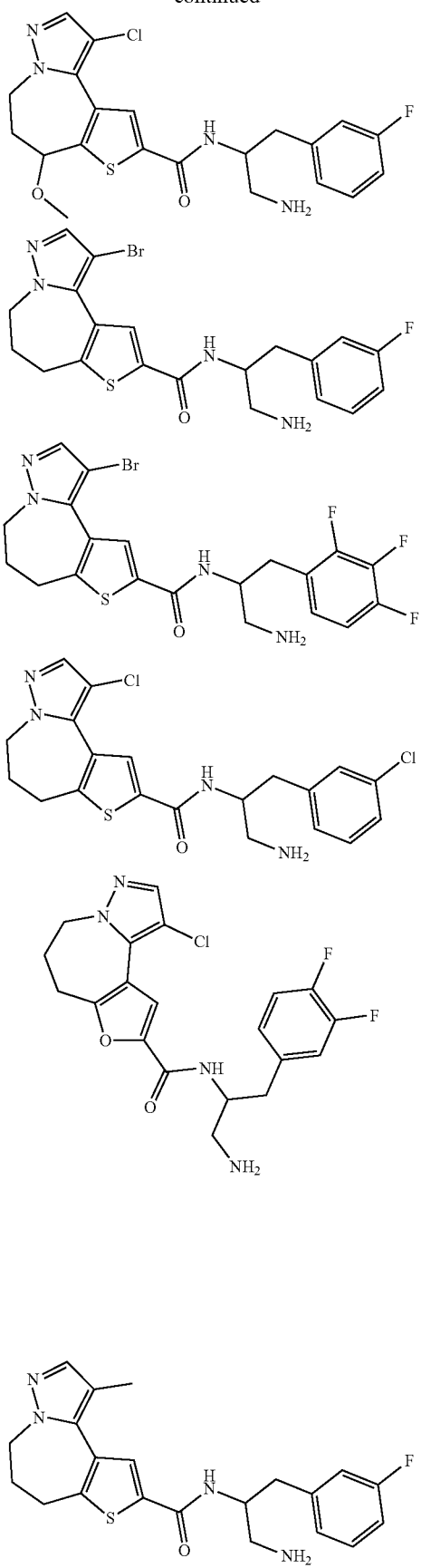
118
-continued
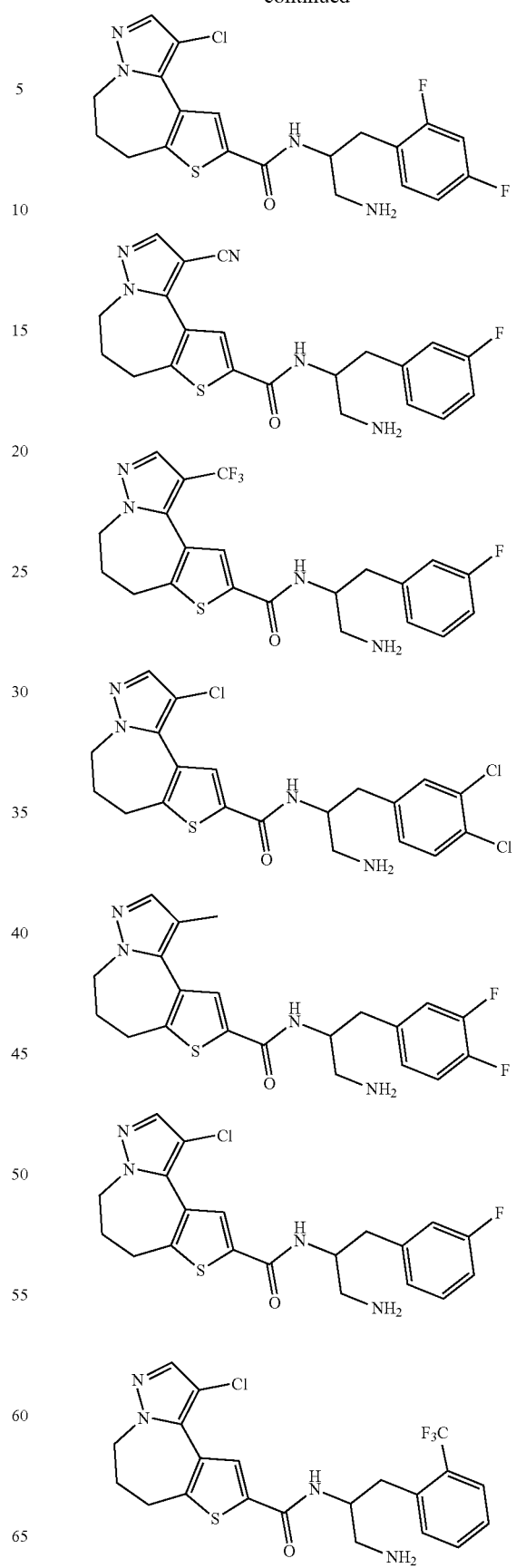

-continued
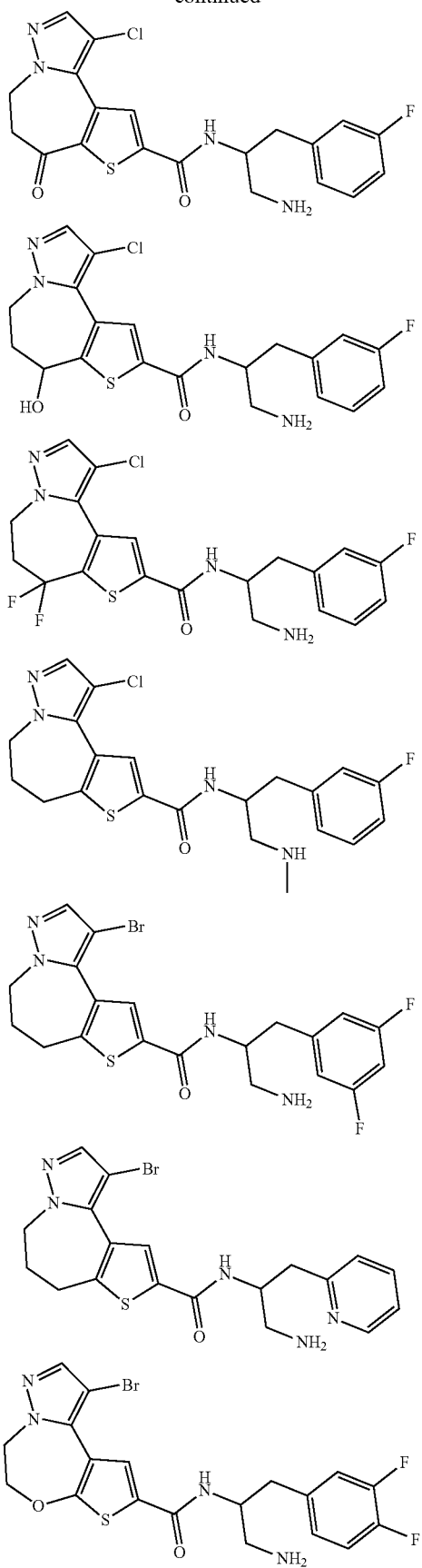
-continued
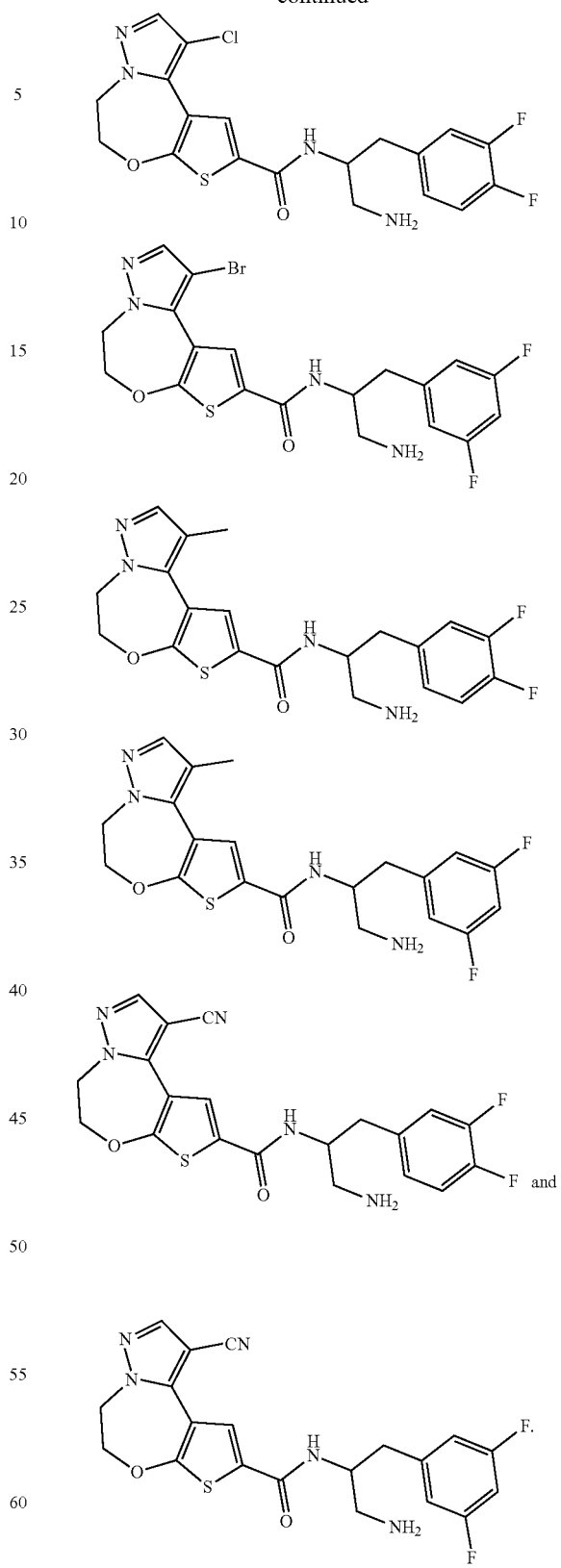
9. The compound or the pharmaceutically acceptable salt thereof according to claim 8, which is selected from the group consisting of 121
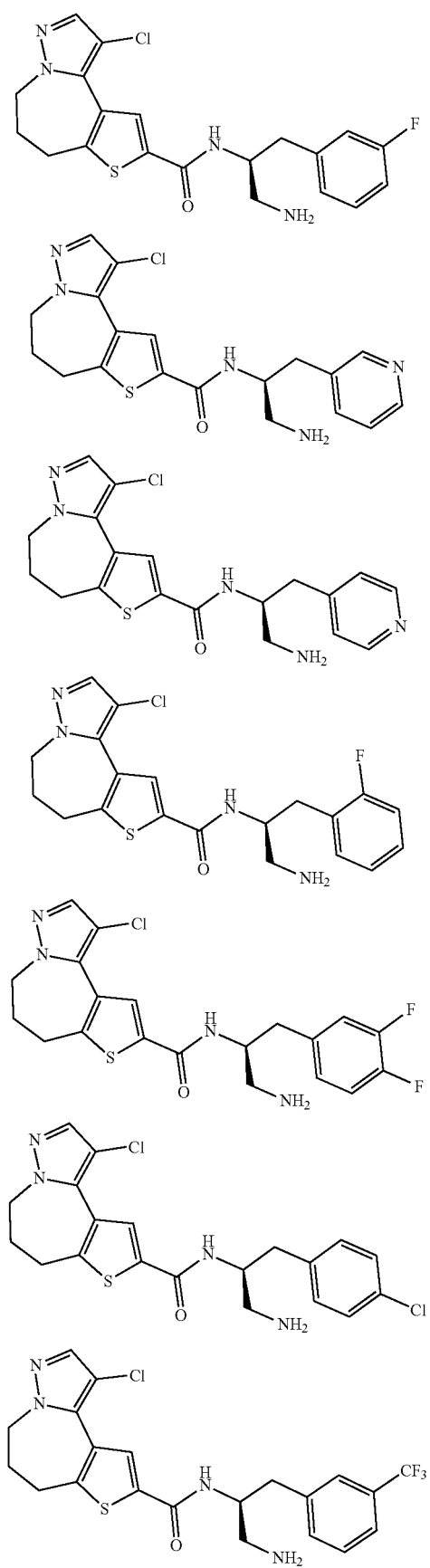
122
-continued
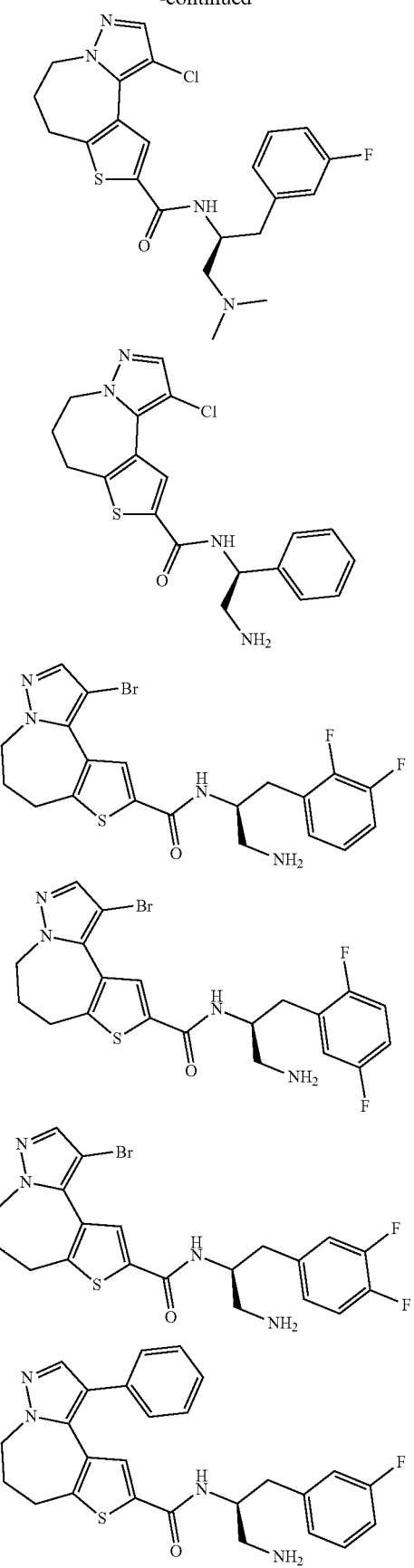

123
-continued
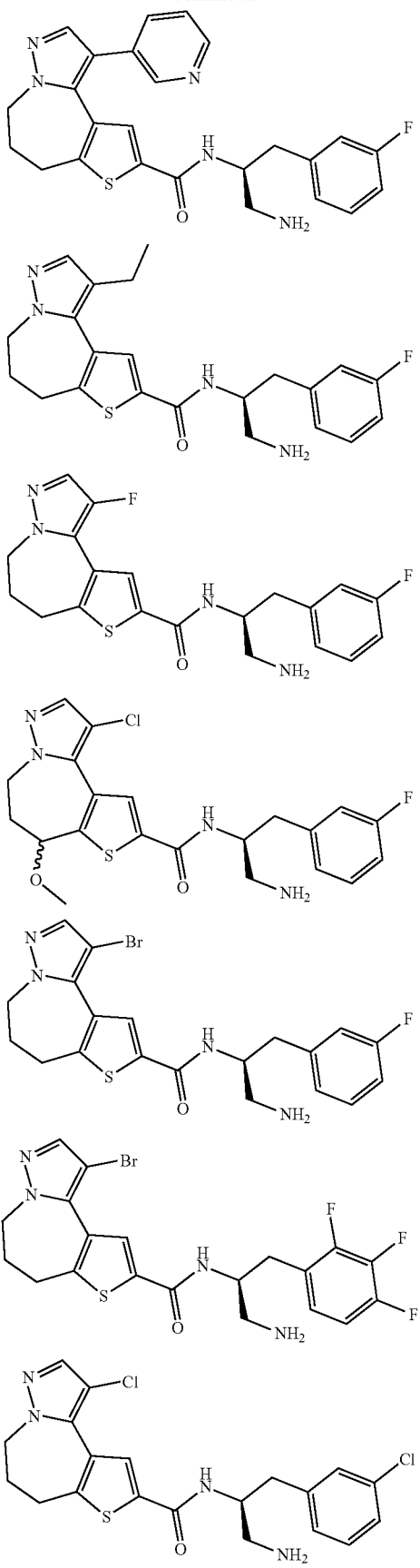
124
-continued
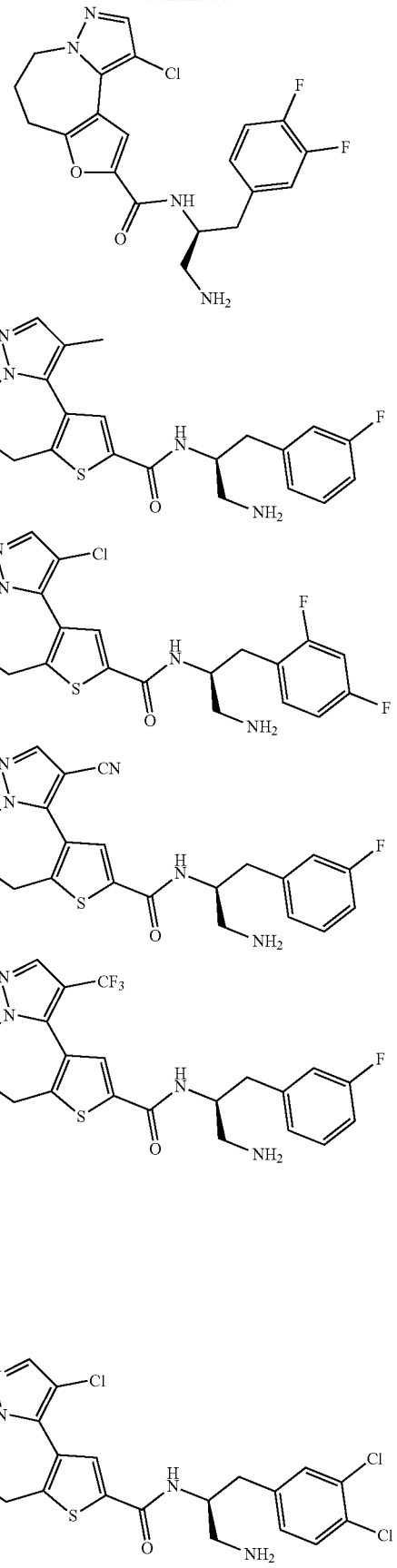

125
-continued
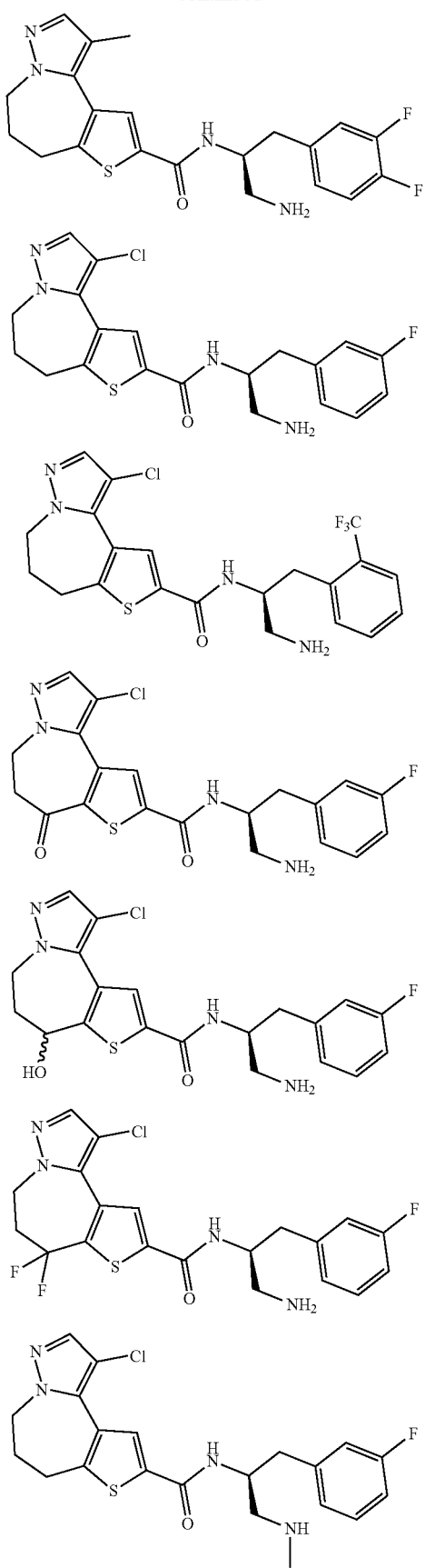
126
-continued
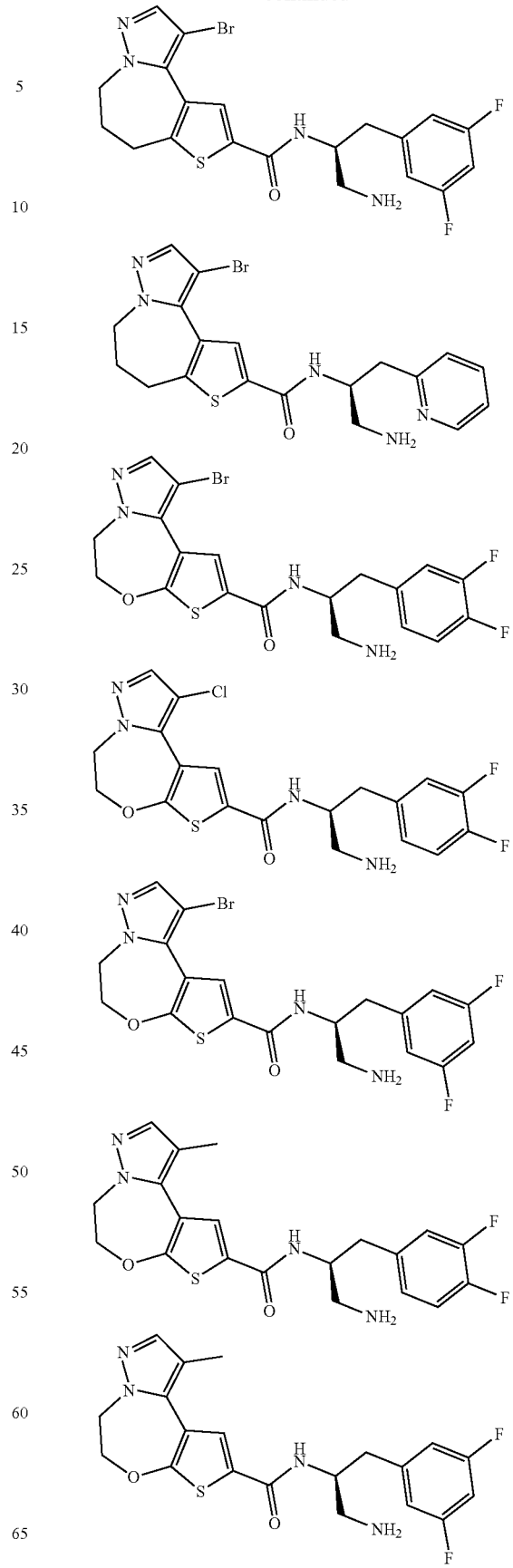

-continued

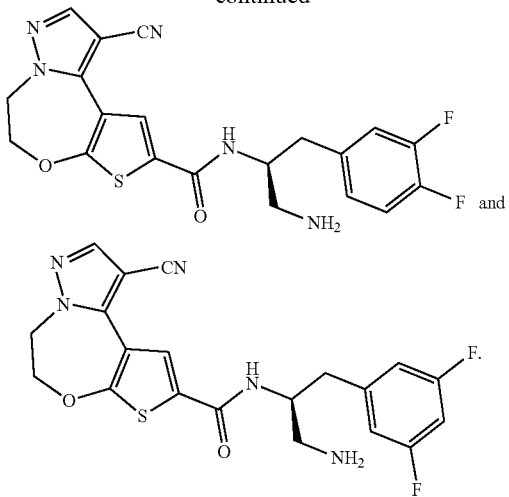

10. A pharmaceutical composition, comprising a therapeutically effective dose of the compound or the pharmaceutically acceptable salt according to claim 1, and a pharmaceutically acceptable carrier.

11. A method for treating a tumor comprising Akt1-E17K, diabetes, or rheumatoid arthritis in a subject in need thereof, the method comprising administering an effective amount of the compound or the pharmaceutically acceptable salt thereof according to claim 1 to the subject.

12. A method for treating a tumor comprising Akt1-E17K, diabetes, or rheumatoid arthritis in a subject in need thereof, the method comprising administering an effective amount of the pharmaceutical composition according to claim 10 to the subject.

* * * * *